United States Patent
Annala et al.

(10) Patent No.: US 11,413,315 B2
(45) Date of Patent: Aug. 16, 2022

(54) NEURAL STEM CELL-MEDIATED CANCER TREATMENT

(71) Applicant: CITY OF HOPE, Duarte, CA (US)

(72) Inventors: Alexandra Jaqueline Annala, Arcadia, CA (US); Karen Aboody, Arcadia, CA (US); Jennifer Covello, Fontana, CA (US); Rachael Mooney, Monument, CA (US)

(73) Assignee: CITY OF HOPE, Duarte, CA (US)

( * ) Notice: Subject to any disclaimer, the term of this patent is extended or adjusted under 35 U.S.C. 154(b) by 432 days.

(21) Appl. No.: 16/398,108

(22) Filed: Apr. 29, 2019

(65) Prior Publication Data
US 2020/0038453 A1 Feb. 6, 2020

Related U.S. Application Data

(60) Provisional application No. 62/664,268, filed on Apr. 29, 2018.

(51) Int. Cl.
*A61K 35/30* (2015.01)
*A61K 31/7105* (2006.01)
*A61K 35/761* (2015.01)
*A61P 35/00* (2006.01)
*A61K 45/00* (2006.01)

(52) U.S. Cl.
CPC .......... *A61K 35/30* (2013.01); *A61K 31/7105* (2013.01); *A61K 35/761* (2013.01); *A61P 35/00* (2018.01); *A61K 45/05* (2013.01)

(58) Field of Classification Search
CPC .................................................... A61K 35/30
See application file for complete search history.

(56) References Cited

U.S. PATENT DOCUMENTS

2016/0317591 A1* 11/2016 Aboody .................. A61K 35/30
2019/0374589 A1* 12/2019 Suzuki .................. A61K 35/761

OTHER PUBLICATIONS

Aboody et al. (Sci Transl Med. May 8, 2013; 5(184): doi:10.1126/scitranslmed.3005365) (Year: 2013).*
Lenz et al. (Mol Cancer Ther 2021;20:961-74) (Year: 2021).*
Alfano et al. (Molecular Therapy: Oncolytics vol. Sep. 6, 2017) (Year: 2017).*
Casey et al. (Science 352.6282 (2016): 227-231). (Year: 2016).*
Aboody, K. S., et al., "Neural stem cells display extensive tropism for pathology in adult brain: Evidence from intracranial gliomas," PNAS 97(23):12846-12851 (2000).
Aboody, K. S., et al., "Neural stem cell-mediated enzyme-prodrug therapy for glioma: Preclinical studies," Sci. Transl. Med. 5(184):184ra59 (2013).
Ahmed, A. U., et al., "Neural stem cell-based cell carriers enhance therapeutic efficacy of an oncolytic adenovirus in an orthotopic mouse model of human glioblastoma," Mol. Ther. 19(9):1714-1726 (2011).
Ahmed, A. U., et al., "A preclinical evaluation of neural stem cell-based cell carrier for targeted antiglioma oncolytic virotherapy," J. Natl. Cancer Inst. 105:968-977 (2013).
Ansari, M. J. I., et al., "The programmed death-1 (PD-1) pathway regulates autoimmune diabetes in nonobese diabetic (NOD) mice," J. Exp. Med. 198(1):63-69 (2003).
Bonome, T., et al., "A gene signature predicting for survival in suboptimally debulked patients with ovarian cancer," Cancer Res. 68(13):5478-5486 (2008).
Cannistra, S. A., "Cancer of the ovary," New Engl. J. Med. 351:2519-2529 (2004).
Cao, P., et al., "Intraperitoneal administration of neural stem cell-nanoparticle conjugates targets chemotherapy to ovarian tumors," Bioconjug. Chem. 28(6):1767-1776 (2017).
Casey, S. C., et al., "MYC regulates the anti-tumor immune response through CD47 and PD-L1," Science 352(6282):227-231 (2016).
Cerami, E., et al., "The cBio cancer genomics portal: An open platform for exploring multidimensional cancer genomics data," Cancer Discov. 2(5):401-404 (2012).
Chen, L., et al., "Anti-PD-1/PD-L1 therapy of human cancer: past, present, and future," J. Clin. Invest. 125(9):3384-3391 (2015).
Chou, T.C., "Theoretical basis, experimental design, and computerized simulation of synergism and antagonism in drug combination studies," Pharmacol. Rev. 58(3):621-681 (2006).
Ding, J., "Oncolytic virus as a cancer stem cell killer: progress and challenges," Stem Cell Investig. 1:22 (2014).
Domcke, S., et al., "Evaluating cell lines as tumour models by comparison of genomic profiles," Nat. Commun. 4:2126 (2013).
Douglas, J. T., et al., "Efficient oncolysis by a replicating adenovirus (Ad) in vivo is critically dependent on tumor expression of primary ad receptors," Cancer Res. 61:813-817 (2001).

(Continued)

*Primary Examiner* — Scott Long
(74) *Attorney, Agent, or Firm* — Perkins Coie LLP; Lara J. Dueppen; Yang Tang

(57) ABSTRACT

Provided are methods and compositions for treating cancer with a combination of neural stem cells (NSCs) and an oncolytic virus or a combination of oncolytic virotherapy and immune modulation. The method entails administrating to a subject a pharmaceutical composition comprising a combination of NSCs and an oncolytic virus, and/or NSCs packaged with one or more immunomodulatory viruses expressing one or more immunity checkpoint inhibitors, including adaptive immunity checkpoint inhibitors and innate immunity checkpoint inhibitors. The immunity checkpoint inhibitors include shRNAs against the immunity checkpoint proteins. The cancer includes but is not limited to primary, recurrent, and metastatic brain cancer, breast cancer, head and neck cancer, bladder cancer, ovarian cancer, uterine cancer, prostate cancer, skin cancer, lung cancer, and colorectal cancer.

16 Claims, 28 Drawing Sheets
(27 of 28 Drawing Sheet(s) Filed in Color)
Specification includes a Sequence Listing.

(56) References Cited

OTHER PUBLICATIONS

Duraiswamy, J., et al., "Dual blockade of PD-1 and CTLA-4 combined with tumor vaccine effectively restores T-cell rejection function in tumors," Cancer Res. 73(12):3591-3603 (2013).

Gaillard, S. L., et al., "The role of immune checkpoint inhibition in the treatment of ovarian cancer," Gynecol. Oncol. Res. Pract. 3:11 (2016).

Gao, J., et al., "Integrative analysis of complex cancer genomics and clinical profiles using the cBioPortal," Sci. Signal 6(269):p. 11 (2013).

Hartkopf, A. D., et al., "Oncolytic viruses to treat ovarian cancer patients—A review of results from clinical trials," Geburtshilfe Frauenheilkd 72(2):132-136 (2012).

He, T.C., et al., "A simplified system for generating recombinant adenoviruses," Proc. Natl. Acad. Sci. 95:2509-2514 (1998).

Heise, C., et al., "Efficacy of a replication-selective adenovirus against ovarian carcinomatosis is depdendent on tumor burden, viral replication and p53 status," Gene Ther. 7:1925-1929 (2000).

Helm, C. W., et al., "Enhancing the efficacy of cisplatin in ovarian cancer treatment—could arsenic have a role," J. Ovarian Res. 2:2 (2009).

Hulin-Curtis, S.L., et al., "Evaluation of CD46 re-targeted adenoviral vectors for clinical ovarian cancer intraperitoneal therapy," Cancer Gene Ther. 23:229-234 (2016).

Jemal, A., et al., "Cancer statistics, 2008," CA Cancer J. Clin. 58:71-96 (2008).

Joshi, M.N., et al., "Immune checkpoint inhibitor-related hypophysitis and endocrine dysfunction: clinical review," Clin. Endocrinol. 85:331-339 (2016).

Kendall, S. E., et al., "Neural stem cell targeting of glioma is dependent on phosphoinositide 3-kinase signaling," Stem Cells 26:1575-1586 (2008).

Kim, J. et al., "Stem cell-based cell carrier for targeted oncolytic virotherapy: Translational opportunity and open questions," Viruses 7:6200-6217 (2015).

Kojima, Y., et al., "CD47 blocking antibodies restore phagocytosis and prevent atherosclerosis," Nature 536(7614):86-90 (2016).

Kong, Y.C. M., et al., "Opportunistic autoimmune disorders potentiated by immune-checkpoint inhibitors anti-CTLA-4 and anti-PD-1," Front. Immunol. 5(206):1-8 (2014).

Leng, S. X., et al., "Elisa and multiplex technologies for cytokine measurement in inflammation and aging research," J. Gerontol. A Biol. Sci. Med. Sci. 63(8):879-884 (2008).

Li, S., et al., "Oncolytic virotherapy for ovarian cancer," Oncolytic Virother. 1:1-21 (2012).

Liguang, Z., et al., "Survivin expression in ovarian cancer," Exp. Oncol. 29(2):121-125 (2007).

Machado, D., et al., Neural stem cell mediated delivery of AR2011 oncolytic virus for ovarian cancer, Abstract, ASGCT 21st Annual Meeting, Chicago, IL May 16-19, 2018.

Mader, E. K., et al., "Mesenchymal stem cell carriers protect oncolytic measles viruses from antibody neutralization in an orthotopic ovarian cancer therapy model," Clin. Cancer Res. 15(23):7246-7255 (2009).

Mader, E. K., et al., "Optimizing patient derived mesenchymal stem cells as virus carriers for a Phase I clinical trial in ovarian cancer," J. Transl. Med. 11:20 (2013).

Martini, E., et al., "Loss of surviving in intestinal epithelial progenitor cells leads to mitotic catastrophe and breakdown of gut immune homeostasis," Cell Rep. 14:1062-1073 (2016).

Mickelson, E. M., et al., "Evaluation of the mixed lumphocyte culture (MLC) assay as a method for selecting unrelated donors for marrow transplantation," Tissue Antigens 47:27-36 (1996).

Minev, B., et al., "Combination immunotherapy with oncolytic vaccinia virus and checkpoint inhibitor following local tumor irradiation," J. Immunother. Cancer 2(Suppl. 3):p. 112 (2014).

Mittal, A. K., et al., "Role of CTLA4 in the proliferation and survival of chronic lymphocytic leukemia," PLoS One 8(8):e70352 (2013).

Mizugaki, H., et al., "Phase I dose-finding study of monotherapy with atezolizumab, an engineered immunoglobulin monoclonal antibody targeting PD-L1, in Japanese patients with advanced solid tumors," Invest. New Drugs 34:596-603 (2016).

Mooney, R., et al., "Enhanced delivery of Oncolytic adenovirus by neural stem cells for treatment of metastatic ovarian cancer," Mol. Ther. Oncolytics 12:79-92 (2019).

Nayerossadat, N., et al., "Viral and nonviral delivery systems for gene delivery," Adv. Biomed. Res. 1:27 (2012).

Nwanegbo, E., et al., "Prevalence of neutralizing antibodies to adenoviral serotypes 5 and 35 in the adult populations of the Gambia, South Africa, and the United States," Clin. Diagn. Lab. Immunol. 11(2):351-357 (2004).

O'Driscoll, L., et al., "Survivin: Role in normal cells and in pathological conditions," Current Cancer Drug Targets 3:131-152 (2003).

Okazaki, T., et al., "PD-1 and PD-1 ligands: from discovery to clinical application," Int. Immunol. 19(7):813-824 (2007).

Ozols, R. F., et al., "High-dose cisplatin therapy in ovarian cancer," Semin. Oncol., vol. XII, No. 4, Suppl. 6: 21-30 (1985).

Pesonen, S., et al., "Oncolytic adenoviruses for the treatment of human cancer: Focus on translational and clinical data," Mol. Pharm. 8(1):12-28 (2011).

Power, A. T., et al., "Carrier cell-based delivery of an oncolytic virus circumvents antiviral immunity," Mol. Ther. 15(1):123-130 (2007).

Sah, N. K., et al., "Structural, functional and therapeutic biology of surviving," Cancer Letters 244:164-171 (2006).

Shinoura, N., et al., "Highly augmented cytopathic effect of a fiber-mutant E1B-defective adenovirus for gene therapy of gliomas," Cancer Res. 59:3411-3416 (1999).

Sprangers, M. C., et al., "Quantifying adenovirus-neutralizing antibodies by luciferase transgene detection: Addressing preexisting immunity to vaccine and gene therapy vectors," J. Clin. Microbiol. 41(11):5046-5052 (2003).

Stallwood, Y., et al., "Neutralisation of adenovirus infectivity by ascitic fluid from ovarian cancer patients," Gene Ther. 7:637-643 (2000).

Stoff, A., et al., "Strategies to enhance transductional efficiency of adenoviral-based gene transfer to primary human fibroblasts and keratinocytes as a platform in dermal wounds," Wound Repair Regen. 14(5):608-617 (2006).

Thaci, B., et al., "Pharmacokinetic study of neural stem cell-based cell carrier for oncolytic virotherapy: Targeted delivery of the therapeutic payload in an orthotopic brain tumor model," Cancer Gene Ther. 19(6):431-442 (2012).

Tirughana, R., et al., "GMP production and scale-up of adherent neural stem cells with a quantum cell expansion system," Mol. Ther. Meth. Clin. Devel. 10:48-56 (2018).

Ulasov, I. V., et al., "Survivin-driven and fiber-modified oncolytic adenovirus exhibits potent antitumor activity in established intracranial glioma," Hum. Gene Ther. 18:589-602 (2007).

Vasey, P. A., et al., "Phase I trial of intraperitoneal injection of the E1B-55-kd-gene-deleteeed adenovirus ONYX-015 (dl1520) given on days 1 through 5 every 3 weeks in patients with recurrent/refractory epithelial ovarian cancer," J. Clin. Oncol. 20:1562-1569 (2002).

Vathipadiekal, V., et al., "Creation of a human secretome: A novel composite library of human secreted proteins: Validation using ovarian cancer gene expression data and a virtual secretome array," Clin. Cancer Res. 21(21):4960-4969 (2015).

Wickham, T. J., et al., "Adenovirus targeted to heparan-containing receptors increases its gene delivery efficiency to multiple cell types," Nat. Biotechnol. 14:1570-1573 (1996).

Willingham, S. B., et al., "The CD47-signal regulatory protein alpha (SIRPa) interaction is a therapeutic target for human solid tumors," PNAS 109(17):6662-6667 (2012).

Zamarin, D., et al., "Localized oncolytic virotherapy overcomes systemic tumor resistance to immune checkpoint blockade immunotherapy," Sci. Transl. Med. 6(226):226ra32 (2014).

Zhu, Z. B., et al., "Transcriptional targeting of tumors with a novel tumor-specific surviving promoter," Cancer Gene Ther. 11:256-262 (2004).

(56) References Cited

OTHER PUBLICATIONS

Zitvogel, L., et al., "Targeting PD-1/PD-L1 interactions for cancer immunotherapy," Oncoimmunol. 1(8):1223-1225 (2012).

* cited by examiner

Fig. 14A
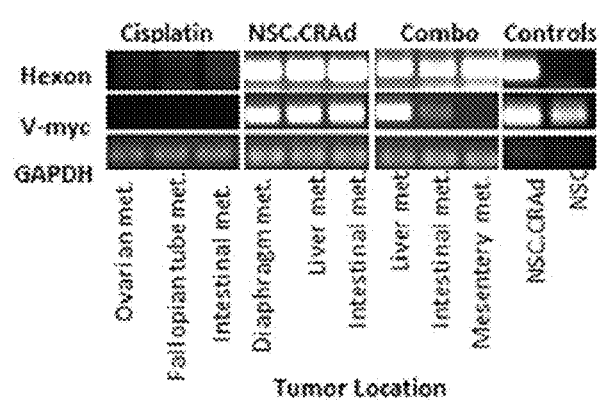
Fig. 14B
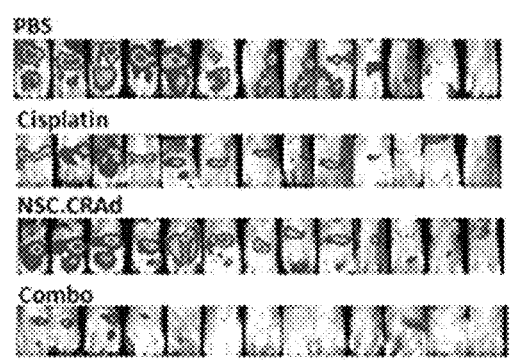
Fig. 14C
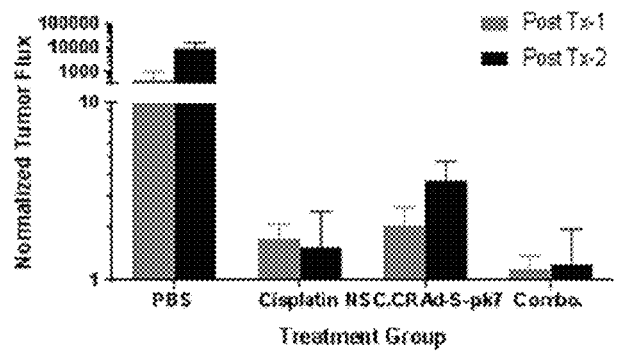
Fig. 14D
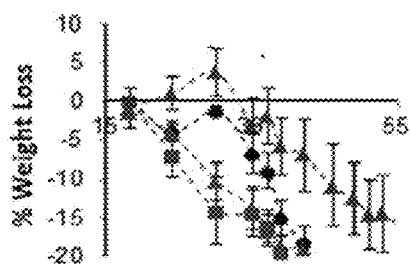
Fig. 14E Fig. 16A
Fig. 16B
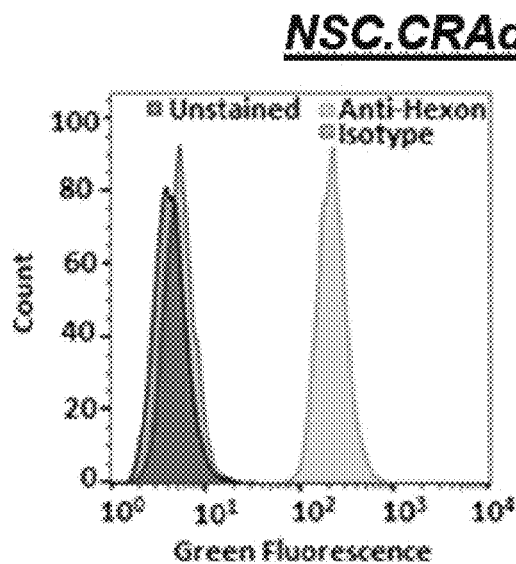
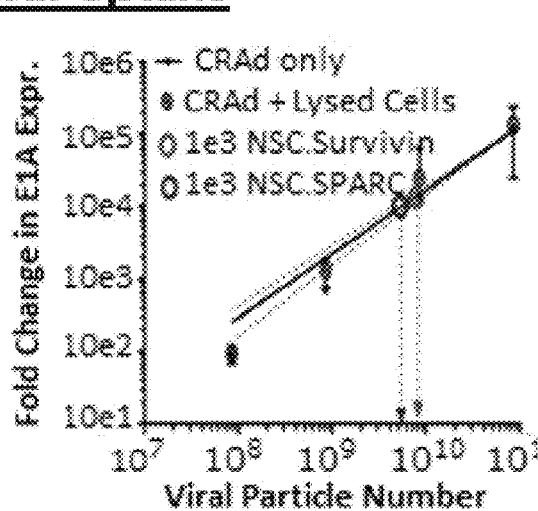
Fig. 16C
Fig. 16D
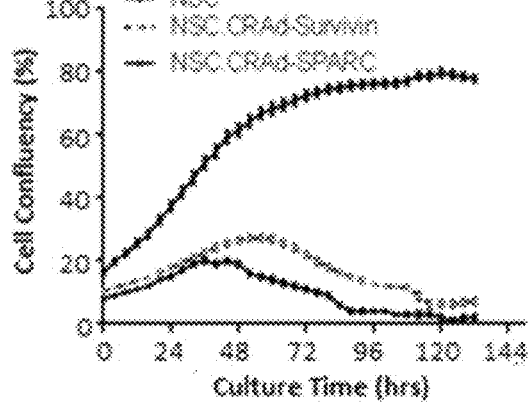
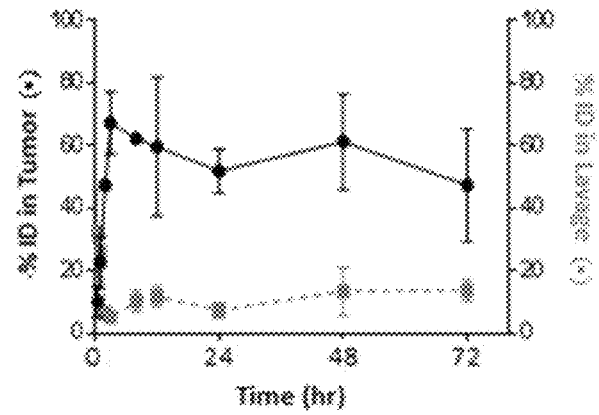

Fig. 19A
Fig. 19B
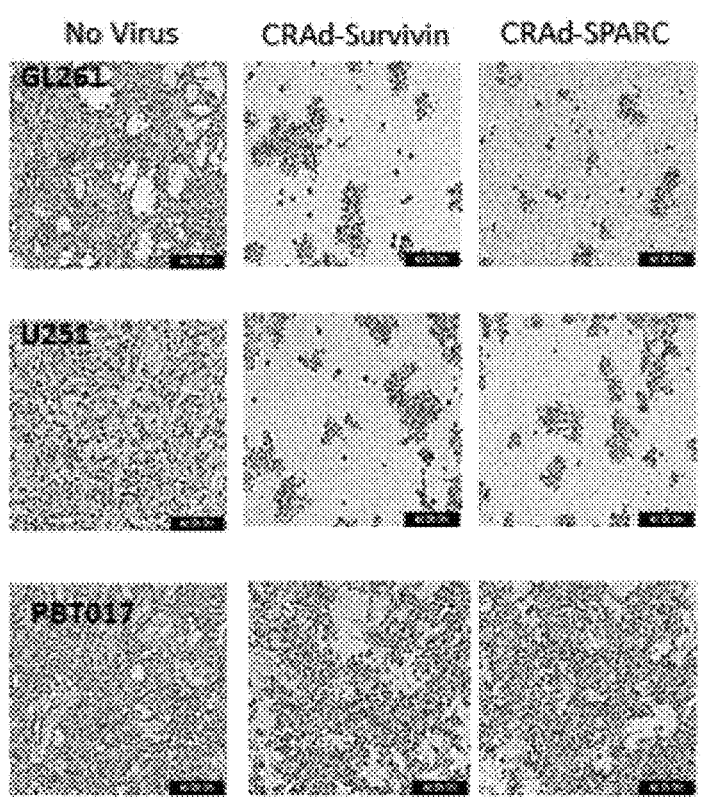
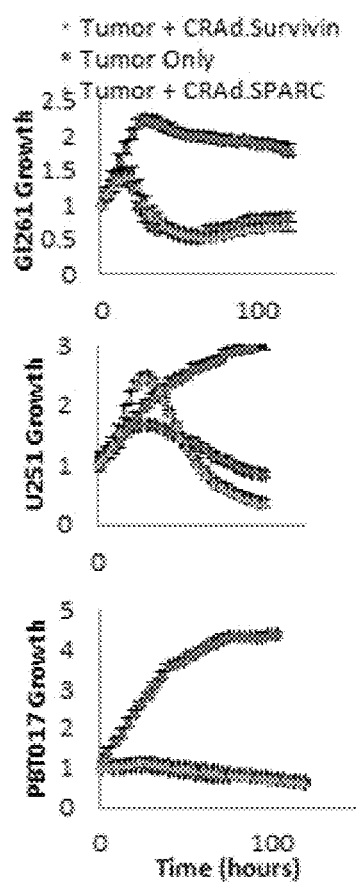

Fig. 23A
Fig. 23B
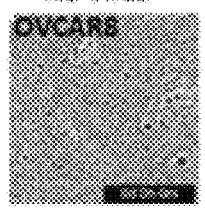 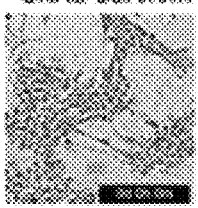 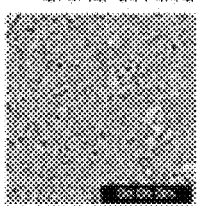 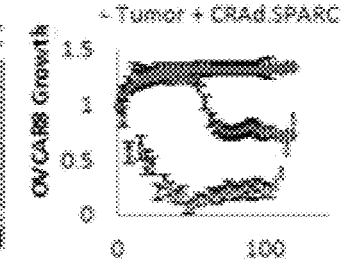
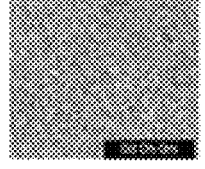 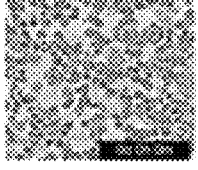 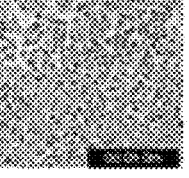 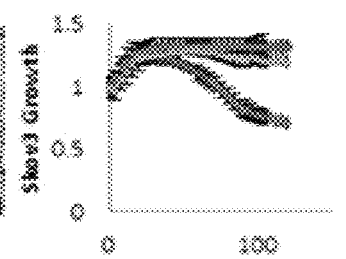
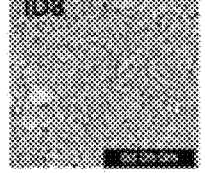 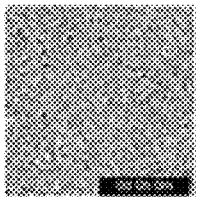 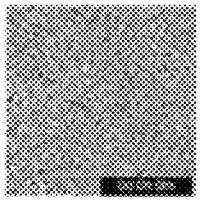 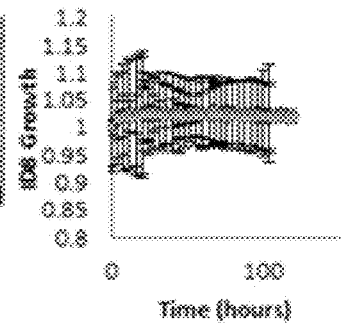
Time (hours)

Fig. 24A
Fig. 24B
Fig. 24C
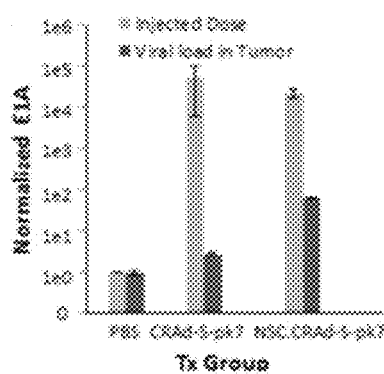
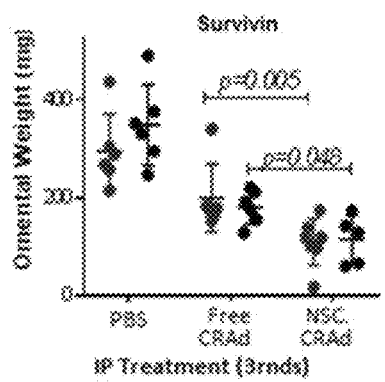
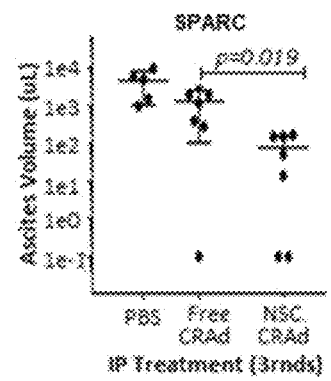

NEURAL STEM CELL-MEDIATED CANCER TREATMENT

CROSS-REFERENCE TO RELATED APPLICATIONS

This application claims the benefit of U.S. Provisional Patent Application No. 62/664,268 filed on Apr. 29, 2018, the disclosure of which is incorporated by reference in its entirety.

STATEMENT OF GOVERNMENT INTEREST

The present invention was made with government support under Grant Nos. R01CA198076, R01FD004816, U01N5082328, R43CA86768, and R44CA86768, awarded by the National Cancer Institute of the National Institutes of Health (NIH). The government has certain rights in the invention.

SEQUENCE LISTING

This disclosure includes a sequence listing, which was submitted in ASCII format via EFS-Web, and is hereby incorporated by reference in its entirety. The ASCII copy, created on Aug. 14, 2019, is named SequenceListing.txt and is 1.81 kilobytes in size.

BACKGROUND

Ovarian cancer is the most lethal gynecologic malignancy, afflicting approximately 22,000 women per year in the U.S. (Jemal et al., 2008; and Li et al., 2012). Once ovarian cancer has metastasized to the abdominal cavity (stage III), patients have only a 34% 5-year survival rate following standard treatment with surgical debulking and combination chemotherapy (e.g., cisplatin and paclitaxel) (Cannistra et al., 2004). Use of intraperitoneally (IP) delivered combination chemotherapy regimens has improved outcomes (Kim et al., 2015); however, these regimens frequently have complications and serious toxic side effects such that most patients are unable to complete the treatment cycles due to severe abdominal pain, nausea, and vomiting (Ding 2014). Furthermore, regardless of treatment regimen, most ovarian cancer patients eventually develop chemo-resistance, leading to cancer progression and death.

Along the same line, the 5-year survival rates for brain cancer is also significantly lower than those for other cancer types. Replication-competent oncolytic virotherapy is a promising approach for patients with recurrent disease, given that oncolytic viruses selectively replicate in tumors and induce cancer cell death irrespective of radio- or chemo-resistance. In addition, secondary immune responses are expected to be induced upon exposure of tumor antigens following the lysis of cancer cells. Although clinical trials have demonstrated the safety of oncolytic virotherapy, its efficacy has been limited by numerous obstacles, including poor viral penetration in tumors and poor viral spread through tumor-associated stroma and the tumor microenvironment. Therefore, new, more targeted and effective therapeutic approaches for treating recurrent and/or drug-resistant ovarian cancer and brain cancer are needed.

SUMMARY

In one aspect, provided herein is a method of treating cancer with neural stem cells (NSCs) mediated delivery of oncolytic adenovirus. The method entails administrating to a subject a therapeutically effective amount of NSCs and an oncolytic adenovirus. In some embodiments, the ratio of NSCs to the oncolytic adenovirus is about 100:1, about 200:1, about 300:1, about 400:1, about 500:1, about 600:1, about 700:1, about 800:1, about 900:1, about 1000:1, about 1100:1, about 1200:1, about 1300:1, about 1400:1, about 1500:1, about 1600:1, about 1700:1, about 1800:1, about 1900:1, or about 2000:1. In some embodiments, the NSCs and the oncolytic adenovirus are administered simultaneously. In some embodiments, the NSCs are transduced with the oncolytic adenovirus. In some embodiments, the NSCs and the oncolytic adenovirus are administered sequentially. In some embodiments, the NSCs and the oncolytic adenovirus are administered every day, every other day, every three days, every four days, every five days, every six days, weekly, every 10 days, bi-weekly, or monthly. In some embodiments, the NSCs and the oncolytic adenovirus are administered over the period of about one week, about two weeks, about three weeks, about four weeks, about five weeks, about six weeks, about seven weeks, about eight weeks, about nine weeks, about ten weeks, eleven weeks, twelve weeks, about four months, about five months, about six months, about seven months, about eight months, about nine months, about ten months, about eleven months, or about twelve months. In some embodiments, the NSCs and the oncolytic adenovirus are administered by injection, e.g., intraperitoneal injection. In some embodiments, the method further includes administering a therapeutically effective amount of one or more immune checkpoint inhibitors to the subject before, during, or after administration of the NSCs and the oncolytic adenovirus. The one or more immune checkpoint inhibitors include but are not limited to inhibitors for B7-1, B7-2, PD-1, PD-L1, PD-L2, CTLA-4, CD40, CD40L, CD47, CD48, CD244, CD80, CD86, CD155, IDO, CDK-12, Galectin-9, LAG-3, TIM-3, VISTA, TIGIT, SIRPα. The inhibitors can be small molecules, antibodies, minibodies, diabodies, triabodies, nanobodies, single domain antibodies. For example, a PD-L1 inhibitor such as a PD-L1 antibody or an shRNA against PD-L1 can be used. Alternatively, the inhibitors can be inactive "bait" proteins which compete to bind and displace checkpoint receptors, their ligands, and signaling molecules such as SIRPα. In some embodiments, the method further includes administering a therapeutically effective amount of a chemotherapeutic agent such as cisplatin. In some embodiments, the oncolytic virus belongs to adenovirus subtype 5 (Ad5). In some embodiments, the oncolytic virus is a conditionally replicating adenovirus (CRAd). The oncolytic virus can replicate under the control of different promoters such as survivin promoter, which is highly expressed only in a subpopulation of tumor cells, and the Secreted Protein Acidic Rich in Cysteine (SPARC) promoter, which is overexpressed in both tumor and tumor-associated stromal cells. In some embodiments, the oncolytic adenovirus is AR2011. In some embodiments, AR2011 replicates under the control of SPARC promoter. In some embodiments, the virus is a CRAd driven by the surviving promoter such as CRAd-Survivin-pk7 or a CRAd driven by the SPARC promoter such as CRAd-SPARC-pk3/5 and CRAd-SPARC-pk7. In some embodiments, the CRAds disclosed herein further comprises enhancer elements that facilitate viral replication in response to hypoxia and inflammation, which are conditions commonly present in tumor microenvironments. In some embodiments, the NSC is from an NSC line HB1.F3.CD. In some embodiments, the NSC is clonal human neural stem cell line HB1.F3.CD21. In some embodiments, the cancer is an intraperitoneal cancer including but not limited to, peritoneal cancer, ovarian cancer, bladder cancer, pancreatic cancer, colorectal cancer, gastric cancer, and liver cancer. In some embodiments, the cancer is brain cancer. In some embodiments, the cancer is a metastatic cancer.

In a related aspect, disclosed herein is a pharmaceutical composition comprising a therapeutically effective amount of NSCs and an oncolytic adenovirus. In some embodiments, the ratio of NSCs to the oncolytic adenovirus is about 100:1, about 200:1, about 300:1, about 400:1, about 500:1, about 600:1, about 700:1, about 800:1, about 900:1, about 1000:1, about 1100:1, about 1200:1, about 1300:1, about 1400:1, about 1500:1, about 1600:1, about 1700:1, about 1800:1, about 1900:1, or about 2000:1. In some embodiments, the NSCs are transduced with the oncolytic adenovirus. In some embodiments, the oncolytic virus belongs to adenovirus subtype 5 (Ad5). In some embodiments, the oncolytic virus is a conditionally replicating adenovirus (CRAd). The oncolytic virus can replicate under the control of different promoters such as survivin promoter, which is highly expressed only in a subpopulation of tumor cells, and the Secreted Protein Acidic Rich in Cysteine (SPARC) promoter, which is overexpressed in both tumor and tumor-associated stromal cells. In some embodiments, the oncolytic adenovirus is AR2011. In some embodiments, AR2011 replicates under the control of SPARC promoter. In some embodiments, the virus is a CRAd driven by the surviving promoter such as CRAd-Survivin-pk7 or a CRAd driven by the SPARC promoter such as CRAd-SPARC-pk3/5 and CRAd-SPARC-pk7. In some embodiments, the CRAds disclosed herein further comprises enhancer elements that facilitate viral replication in response to hypoxia and inflammation, which are conditions commonly present in tumor microenvironments. In some embodiments, the NSC is from an NSC line HB1.F3.CD. In some embodiments, the NSC is clonal human NSC line HB1.F3.CD21. In some embodiments, the pharmaceutical composition further comprises a therapeutically effective amount of one or more immune checkpoint inhibitors including but not limited to inhibitors for B7-1, B7-2, PD-1, PD-L1, PD-L2, CTLA-4, CD40, CD40L, CD47, CD48, CD244, CD80, CD86, CD155, IDO, CDK-12, Galectin-9, LAG-3, TIM-3, VISTA, TIGIT, SIRPα. The inhibitors can be small molecules, antibodies, minibodies, diabodies, triabodies, nanobodies, single domain antibodies. For example, a PD-L1 inhibitor such as a PD-L1 antibody or an shRNA against PD-L1 can be used. Alternatively, the inhibitors can be inactive "bait" proteins which compete to bind and displace checkpoint receptors, their ligands, and signaling molecules such as SIRPα. In some embodiments, the pharmaceutical composition further comprises a therapeutically effective amount of a chemotherapeutic agent such as cisplatin. In some embodiments, the pharmaceutical composition further comprises one or more pharmaceutically acceptable carriers or excipients.

In another aspect, provided herein is a method of treating cancer with a combination of oncolytic virotherapy and immune modulation. The method entails administrating to a subject a pharmaceutical composition comprising NSCs packaged or transduced with one or more immunomodulatory viruses expressing one or more immunity checkpoint inhibitors, including adaptive immunity checkpoint inhibitors and innate immunity checkpoint inhibitors. The one or more immune checkpoint inhibitors include but are not limited to inhibitors for B7-1, B7-2, PD-1, PD-L1, PD-L2, CTLA-4, CD40, CD40L, CD47, CD48, CD244, CD80, CD86, CD155, IDO, CDK-12, Galectin-9, LAG-3, TIM-3, VISTA, TIGIT, SIRPα. The inhibitors can be small molecules, antibodies, minibodies, diabodies, triabodies, nanobodies, single domain antibodies. For example, a PD-L1 inhibitor such as a PD-L1 antibody or an shRNA against PD-L1 can be used. Alternatively, the inhibitors can be inactive "bait" proteins which compete to bind and displace checkpoint receptors, their ligands, and signaling molecules such as SIRPα. In some embodiments, the immunity checkpoint inhibitors are shRNAs against the immunity checkpoint proteins. In some embodiments, the cancer includes but is not limited to primary, recurrent, and metastatic brain cancer, breast cancer, head and neck cancer, bladder cancer, ovarian cancer, uterine cancer, prostate cancer, skin cancer, lung cancer, and colorectal cancer. In some embodiments, the cancer is an intraperitoneal cancer capable of being treated via intraperitoneal (IP) injection including but not limited to, peritoneal cancer, ovarian cancer, bladder cancer, pancreatic cancer, colorectal cancer, gastric cancer, and liver cancer. In some embodiments, the cancer is brain cancer. In some embodiments, the cancer is a metastatic cancer. In some embodiments, the NSCs are human NSCs packaged or transduced with an adenovirus (e.g., CRAd-Survivin-pk7 adenovirus, CRAd-SPARC-pk7 adenovirus, or CRAd-SPARC-pk3/5 adenovirus) expressing an adaptive immunity checkpoint inhibitor (e.g., shRNA against PD-L1) and an innate immunity checkpoint inhibitor (e.g., shRNA against CD47). In some embodiments, the NSCs are administered to a subject by injection, e.g., by intraperitoneal (IP) injection. In some embodiments, the NSC is from an NSC line HB1.F3.CD. In some embodiments, the NSC is clonal human NSC line HB1.F3.CD21.

In another aspect, provided herein are NSCs packaged or transduced with one or more immunomodulatory viruses expressing one or more immune system checkpoint inhibitors for treating cancer. In some embodiments, the immune system checkpoint inhibitors include adaptive immune system checkpoint inhibitors and innate immune system checkpoint inhibitors. The one or more immune checkpoint inhibitors include but are not limited to inhibitors for B7-1, B7-2, PD-1, PD-L1, PD-L2, CTLA-4, CD40, CD40L, CD47, CD48, CD244, CD80, CD86, CD155, IDO, CDK-12, Galectin-9, LAG-3, TIM-3, VISTA, TIGIT, SIRPα. The inhibitors can be small molecules, antibodies, minibodies, diabodies, triabodies, nanobodies, single domain antibodies. For example, a PD-L1 inhibitor such as a PD-L1 antibody or an shRNA against PD-L1 can be used. Alternatively, the inhibitors can be inactive "bait" proteins which compete to bind and displace checkpoint receptors, their ligands, and signaling molecules such as SIRPα. In some embodiments, the immune system checkpoint inhibitors are shRNAs against the immune system checkpoint proteins. In some embodiments, the cancer includes but is not limited to primary, recurrent, and metastatic brain cancer, breast cancer, head and neck cancer, bladder cancer, ovarian cancer, uterine cancer, prostate cancer, skin cancer, lung cancer, and colorectal cancer. In some embodiments, the cancer is an intraperitoneal cancer capable of being treated via intraperitoneal (IP) injection including but not limited to, peritoneal cancer, ovarian cancer, bladder cancer, pancreatic cancer, colorectal cancer, gastric cancer, and liver cancer. In some embodiments, the cancer is metastatic ovarian cancer. In some embodiments, the cancer is brain cancer. In some embodiments, the NSCs are human NSCs packaged or transduced with an adenovirus (e.g., CRAd-Survivin-pk7 adenovirus, CRAd-SPARC-pk7 adenovirus, or CRAd-SPARC-pk3/5 adenovirus) expressing an adaptive immunity checkpoint inhibitor (e.g., shRNA against PD-L1) and an innate immunity checkpoint inhibitor (e.g., shRNA against CD47). In some embodiments, the NSC is from an NSC line HB1.F3.CD. In some embodiments, the NSC is clonal human NSC line HB1.F3.CD21.

In another aspect, disclosed herein is a pharmaceutical composition for treating cancer comprising a therapeutically effective amount of NSCs packaged or transduced with one or more immunomodulatory viruses expressing one or more immune system checkpoint inhibitors. In some embodiments, the NSCs are human NSCs. In some embodiments, the NSC is from an NSC line HB1.F3.CD. In some embodiments, the NSC is clonal human NSC line HB1.F3.CD21. In some embodiments, the immune system checkpoint inhibitors include adaptive immune system checkpoint inhibitors and innate immune system checkpoint inhibitors. The one or more immune checkpoint inhibitors include but are not limited to inhibitors for B7-1, B7-2, PD-1, PD-L1, PD-L2, CTLA-4, CD40, CD40L, CD47, CD48, CD244, CD80, CD86, CD155, IDO, CDK-12, Galectin-9, LAG-3, TIM-3, VISTA, TIGIT, SIRPα. The inhibitors can be small molecules, antibodies, minibodies, diabodies, triabodies, nanobodies, single domain antibodies. For example, a PD-L1 inhibitor such as a PD-L1 antibody or an shRNA against PD-L1 can be used. Alternatively, the inhibitors can be inactive "bait" proteins which compete to bind and displace checkpoint receptors, their ligands, and signaling molecules such as SIRPα. In some embodiments, the immune system checkpoint inhibitors are shRNAs against the immune system checkpoint proteins. In some embodiments, the cancer includes but is not limited to primary, recurrent, and metastatic brain cancer, breast cancer, head and neck cancer, bladder cancer, ovarian cancer, uterine cancer, prostate cancer, skin cancer, lung cancer, and colorectal cancer. In some embodiments, the cancer is an intraperitoneal cancer capable of being treated via intraperitoneal (IP) injection including but not limited to, peritoneal cancer, ovarian cancer, bladder cancer, pancreatic cancer, colorectal cancer, gastric cancer, and liver cancer. In some embodiments, the cancer is metastatic ovarian cancer. In some embodiments, the cancer is brain cancer. In some embodiments, the NSCs are human NSCs packaged or transduced with an adenovirus (e.g., CRAd-Survivin-pk7 adenovirus, CRAd-SPARC-pk7 adenovirus, or CRAd-SPARC-pk3/5 adenovirus) expressing an adaptive immunity checkpoint inhibitor (e.g., shRNA against PD-L1) and an innate immunity checkpoint inhibitor (e.g., shRNA against CD47). In some embodiments, the pharmaceutical composition is formulated as an injectable formulation, such as a formulation for intraperitoneal (IP) injection. In some embodiments, the pharmaceutical composition further comprises one or more pharmaceutically acceptable excipients, carriers, preservatives, diluent, buffer, or a combination thereof.

In yet another aspect, provided herein is a combinational therapy for cancer. The therapy comprises performing surgery, administering one or more of chemotherapeutic agents, administering one or more radiotherapies, and/or administering one or more of immunotherapies to a subject in need thereof before, during, or after administering the NSCs-mediated oncolytic viral therapy disclosed herein. In some embodiments, the surgery, chemotherapy, radiotherapy, and/or immunotherapy is performed or administered to the subject after administering the NSCs-mediated oncolytic viral therapy disclosed herein.

BRIEF DESCRIPTION OF THE DRAWINGS

This application contains at least one drawing executed in color. Copies of this application with color drawing(s) will be provided by the Office upon request and payment of the necessary fees.

FIGS. 14A-14E show CRAd-Survivin-pk7 NSCs combination with cisplatin (orthotopic model). (A) PCR analysis for hexon (upper panel, indicates presence of virus) and v-myc (center panel, indicates presence of NSCs) in ovarian tumor metastases isolated 2 days post-NSC.CRAd-Survivin-pk7 administration. GAPDH is shown as loading control. (B and C) NSC.CRAd-Survivin-pk7 is effective against orthotopic ovarian cancer. (B) Bioluminescence images acquired on 11 days after tumor injection (post-treatment 1) to visualize tumor burden (orthotopic NSG: OVCAR8 model). (C) Quantitative representation of luminescent flux signal presented as the percent change in tumor flux signal from 5 days after tumor injection (pre-treatment) to 5 days after treatment round 1 (gray bars) and treatment round 2 (black bars). Error bars represent the SD. (D) Average percent change in mouse weight ±SEM for each treatment group. PBS (black), NSC-CRAd-Survivin-pk7 (blue), cisplatin (green), combination (red). (E) Statistical analysis of clinical observation score pairwise comparisons acquired during treatment and 4 weeks afterward. Maximum daily score reflects the worst toxicity each mouse experienced after scoring for clinical symptoms, and early max score represents the earliest day each mouse reached its maximum daily score.

FIGS. 16A-16D show established clinical-grade NSC.CRAd production and characterization SOPs. One advantage of using an allogeneic clonal NSC line for oncoviral delivery is that viral transduction (A, B) and lysis kinetics (C) are highly reproducible. (A) Flow cytometric quantification of hexon-positive NSCs after transduction (MOI=50). (B) PCR quantification assay used to approximate viral load within NSCs transduced with CRAd-Survivin and CRAd-SPARC. Lysis and Tropism Kinetics (C-D). (C) Software-automated quantification of phase-object confluency in each well (average of 4 wells shown) demonstrating initial seeding and growth of NSCs (+/−CRAd infection). (D) ICP-MS quantification of AuNR levels within both ovarian metastases and IP lavage fluid over the course of 72 hours after IP administration of $10^6$ AuNR-labeled NSCs into tumor-bearing nude mice.

FIGS. 19A-19B show murine (GL261) and human (U251, PBT017) glioma line treated with CRAd-Survivin or CRAd-SPARC. 10,000 tumor cells were plated 24 hours prior to virus treatments at MOI=10 and imaged every 4 hours post-treatment for 5 days. (A) Representative brightfield images after 4 days. (B) Normalized tumor cell quantification over time. X-axis and legend apply to all graphs.

FIGS. 23A-23B show murine (ID8) and human ovarian (OVCAR8, SKOV3) lines treated with CRAd-Survivin or CRAd-SPARC. 10,000 tumor cells were plated 24 hours prior to virus treatments at MOI=10 and imaged every 4 hours post-treatment for 5 days. (A) Representative brightfield images after 4 days. (B) Normalized tumor cell quantification over time. X-axis and legend apply to all graphs.

FIGS. 24A-24C show the in vivo efficacy of NSC.CRAds in pre-immunized mouse models. Mice were pre-immunized with two prior weekly treatments of free CRAd or NSC.CRAds respectively. Peritoneal metastases were established in mice 3 weeks prior to treatment. Tumor engraftment was confirmed by BLI. (A) Normalized viral load injected and in tumor with respect to PBS. (B) Omental tumor weight was determined after 3 rounds of treatment with free CRAd-Survivin or NSC.CRAd-Survivin; each point indicates an individual mouse. (C) Ascites volume was determined after 3 rounds of treatment with free CRAd-SPARC or NSC.CRAd-SPARC; each point indicates an individual mouse.

DETAILED DESCRIPTION

Figure 1:
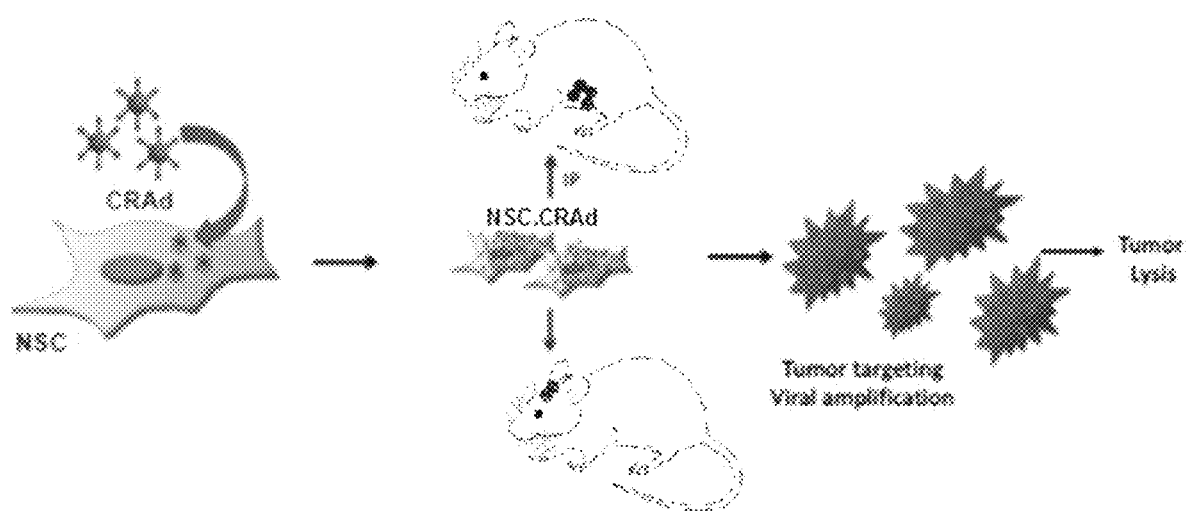
FIG. 1 illustrates an example of the therapeutic schematic of cancer therapy. NSCs are transduced with CRAds and frozen into aliquots that are thawed and rinsed just prior to administration per clinical SOPs. NSC.CRAds are then injected into tumor-bearing mice. NSCs efficiently deliver the CRAds to tumor foci. CRAds propagate through the tumor, lysing malignant cells and exposing new tumor antigens to stimulate a secondary anti-tumor immune response.

Methods for treating cancer using tropic cells (e.g., stem cells or neural stem cells (NSCs)) in combination with an oncolytic adenovirus or using tropic cells such as NSCs that carry a modified oncolytic virus expressing one or more immune system checkpoint inhibitors are provided herein. Such methods may be used to treat any cancer or tumor cell type including, but not limited to those related to primary, recurrent, and metastatic brain cancer, breast cancer, head and neck cancer, bladder cancer, ovarian cancer, uterine cancer, prostate cancer, skin cancer, lung cancer, and colorectal cancer. In some embodiments, the cancer is an intraperitoneal cancer capable of being treated via intraperitoneal (IP) injection including but not limited to, peritoneal cancer, ovarian cancer, bladder cancer, pancreatic cancer, colorectal cancer, gastric cancer, and liver cancer. In some embodiments, the cancer is brain cancer. In some embodiments, the cancer is a metastatic cancer.

Oncolytic virotherapy is a promising novel approach that can induce cancer cell death irrespective of radio- or chemoresistance, and also stimulate immune system recognition of cancer cells by exposing tumor antigens upon lysis. Although clinical trials to date have demonstrated safety, the efficacy of this approach has been limited by delivery hurdles including rapid inactivation by the immune system, poor viral penetration of tumors, and an inability of the virus to effectively reach invasive metastatic foci separated by normal tissue. Inherently tumor-tropic NSCs have the ability to penetration metastases, making them an ideal cell carrier to overcome these hurdles. In particular, the clonal human NSC line used in this disclosure, HB1.F3.CD21, enables reproducible viral loading, non-immunogenicity, and chromosomal stability, with demonstrated clinical safety in first-in-human brain tumor trials. NSC distribution to peritoneal ovarian metastases was previously reported in an immunodeficient model. Demonstrated in this disclosure is NSC distribution to intraperitoneal (IP) ID8.Renilla.eGFP ovarian cancer metastases in a C59131/6 immunocompetent mouse model. Their ability to provide protection from immune-mediated viral clearance and neutralization while selectively delivering oncolytic viruses to ovarian tumor foci is assessed.

In some embodiments, the oncolytic virus belongs to adenovirus subtype 5 (Ad5). In some embodiments, the oncolytic virus is a conditionally replicating adenovirus (CRAd). The oncolytic virus can replicate under the control of different promoters such as survivin promoter, which is highly expressed only in a subpopulation of tumor cells, and the Secreted Protein Acidic Rich in Cysteine (SPARC) promoter, which is overexpressed in both tumor and tumor-associated stromal cells. Selecting different promoters can optimize the level of expression in different types of cells, thereby to target different types of cancer or cancer microenvironment. Moreover, the adenovirus is modified by including different virus fibers such as pk7 and pk3/5, which determine which cells the virus can enter.

In some embodiments, the oncolytic adenovirus is AR2011. In some embodiments, AR2011 replicates under the control of SPARC promoter. In some embodiments, the virus is a CRAd driven by the surviving promoter such as CRAd-Survivin-pk7 or a CRAd driven by the SPARC promoter such as CRAd-SPARC-pk3/5 and CRAd-SPARC-pk7. In some embodiments, the CRAds disclosed herein further comprises enhancer elements that facilitate viral replication in response to hypoxia and inflammation, which are conditions commonly present in tumor microenvironments.

In some embodiments, the oncolytic adenovirus used herein, AR2011, replicates under the control of the Secreted Protein Acidic Rich in Cysteine (SPARC) promoter. SPARC is overexpressed not only in tumor cells, but also in tumor-associated stroma, enabling efficient viral spread throughout the tumor and its microenvironment. AR2011 also contains enhancer elements that respond to tumor conditions of hypoxia and inflammation. Significant tumor killing of ID8 ovarian cancer cells was observed in vitro after 5 days of co-culture with NSC AR2011 (at a ratio of 1000:1). NSCs also protected the oncolytic activity of AR2011 when cultured in the presence of ovarian cancer patient ascites fluid, which was confirmed to have neutralizing antibodies against adenovirus. For in vivo NSC biodistribution studies, NSC.qtracker 605, or NSC.qtracker 655 were injected IP. Two days later, 3D block-face cryo-images of harvested mice were created to visualize NSC biodistribution. For oncoviral efficacy studies, $5 \times 10^6$ of either NSC.AR2011 or free AR2011 were administered IP weekly for 3 weeks, with cisplatin and no treatment controls, and followed for long-term survival, monitoring tumor progression with serial BLI. In vivo results demonstrate IP NSC.AR2011 seeding of virus at the majority of established ovarian tumor metastases. Viral distribution was confirmed via IHC and qPCR. Comparative in vivo efficacy studies are performed with and without a PD-L1 checkpoint inhibitor to potentially enhance the oncolytic virotherapy with an additional immune component. NCS-mediated AR2011 treatment with or without PD-L1 antibody to improve long-term survival as compared to standard of care chemotherapy regimens, without the associated off-target toxicities. The combination of NSCs and the oncolytic virus can be used to treat subjects suffering from ovarian cancer, particularly stage III ovarian cancer.

The cancer therapy disclosed herein helps the immune system recognize a particular type of tumor cells through inhibition of the mechanism that helped tumor cells hide from the immune system. By packaging this therapeutic approach in a tumor specific manner, the typical development of autoimmune disorders associated with antibody therapy strategies can be avoided. This is achieved by preventing shRNA delivery into normal tissue, as the NSC virotherapy disclosed herein does not invade normal tissue. Thus, this novel approach prevents potential autoimmunity caused by other available checkpoint inhibition therapy (Chen et al., 2015).

The method disclosed herein entails combining oncolytic virotherapy with immune modulation as a dual modality form of therapy against cancer, particularly metastatic cancer, e.g., metastatic ovarian cancer. In some embodiments, CRAd-Survivin-pk7 adenovirus is armed to express shRNA against PD-L1 (adaptive immunity checkpoint) and CD47 (innate immunity checkpoint) both individually and in combination. These immunomodulatory viruses are packaged into NSCs such as Karen Aboody's GMP grade human neural stem cells (hNSCs) for delivery to metastatic tumor sites via intraperitoneal (IP) injection. PD-L1 and CD47 shRNA expressing virotherapy delivered by NSCs IP is intended for tumor clearance of metastatic ovarian cancer. This form of combination therapy has the potential to lead to improved clinical outcome for metastatic ovarian cancer patients. Prognosis with standard therapy is at a 30% 5-year survival rate with debilitating side-effects that often lead patients to have to abandon treatment all together (Jemal et al., 2008; Li et al., 2012; and Cannistra, 2004). Not only is this method applicable to metastatic ovarian cancer, but also, other intraperitoneal cancers. Virotherapy addresses the hurdle of chemo resistant cancers no longer responding to standard treatment. However, this therapy has its own hurdles due to neutralizing antibodies from the immune system and poor delivery into distant metastatic tumor sites and the potential for toxicity from the virus itself (Mader et al., 2009). These hurdles can be overcome by using NSCs to deliver the virus, protecting it from the antibodies, and distributing it to all tumor sites. NSC virotherapy alone does not appear to clear tumor but only prevents tumor progression.

This combined form of therapy helps the immune system recognize tumor cells through shRNA inhibition of immune checkpoints expressed on tumor cells only by delivering the shRNA within the NSC virotherapy. This novel approach prevents potential autoimmunity caused by other available checkpoint inhibition therapy (Chen et al., 2015). This is achieved by preventing shRNA delivery into normal tissue, as the NSC virotherapy disclosed herein does not invade normal tissue. The potential for clinical impact goes beyond metastatic ovarian cancer and can be a safer, more effective standard of therapy for many forms of cancer.

HB1.F3.CD Neural Stem Cells (NSCs) exhibit inherent tropism to cancer including primary and metastatic tumor cells. NSC tropism can be exploited to selectively deliver therapeutic agents to tumor sites. For example, NSCs expressing cytosine deaminase (CD) have been used in the treatment of human glioblastoma brain cancer patients. NSCs expressing CRAd-Survivin-pk7 adenovirus have been used in the treatment of glioblastoma brain cancers in pre-clinical animal studies. Disclosed herein are HB1.F3.CD NSCs carrying CRAd-Survivin-pk7 adenovirus in turn carrying one or more shRNA constructs to specifically infect tumor cells in turn causing the targeted tumor cells to express shRNA against PD-L1 (adaptive immunity checkpoint) and/or shRNA against CD47 (innate immunity checkpoint). These novel NSCs delivering one or more checkpoint inhibitors can be used as a combination therapy injected intraperitoneally in the treatment of metastatic ovarian cancer. This novel combination therapy (1) protects the viruses from being rendered ineffective by naturally occurring neutralizing antibodies, (2) ensures effective targeting of all tumor sites, and (3) prevents undesired off target effects including toxicity due to autoimmune effects. This novel combination therapy will enable the immune system to recognize and destroy cancer tumor cells.

Conditionally replication-competent oncolytic virotherapy offers a new, highly promising approach for treating cancer such as ovarian cancer. Once seeded into the tumor, the oncolytic virus (OV) can selectively replicate in tumor cells to destroy them in situ via direct lysis (Jemal et al., 2008). The lysed cells free additional OV particles that will continue to infect neighboring tumor cells, amplifying their anti-neoplastic effect until normal tissue is reached, which causes OV replication to cease (Mader et al., 2009). Important for treating cancers that develop chemo-resistance, OVs can be engineered to exploit common mechanisms of resistance (Hartkopf et al., 2012), and can also stimulate immune recognition of cancer cells (Ahmed et al., 2013), due to exposure of tumor antigens upon apoptosis/lysis. Clinical trials have demonstrated the safety of OVs (Heise et al., 2000), but efficacy of this approach has been limited by immune inactivation that is induced shortly after injection (Ahmed et al., 2013).

CRAds have naturally evolved to be the preferred safe-harbors of immunologically cold tumor micro-environment, and are further genetically engineered to be both transductionally and transcriptionally tumor selective. Oncolytic viruses have the ability to induce oncolytic (immunogenic) cancer cell death irrespective of radio- or chemo-resistance and therefore, are effective on recurrent tumors. Oncolytic viruses also can stimulate secondary immune response by the release of pathogen-associated molecular patterns (PAMPs), damage-associate molecular patterns (DAMPs), and tumor-associated antigens (TAAs). However, there are hurdles in oncolytic virus (Ad5) delivery. For example, inefficient tumor localization due to rapid clearance from the IP cavity and immune inactivation by blood cells, complements (e.g. higher affinity for human coagulation factor X), antibodies, antiviral cytokines, and nonspecific uptake by tissue-resident macrophages (e.g. Kuppfer cells of the liver); inefficient tumor transduction due to reliance entry receptors (coxsackievirus and adenovirus receptors; CAR) expressed at low levels on ovarian cancer cells and downregulated on glioma cells; and poor viral spread throughout the dense tumor stroma and the tumor microenvironment.

This disclosure demonstrates that improved treatment outcomes are possible if the suppressive immune inactivation of OV can be mitigated. OV cargo can be protected from neutralizing antibodies by employing a cell-delivery vehicle (HB1.F3.CD tumor-tropic neural stem cells (NSCs)), and the OV itself can be armed with shRNA against immune checkpoints PD-L1 and CD47, so that T cells are better able to recognize tumor antigens. This is consistent with recent literature showing chemotherapy induces adaptive (PD-L1) and innate (CD47) immune regulators (Casey et al., 2016). Blocking their function using systemically administered small molecule drugs has allowed more effective anti-tumor immune responses, and has thus generated much excitement (Duraiswamy et al., 2013; and Gaillard et al., 2016). However, immune markers are also present on normal tissues, and systemic inhibition can lead to autoimmune disorders (Kong et al., 2014; Willingham et al., 2012; and Chen et al., 2015). Therefore, blocking their expression with an OV that is targeted specifically to tumor cells can eliminate these undesirable side-effects. While any OV can be used, disclosed herein as an example is a CRAd-Survivin-pk7 oncolytic adenovirus, which is replication-competent only in cells that over-express the survivin gene. Survivin is over-expressed in 73% of ovarian cancer patients but not in normal cells; therefore, this promoter affords tumor selectivity (Sah et al., 2006; Liguang et al., 2007). The therapeutic OV is further protected from neutralizing antibodies using the clinically safe, tumor-tropic HB1.F3.CD NSC line. The preliminary data shows this NSC line demonstrates remarkable tropism for ovarian metastases, even when loaded with an OV. Accordingly, an innovative therapy that improves clinical outcomes for patients suffering from metastatic cancer, such as metastatic ovarian cancer, can be developed.

Despite decades of research efforts, ovarian cancer continues to be the most lethal of gynecologic malignancies: Every day, 60 American women are diagnosed with ovarian cancer, (equating to nearly 22,000 per year) (Cannistra, 2004). This cancer has an exceptionally high mortality rate, largely because the majority (75%) of patients present at an advanced stage (stage III), with widespread metastatic disease within the peritoneal cavity (Jemal et al., 2008; and Li et al., 2012). The median overall survival for these patients is less than three years following standard treatment of intravenous or intraperitoneal (IP) administered combination chemotherapy (e.g., cisplatin and paclitaxel) (Vasey et al., 2002) with or without surgical debulking. Quality of life for patients undergoing chemotherapy is poor, and associated with such debilitating toxic side effects that most patients are unable to complete their treatment due to severe abdominal pain, nausea, and vomiting (Douglas et al., 2001; and Ulasov et al., 2007). The majority of women will develop chemo-resistance and succumb to their disease within a few years. This sobering clinical scenario underscores an urgent critical need for new, more effective therapies that can improve both quality of life and treatment outcomes for patients with drug refractory ovarian cancer. Disclosed herein is a method to improve ovarian cancer treatment options. This treatment combines the clinically relevant and safe tumor-tropic neural stem cell (NSC) line (e.g., HB1.F3.CD) with an oncolytic adenovirus (e.g., CRAd-Survivin-pk7) that is engineered to simultaneously: 1) replicate specifically in ovarian tumors that are most resistant to chemotherapy; and 2) overcome tumor-cell mediated immunosupression (see FIG. 1).

The cancer therapy disclosed herein is significant because it has the potential to both increase long-term survival for stage III ovarian cancer patients and reduce toxicities associated with current therapies for ovarian cancer. The proposed CRAd-Survivin-pk7 NSCs can serve as an effective stand-alone and/or adjuvant treatment that increases therapeutic index of current chemotherapeutic regimens. The expected improvement in patients' quality of life in addition to longevity is significant. Furthermore, although the disclosed cancer therapy uses ovarian metastases as an example, the platform is applicable for other types of peritoneal carcinomas, regardless of their anatomical origin. Additionally, this platform can also improve outcomes for other peripheral metastatic tumors that overexpress survivin (e.g., breast and lung cancers) which are responsible for 1 out of 4 cancer-related deaths.

In some embodiments, disclosed herein is a cancer therapy that will benefit women who have already developed chemo-resistance, in which survivin, PD-L1 and CD47 are up-regulated (Willingham et al., 2012; Chen et al., 2015; Mittal et al., 2013; Okazaki et al., 2007; and Zitvogel et al., 2012). NSCs are used to deliver an oncolytic virus engineered to replicate under the control of the survivin promoter and to express shRNA against specific immune checkpoint regulators. Programmed death ligand 1 (PD-L1) and CD47 immune checkpoints are targeted both individually and in combination. PD-L1 is an adaptive immune regulator that when up-regulated leads to inhibition of T cell proliferation, survival and effector functions (Okazaki et al., 2007). CD47 is an innate immune regulator expressed on native host cells, which binds to SIRPα and prevents phagocytosis by macrophages and dendritic cells (Willingham 2012). Both are upregulated in ovarian cancer, preventing an effective anti-tumor immune response (Casey et al., 2016). However, both are also expressed in normal tissues and systemic therapies to inhibit them can lead to autoimmune disorders (Casey et al., 2016; and Kong et al., 2014). The development of autoimmune diseases such as colitis, type I diabetes, hypophysitis, and thyroid dysfunction, among others, is commonly see with systemic immune checkpoint inhibition therapies (Kong et al., 2014; Ansari et al., 2003; and Joshi et al., 2016). Tumor selective NSC-OV delivery of shRNAs against PD-L1 and CD47 ensures inhibition only in tumor cells and not in normal cells, limiting autoimmune reactions. This dual-modality therapy is innovative, as using virus to deliver a therapeutic such as siRNA or shRNA is usually done with viral vectors, in which the virus itself no longer has a function, except as a vessel for delivery (Nayerossadat et al., 2012). The cancer therapy disclosed herein not only induces an immune response by blocking the expression of these immune checkpoints, but also allows the functional OV to replicate and achieve cell lysis.

In some embodiments, disclosed herein is a method of treating ovarian cancer. Although it was previously demonstrated that the HB1.F3.CD cell line can improve adenovirus delivery within the brain, it was not yet clear whether this approach would work in the peritoneal setting, which is less immune-privileged than the brain. As demonstrated in the working examples, the clinical-equivalent research lot of NSC.CRAd-Survivin-pk7 already developed for a glioma clinical trial (ClinicalTrials.gov: NCT03072134) was used to show that this well-characterized cell line can not only protect the CRAd-Survivin-pk7 from pre-existing neutralizing antibodies present in patient ascites, but also improve CRAd-Survivin-pk7 delivery and anti-tumor efficacy in orthotopic mouse models. This result is consistent with another study showing that MSCs carrying measles virus can home to ovarian tumor xenografts in passively immunized athymic mice and lead to a superior therapeutic outcome compared with virus alone.[60]

Also demonstrated in the working example is that NSC.CRAd-Survivin-pk7, in both the flank and the orthotopic settings, is as effective at slowing tumor progression as 4 mg/kg/week cisplatin (equivalent to human clinical dose), but without the measurable toxicities associated with this chemotherapeutic, including dose-dependent renal tubule toxicity and neurotoxicity.[61] Although the negligible toxicity due to NSC.CRAd-Survivin-pk7 observed in the study may simply be because of poor infection of mouse tissues by human adenovirus, it is also consistent with clinical trial data reported to date. Of the 11 oncolytic viruses that have been tested in preclinical human ovarian cancer models, 4 have been tested in 9 different phase I/II clinical trials. Although these clinical trials are still in early stages, they have all established the safety and nontoxicity of oncolytic virus-based approaches. In direct contrast with trials testing traditional chemotherapies, not a single oncolytic virus trial has established a maximum tolerated dose because toxicities are so low.

Surprisingly, the working examples demonstrated significant synergy for the CRAd-Survivin-pk7 and cisplatin combination in vitro, and confirmed the ability of this combination treatment to reduce tumor burden in both flank and orthotopic immunocompromised mice. This result is significant because including NSC.CRAd-Survivn-pk7 as an adjuvant treatment could increase the therapeutic index of cisplatin. RT-PCR analysis of survivin expression in OVCAR8 and SKOV3 cell lines treated with cisplatin demonstrated that surviving expression did not significantly increase after up to 2 days of cisplatin exposure (data not shown). This result is consistent with bioinformatics analysis of GEO Accession Viewer data on patient tumors showing no reliable increase in survivin expression after patient tumors become cisplatin resistant (FIG. 15).

Thus, this disclosure provides the first demonstration of the strong potential for oncoviral delivery using an off-the-shelf allogeneic cell line. Furthermore, disclosed herein is that the CRAd-Survivin-pk7 oncolytic adenovirus has impressive anti-tumor activity against stage III ovarian cancer, on par with results observed using the gold standard treatment, cisplatin. The working examples demonstrated the potential of combining cisplatin with NSC.CRAd-Survivin-pk7 to result in increased tumor killing than is possible with cisplatin alone. Upon further preclinical development using preimmunized immunocompetent mouse models, this system can be used to improve the delivery of therapeutic oncolytic adenoviruses within the peritoneal cavity.

CRAd-Survivin-pk7

Figure 2A:
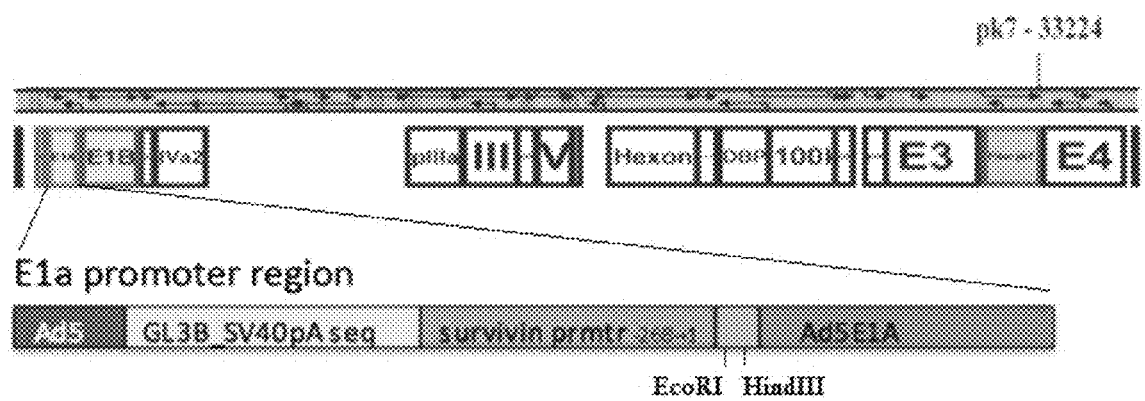
FIG. 2A is a diagram of CRAd-Survivin-pk7 genome. The native E1a promoter of Ad5 was replaced with a portion of the survivin promoter to direct tumor-selective virus replication. A short poly-lysine (pk7)-encoding sequence (60 bp) was incorporated into the gene encoding the fiber protein of the Ad. This modification improves the transduction efficiency of the virus in cells with limited numbers of CAR receptors. EcoRI and HindIII sites are available to recombine the commercially available shRNAs.
Figure 2B:
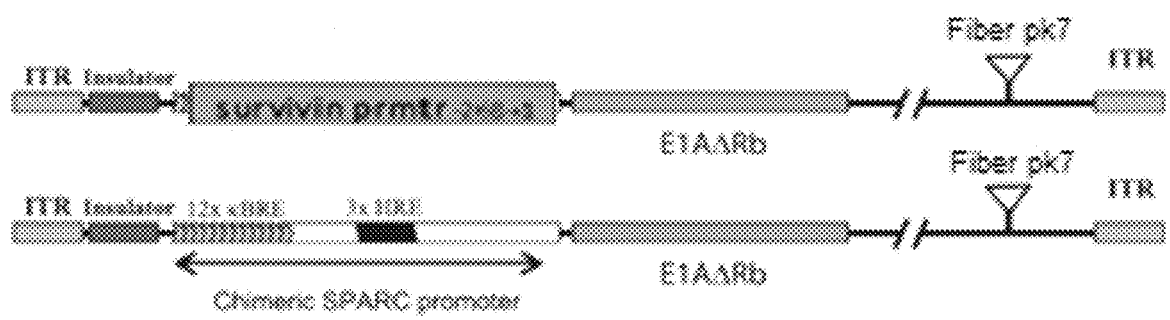
FIG. 2B shows that CRAd is engineered to replicate either in tumor cells that overexpress survivin or in stromal cells which overexpress SPARC.

More than 20 oncolytic viruses have been developed so far, and 11 have been tested in pre-clinical human ovarian cancer models (Li et al., 2012). To date, 4 of these 11 viruses have been tested in nine clinical trials (Li et al., 2012) that have all established the safety/non-toxicity of this approach (Jemal et al., 2008). In direct contrast to trials testing traditional chemotherapies, not a single oncolytic virus trial has established a maximum tolerated dose because toxicities are so low (Li et al., 2012). Although this demonstrates the safety of an oncolytic virotherapy approach, the challenge now is to achieve efficacy. The best clinical results so far have been observed with CRAd5 viruses, as based on the highest percentage of patients achieving stable disease, and at least 2 patients experiencing at least a partial response (Pesonen et al., 2011). For this reason, a particular CRAd virus engineered for efficacy against ovarian cancer is used herein as an example. As shown in FIG. 2, a novel CRAd virus is modified to replicate under the control of the survivin promoter (Ulasov et al., 2007), a protein that is selectively upregulated in about 6% of ovarian cancer patients prior to chemotherapy, but becomes upregulated in more than 85% of ovarian cancer patients that have developed chemo-resistance and are no longer responsive to chemotherapy (Nwanegbo et al., 2004). Alternatively, the CRAd virus is modified to be placed under the control of the SPARC promoter. This virus can be edited further to add the coding sequence of shRNAs against PD-L1 and CD47.
CRAd-SPARC-pk3/5

Previous studies showed that neural stem cells (NSCs) have inherent tropism to tumors, making them an ideal delivery vehicle. The NSC-delivered adenovirus, CRAd-Surivin-pk7, is protected from rapid immune-mediated clearance and neutralization, resulting in more effective distribution to tumors compared to free virus. This result was observed in immunodeficient and immunocompetent murine models of peritoneal ovarian metastases and orthotopic glioma. However, the therapeutic efficacy of the virus is limited by the survivin promoter, which is highly expressed only in a subpopulation of tumor cells. In contrast, CRAd-SPARC-pk3/5 replicates under the SPARC promoter, which is overexpressed in both tumor and tumor-associated stromal cells. In addition, CRAd-SPARC-pk3/5 contains enhancer elements that facilitate viral replication in response to hypoxia and inflammation, conditions commonly present in tumor microenvironments. Therefore, by targeting both the tumor and the tumor microenvironment, CRAd-SPARC-pk3/5 is more efficacious in certain cancer types, compared to CRAd-Surivin-pk7.

Figure 3A:
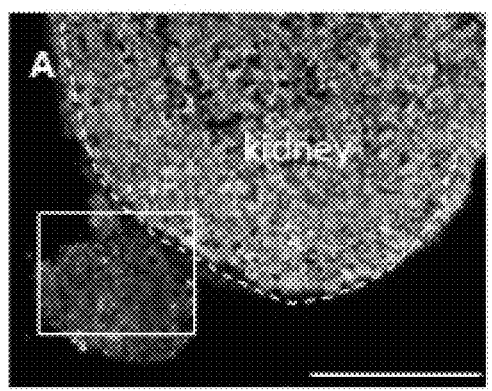
FIGS. 3A-3F illustrates NSCs as a tumor-tropic, immunoprotective OV delivery vehicle. A) IP-injected CRAd-Survivin-pk7 NSCs demonstrate selective tumor tropism in metastatic ovarian cancer model. DiI-labeled NSCs (red) were injected IP into mice with established ovarian metastases. (A-B) NSCs and (C-D) CRAd-Survivin-pk7 NSCs target and penetrate tumors within 24 hours, but not adjacent normal kidney (A, white dotted line) or intestine (C, white dotted line). Scale bar A, C=100 μm. Scale bar D=50 μm. Note: Kidney appears yellow due to autofluorescence. F) MLR measurement of degranulation in normal donor PBMCs in response to HB1.F3.CD NSCs. CE. Degranulation (a measure of potential immune response) of PBMCs was measured in the population of CD4+ and CD8+ cells in the presence of HB1.F3.CDs or PHA mitogen (positive control).
Figure 3B:
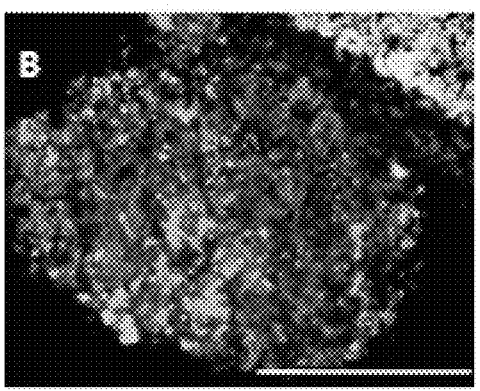
Figure 3C:
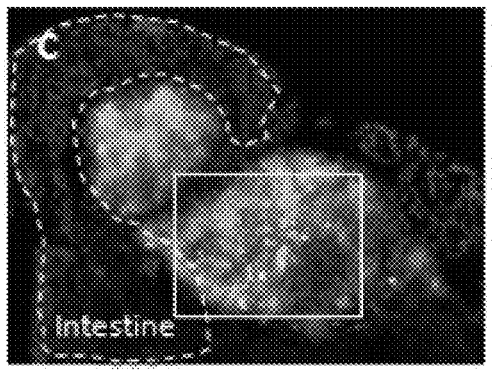
Figure 3D:
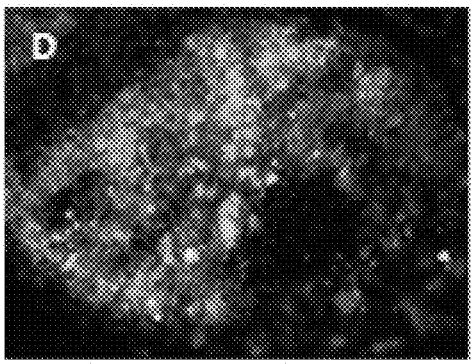
Figure 3E:
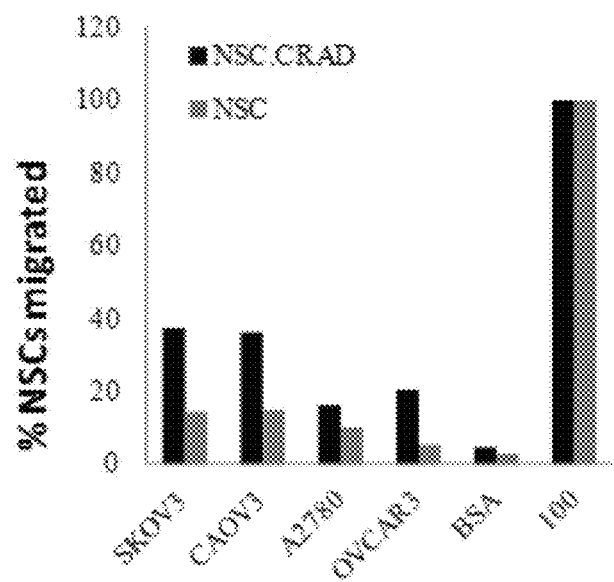
Figure 3F:
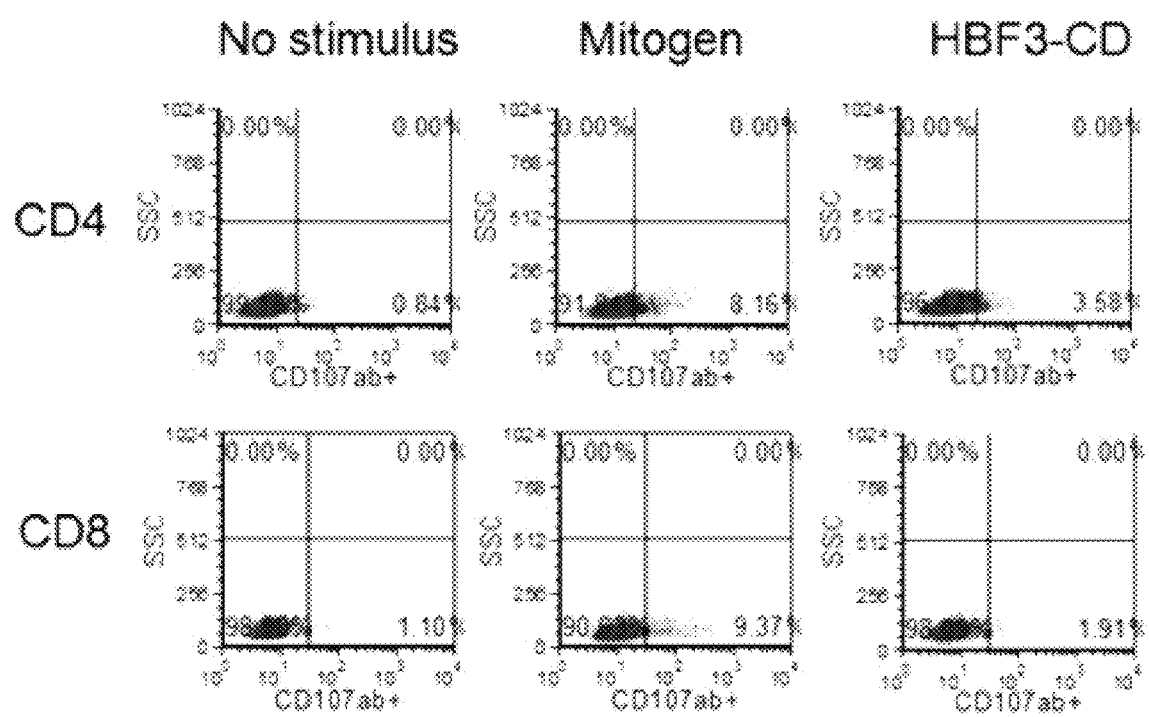

To compare the relative potencies of the same virus replicating under two different promoters, a fiber knob modification was performed on CRAd-SPARC-pk3/5 to create CRAd-SPARC-pk7. As demonstrated in the working examples, the viral uptake and lysis kinetics of NSCs carrying CRAd-SPARC-pk7 were optimized. CRAd-SPARC-pk7 was first examined in vitro using multiple murine and human glioma and ovarian tumor cell lines. Results demonstrated robust infection and significant tumor killing. In vivo efficacy studies are performed to compare NSC.CRAd-Survivin-pk7 vs. NSC.CRAd-SPARC-pk7 in immunodeficient and immunocompetent murine orthotopic tumor models. Thus far, it has been observed that the NSC delivery of CRAd-SPARC-pk7 increased viral distribution and spread in tumors, tumor-associated stroma, and the tumor microenvironment. Ongoing experiments are carried out to demonstrate improved anti-tumor efficacy of CRAd-SPARC-pk7, resulting in prolonged long-term survival. The addition of immune checkpoint inhibitors can result in potential therapeutic enhancement. Thus, NSC-delivered CRAd-SPARC-pk7 can be used as an adjunct to standard regimens for the treatment of brain and ovarian cancers.
Neural Stem Cell (NSC)-Mediated OV Delivery In some embodiments, the disclosed cancer therapy can offer a "one-shot" cure, with the viral particles amplifying their anti-neoplastic effect until normal tissue is reached (Kim et al., 2015). The viral particles are susceptible to rapid inactivation and clearance before they are able to infect tumor cells, especially when administered in the peritoneal cavity (Joshi et al., 2016). To overcome this hurdle, protective viral delivery vehicles including passive nanoparticles or tumor-tropic stem cells are developed. So far, cell-mediated delivery of oncolytic viruses is the approach generating the most exciting results. For example, it was recently demonstrated in a peritoneal ovarian cancer model that an MSC cell delivery vehicle could enhance the efficacy of an oncolytic measles virus in pre-immunized mice from non-significant to double that of saline controls (Mader et al., 2013). Furthermore, it was demonstrated that HB1.F3.CD NSCs inherently express low levels of MHC Class I antigens and undetectable levels of MHC Class II antigens. They not only avoid stimulating T cells in a well-established immune tolerance assay called the mixed lymphocyte reaction (FIG. 3A) (Mickelson et al., 1996). This assay will be also used to confirm enhanced immunogenicity of tumor cells after treatment with immunomodulatory CRAd constructs. It was also demonstrated that these immunoprotective NSCs improved viral load, distribution, safety and long-term survival as compared to free virus in an orthotopic model of another tumor type that overexpresses survivin, glioma (Ahmed et al., 2013). While CRAd-Survivin-pk7 has never been tested for efficacy against ovarian cancer, strong preclinical data in orthotopic models of ovarian cancer shows that NSCs exhibit remarkable tropism to ovarian cancer metastases, even when loaded with a virus (FIG. 3F). Furthermore, NSCs are advantageous over patient-derived MSCs because they are scalable, demonstrate superior chromosomal stability, and exhibit consistent, predictable transduction efficiencies (Aboody et al., 2000; and Power et al., 2007).
Combinational Therapy The NSC-mediated oncolytic virus delivery can be used in combination with surgery, immunotherapy, radiotherapy, and/or chemotherapy to obtain improved or synergistic therapeutic effects. For example, surgery, chemotherapy, radiotherapy, and/or immunotherapy can be performed or administered before, during, or after the NSC-oncolytic virus administration. In particular, surgery, chemotherapy, radiotherapy, and/or immunotherapy can be performed or administered after the NSC-oncolytic virus administration. As one of ordinary skill in the art would understand, the chemotherapy, immunotherapy, radiotherapy, and/or the NSC-oncolytic virus therapy can be administered to a subject in need one or more times at the same or different doses, depending on the diagnosis and prognosis of the cancer. One skilled in the art would be able to combine one or more of these therapies in different orders to achieve the desired therapeutic results. For example, the working examples demonstrate that the combination of NSC-oncolytic virus and a chemotherapeutic agent, cisplatin, achieved synergist effects. Depending on the cancer type, various chemotherapeutic agents can be selected for use in combination with the NSC-oncolytic virus disclosed herein.

Additionally, one or more immune checkpoint inhibitors can be administered to the subject before, during, or after administration of the NSCs and the oncolytic adenovirus. For example, the NSCs disclosed herein can be packaged with one or more immunomodulatory viruses expressing one or more immunity checkpoint inhibitors. The one or more immune checkpoint inhibitors include but are not limited to inhibitors for B7-1, B7-2, PD-1, PD-L1, PD-L2, CTLA-4, CD40, CD40L, CD47, CD48, CD244, CD80, CD86, CD155, IDO, CDK-12, Galectin-9, LAG-3, TIM-3, VISTA, TIGIT, SIRPα. The inhibitors can be small molecules, antibodies, minibodies, diabodies, triabodies, nanobodies, single domain antibodies. For example, a PD-L1 inhibitor such as a PD-L1 antibody or an shRNA against PD-L1 can be used. Alternatively, the inhibitors can be inactive "bait" proteins which compete to bind and displace checkpoint receptors, their ligands, and signaling molecules such as SIRPα.

The following examples are intended to illustrate various embodiments of the invention. As such, the specific embodiments discussed are not to be construed as limitations on the scope of the invention. It will be apparent to one skilled in the art that various equivalents, changes, and modifications may be made without departing from the scope of invention, and it is understood that such equivalent embodiments are to be included herein. Further, all references cited in the disclosure are hereby incorporated by reference in their entirety, as if fully set forth herein.

EXAMPLES

Example 1: Generate CRAd-Survivin-Pk7 Constructs that Express shRNA Against Immune Checkpoints A series of modified virus expressing commercially available PD-L1 shRNA, CD47 shRNA are developed. These can be transduced into NSCs individually and in combination and tested in vitro and using a bilateral flank mouse model. The ability of the new immunomodulatory oncolytic virus to inhibit tumor immunosuppression and allow for an anti-tumor immune response is shown.

The preliminary studies demonstrate that injection of CRAd-Survivin-pk7 NSCs into immunodeficient mice leads to slowed tumor growth, but not to tumor regression. It remains unknown whether tumor regression is possible when this treatment is applied in the context of a functional immune system. The basal level of immune-stimulation after CRAd-Survivin-pk7 NSC treatment is characterized, and a candidate immunomodulatory CRAd-Survivin-pk7 constructs that will maximize the potential for this OV treatment to trigger an effective anti-tumor immune response is fabricated. It is demonstrated that tumor-specific suppression of PD-L1 and CD47 can result in a robust anti-tumor immune response. This will be assessed in vitro using degranulation assays, and in vivo using a bilateral flank tumor assay in immunocompetent mouse models. Thus, it is established that CRAd-Survivin-pk7 is able to trigger a systemic immune response. This example contributes new, fundamental data regarding the immunomodulatory potential of CRAd-Survivin-pk7 and a strategy to overcome any observed suppression.

Experimental Design: 1.1 Edit CRAd-Survivin-Pk7 DNA with Immunomodulatory shRNA

A series of shRNA containing viral vectors will be generated by homologous recombination to introduce shRNA sequences (see Table 1) into the parental CRAd-Survivin-pk7 genome (Zhu et al., 2004). These shRNA sequences were obtained commercially and were accompanied by a scrambled shRNA control sequence. Purified viral constructs can then be used to infect HEK 293 packaging cells and shRNA integration in individual plaques can be verified by PCR. Successful viral constructs can then be amplified in A549 cells, followed by cesium-gradient purification. Lastly, tumor cell lines can be transduced with corresponding shRNA CRAd-constructs (see Table 1) for 24 hours, then CD47 and PD-L1 suppression can be confirmed via western blot analysis accompanied by band density analysis. Positive controls in which protein suppression is achieved with pharmacological inhibitors to PD-L1 (atezolizumab) and CD47 (anti-CD47 blocking antibody) can also be performed. Each entry in Table 1 carries a different shRNA that can be used depending on the model and target.

TABLE 1

List of available shRNA containing retroviral vectors to be used.

| Target | Model | Company | SKU |
| --- | --- | --- | --- |
| Human CD47 | SKOV3/OVCAR8/Humanized mice | OriGene | TR305509 |
| Mouse CD47 | ID8/syngeneic mouse | OriGene | TF501123 |
| Human PD-L1 | SKOV3/OVCAR8/Humanized mice | OriGene | TG314098 |
| Mouse PD-L1 | ID8/syngeneic mouse | OriGene | TR503436 |

1.2 Confirm Unimpaired Oncolytic Activity of shRNA Viral Constructs

NSCs can be transduced with each viral construct (MOI=50, 2 hour), then co-cultured with ovarian tumor cell lines (OVCAR8, SKOV3 and ID8) at decreasing NSC:tumor cell ratios. On day 0, 1, 3, 7, and 14, cultures can be fixed and assessed for cell number using crystal violet staining/absorbance quantification. A second set of plates can also be analyzed for viral infectivity using DAPI for cell nuclei and Hexon-FITC antibody for viral particles. Biostatistical analysis of the crystal violet absorbance data can be performed using a one-way ANOVA using GraphPad Prism software.

1.3 Confirm shRNA Viral Constructs Enhance T Cell Stimulation

Ovarian tumor cell lines (OVCAR8, SKOV3 and ID8) can be treated with each viral construct (MOI=50, 2 hr), then cultured for 2 days to allow sufficient time for viral transgene expression, but not enough time for tumor cell lysis (~3-4 days required for lysis). A mixed-lymphocyte reaction can then be performed by co-culturing viral treated tumor cells ($2 \times 10^5$) with the same number of patient derived PBMCs cells in the presence of antibodies against CD107a/b. This marker is expressed on the surface of activated lymphocytes due to the degranulation-accompanied surface-localization of cytotoxic granules. As a positive control, PBMCs can be exposed to the mitogen phytohemagglutinin. After a 5-hour incubation, flow cytometry can be performed with compensation for non-viable cells and isotype controls. The fraction of CD107a/b positive cytotoxic T-lymphocytes (CD3+, CD8+), and T-helper lymphocytes (CD3+, CD4+) observed when PBMCs are exposed to immunomodulatory CRAd-treated tumor cells can be compared to that observed when tumor cells are treated with the parental viral construct. Positive controls in which protein suppression is achieved with pharmacological inhibitors to PD-L1 (atezolizumab) and CD47 (anti-CD47 blocking antibody) can also be performed.

1.4 Characterize Ability of Viral Constructs to Trigger a Local Vs. Systemic Cell Response A bilateral flank assay will be performed in a syngeneic mouse model (Minev et al., 2014; and Zamarin et al., 2014). In brief, 40 C57BL/6 mice can be inoculated with $5 \times 10^6$ ID8 (murine) ovarian cancer cells in the right and left flank. After tumors reach a diameter of 5 mm, mice can be randomized into treatment groups (n=8/group) and administered a single 100 µL injection into only the right flank tumor. Treatment groups as follows: 1) untransduced NSCs ($1 \times 10^6$); 2) parental CRAd-Survivin-pk7 NSCs ($1 \times 10^6$ NSC, $1 \times 10^8$ IU); 3) mshPD-L1_CRAd-Survivin-pk7 NSCs ($1 \times 10^6$ NSC, $1 \times 10^8$ IU); 4) shCD47_CRAd-Survivin-pk7 NSCs ($1\times10^6$ NSC, $1\times10^8$ IU); 5) shCD47_mshPD-L1_CRAd-Survivin-pk7 NSCs ($1\times10^6$ NSC, $2\times10^8$ IU). 10 days post treatment, tumor size can be measured (weight/caliper) then it can be dissociated and assessed for IFN-γ levels (ELISA), T cell infiltration (Flow cytometry) (Leng et al., 2008). Results obtained in syngeneic mice can be confirmed in humanized mice (n=3) using the most immunogenic human ovarian cancer line as determined in experiment 1.3.

It is expected that immunomodulatory shRNAs can be successfully incorporated into CRAd-Survivin-pk7 without impairing viral transduction or oncolytic capabilities. Further, tumor cells infected with modified constructs are expected to induce a more robust immune response compared to the parental CRAd-Survivin-pk7 virus in vitro. The immunomodulatory constructs can more effectively enhance an anti-tumor immune response in the right (locally administered) flank, as evidenced by enhanced T cell infiltration, elevated interferon gamma levels, and decreased tumor volume. The combination of CD47 and PD-L1 inhibition can trigger the most enhanced immune response. Regardless, the NSC viral construct and/or combination that triggers the largest immune response can be carried forward into the efficacy studies. While a baseline immune response can be expected in the untreated left flank, it is not expected the immunomodulatory constructs to alter this response. Rather there can be uninhibited immunosuppressive tumor cells in the left flank.

It is possible that incorporating the shRNA using the previous recombination method will not be successful. While this is highly unlikely, an alternative approach in which there is no need for enzymatic activity or ligase steps can be applied (He et al., 1998). The commercially available shRNA constructs can sufficiently suppress CD47 and PD-L1 in the tumor lines; if less than 60% suppression for CD47 or 80% suppression for PD-L1 is observed, new shRNA sequences can be designed and a more effective construct can be chosen. If the immunomodulatory CRAd-S-pk7 constructs exhibit decreased cytolytic ability, the experiments will still proceed given, the data showing that the cytolytic capability of this virus is not sufficient to achieve tumor regression, that it is more important to effectively trigger an anti-tumor immune response. If the immunomodulatory viruses do not enhance the baseline immune response in the flank setting, their ability to enhance an anti-tumor response in the IP setting will be assessed, given the robust immunosuppression known to occur in ovarian cancer metastases.

Example 2: Determine Therapeutic Efficacy and Anti-Cancer Immune Response of NSC-CRAd-Survivin-Pk7+/−Immunomodulatory shRNA In Vivo The therapeutic efficacy of the PD-L1 and CD47 expressing virus during IP NSC delivery to the non-shRNA expressing virus are compared to determine whether efficacy is increased and tumor is cleared using orthotopic xenograft and syngeneic mouse models.

The objective of this example is to establish pre-clinical data demonstrating that repeated rounds of NSC-mediated OV treatment significantly improve survival in an orthotopic model of mice bearing cisplatin-resistant tumors. It is tested to see whether NSC-mediated delivery of immunomodulatory CRAd-Survivin-pk7 is more effective than NSC-mediated delivery of the parental CRAd-Survivin-pk7. A standard Kaplan Meier survival comparison is used to provide information about the utility of this treatment in both immunodeficient and humanized mice. The rationale for this example is that successful completion of the proposed research will contribute new information regarding the potential efficacy of CRAd-Survivin-pk7 NSCs for treating ovarian cancer, and to what extent tumor cell immunosuppression needs to be mitigated in order to achieve this effect. When the proposed studies for this example have been completed, it is expected that a significant survival benefit will be observed for mice that received immunomodulatory CRAd-Survivin-pk7 NSC treatments.

Experimental Design

A long-term survival study can be performed in a syngeneic mouse model and a humanized mouse model. One week prior to CRAd-Survivin-pk7 NSC administration, 64 C57BL/6 mice can be inoculated with ID8 tumor cells IP as our syngeneic model. Treatment can begin once tumors reach 5 mm. Eight treatment groups (16 mice/group) include: 1) PBS (control), 2) CRAd-Survivin-pk7 NSCs ($1\times10^6$ NSCs~$1\times10^8$ IU)+atezolizumab (20 mg/kg (39))+anti-CD47 antibody (200 μg (40)) 3) CRAd-Survivin-pk7 NSCs ($1\times10^6$ NSCs~ $1\times10^8$ IU) 4) CRAd-Survivin-pk7 NSCs expressing mouse PD-L1 and CD47 shRNA ($1\times10^6$ NSCs~ $1\times10^8$ IU). Each group receives eight treatment rounds (1 IP injection/day for 5 days) every other week as determined in on the preliminary studies. This can be repeated with humanized mice inoculated with the most immunogenic tumor line as determined in Example 1. Humanized mice can be treated one week after tumor inoculation. Treatment at this time mirrors treatment stage III ovarian cancer patients after surgical debulking.

Biostatistical Analysis:

For this example, 16 mice per group are used. Four mice per group can be euthanized after 4 rounds of treatment for histopathological, viral distribution analysis (qPCR, viral titration), immune cell infiltration (flow cytometry), cytokine levels (ELISA), and PD-L1 and CD47 (western blot). The location and weight of visible tumors are recorded, then 5 tumors per mouse as well as a sample surrounding normal tissue are processed for each assay. Quantitative viral load assessments include qPCR measurements of hexon gene expression, and viral titrations performed using dissociated tumor lysates. Five more tumors per mouse can be used for dendritic and T cell infiltration monitoring by flow cytometry. Remaining tumors can be sectioned and stained for hexon, CD8, PD-L1 and CD47. Each comparison can be made using a two-tailed t-test ($p<0.05$) with linear mixed effects models to recognize inter-mouse variability. The remaining 12 mice per group can receive an additional 4 rounds of treatment and be followed for long-term survival. Numbers of mice are calculated to ensure sufficient statistical power to compare groups. A two-sided log rank test with 12 mice per group can have at least 80% power at a 0.05 significance level to detect a hazard ratio between the groups of approximately 0.05 when the proportion surviving in the control group is 0.10. The study is powered to observe maximal differences in survival between two groups. Multiple pairwise comparison adjustments can be made to Log Rank test p-values using Sidak adjustment.

It is expected that mice in group four will have the greatest survival rate. These results are expected in both models with only slight variations between models. This is because both models express and upregulate survivin, PD-L1 and CD47 (Willingham et al., 2012; and Zitvogel et al., 2012). Namely, group 2 mice are expected to lead PD-L1 and CD47 suppression in both normal and tumor tissue and group 4 mice are expected to only suppress these in tumor tissue when compared to no suppression in group 3. These results should lead to immune cell infiltration to PD-L1 and CD47 suppressed tissues. Using immune competent mice can show the need to incorporate the immune system within our NSC virotherapy to hasten efficacy and lead to tumor clearance, which is currently only being maintained by NSC virotherapy alone.

It is expected that treatment with the shRNA recombinant NSC virotherapy will have faster, more efficient results. However, it is possible that mice treated with pharmacological inhibitors will have negligible suppression of PD-L1 and CD47 in normal tissue and subsequent negligible T cell infiltration. This is unlikely due to the endogenous importance of these in preventing autoimmunity. Any modulation of these two markers should result in a T cell response against those cells. It is also possible that virotherapy can lead to lowered survivin expression on tumor cells in order to protect themselves from the virus. This can be circumvented by editing the virus to use a different type of entry marker, such as CD46, which is highly expressed in ovarian cancer (Hulin-Curtis et al., 2016). This, however, would likely lead to tumor cell apoptosis, as survivin maintains cell survival in the face of apoptosis signaling making it an unlikely scenario (Sah et al., 2006). In the event that the immune response using dual-inhibition of PD-L1 and CD47 is too robust, leading to a cytokine storm, individual inhibition groups can be tested.

Example 3: CRAd-Survivin-Pk7 NSCs Kill Ovarian Cancer Cells In Vitro

Figure 4A:
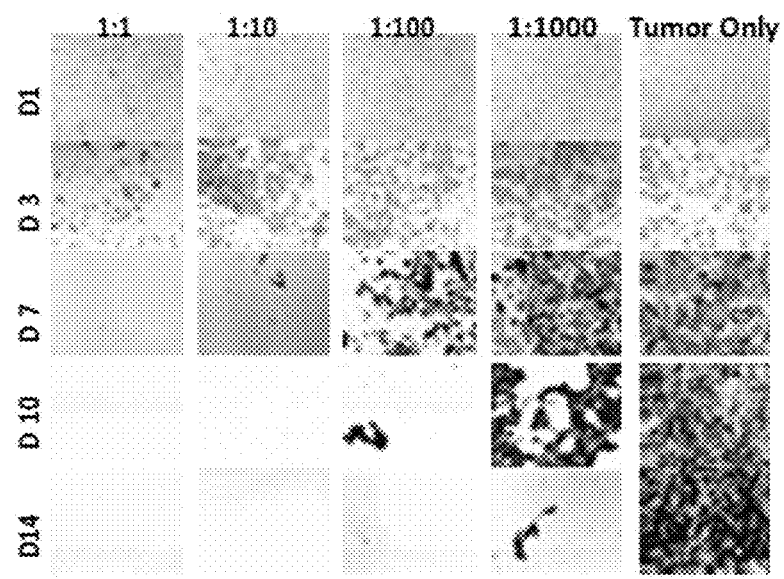
FIGS. 4A and 4B show CRAd-Survivin-pk7 NSCs in vitro efficacy. CRAd-Survivin-pk7 NSCs co-cultured with ovarian tumor cells eliminate tumor cells as indicated by (A) crystal violet stained culture wells, and (B) quantification of total viable cells in culture.
Figure 4B:
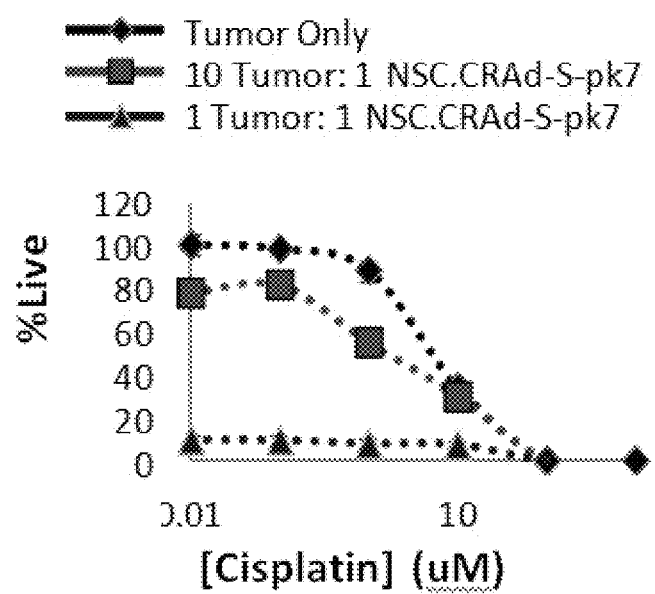

The following preliminary data confirm that CRAd-Survivin-pk7 progeny released from CRAd-Survivin-pk7 NSCs can effectively eliminate OVCAR8 tumor cells that are no longer responsive to patient-tolerable doses of cisplatin (FIG. 4B). In vitro co-culture of CRAd-Survivin-pk7 NSCs with OVCAR8 cancer cells resulted in the elimination of ovarian cancer cells in vitro, even at a tumor cell:NSC ratio of 1000:1 (FIG. 4A). While less efficient, this therapy also reduces the number of murine ID8 cells in culture (data not shown). Together, these results indicate that in the absence of immune-suppression, the virus can replicate within NSCs, infect neighboring tumor cells, and continue to amplify until the entire tumor cell culture has been killed. These results are consistent with well-established literature reports that ovarian cancer cells express high levels of both the coxsackievirus and adenovirus (CAR receptor) and survivin.

Figure 5A:
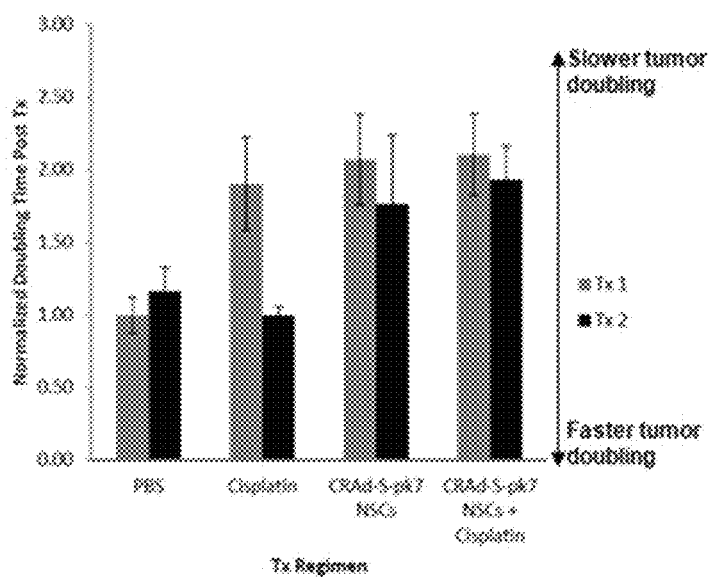
FIGS. 5A and 5B show that NSCs improve therapeutic efficacy of CRAd-Survivin-pk7 oncolytic virus in glioma model. A) graph showing tumor doubling time between the different treatment groups of OVCAR8 inoculated mice. Increased doubling time corresponds to slower tumor growth. B) Signal intensity v. treatment shows mice tumor burden over a 5-week period.
Figure 5B:
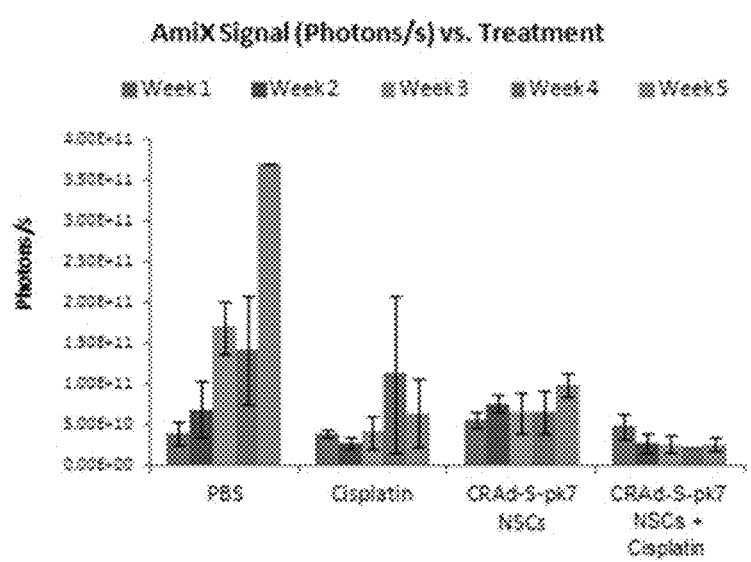

Example 4: CRAd-Survivin-Pk7 NSCs Delay Progression of Ovarian Cancer in Immunodeficient Xenograft Models Both subcutaneous (FIG. 5A) and orthotopic (FIG. 5B) xenograft models were established to assess the therapeutic efficacy of CRAd-Survivin-pk7 NSCs as a single agent and in combination with cisplatin. In the flank setting, CRAd-Survivin-pk7 NSCs slowed tumor volume progression both in the presence and absence of cisplatin (FIG. 5A). As a single agent, CRAd-Survivin-pk7 NSCs delayed the tumor volume doubling time from 7 to 14 days after the first treatment, and from 15 to 26 days after a second treatment. When administered in combination with cisplatin, the tumor volume doubling time extended slightly to 15 days after a first treatment, and 29 days after a second treatment. In the orthotopic setting, CRAd-Survivin-pk7 NSCs slowed tumor progression either with or without cisplatin (FIG. 5B).

Collectively, the preliminary data demonstrates the therapeutic potential of NSC CRAd treatments within an immunocompetent mouse model. The targeted delivery method can prove to be more useful than the current widespread use of small molecule immune checkpoint inhibitors given their association with autoimmune-like toxicities (Kong et al., 2014).

The NSCs are expected to distribute the CRAd-Survivin-pk7 OV within metastatic tumor sites, which will replicate in ovarian tumor cells due to their high surviving expression levels. Infected tumor cells will no longer express high levels of PD-L1 or CD47, thus enabling efficient T cell recognition and clearance. This therapeutic approach will potentially increase long-term survival, and reduce toxicities associated with current therapies. Over the long-term, this approach may also be applicable to other high survivin-expressing cancers such as breast and lung cancer (Pesonen et al., 2011; and Shinoura et al., 1999).

Clinical trials for application of immunomodulatory CRAd-Survivin-pk7-loaded NSCs to treat metastatic, chemo-resistant ovarian cancer can be done. The success in moving NSC-mediated therapies into clinical trials demonstrates the potential to move the therapy disclosed here in into the clinic as well (Aboody et al., 2013). Furthermore, this dual cytotoxic/immune checkpoint inhibitor therapy can be extended into other types of cancer, especially those having up-regulated survivin, PD-L1, and CD47.

Example 5: Materials and Methods for Examples 6-18

Microarray Analysis of Survivin and CRAd-Survivin-Pk7 Entry Receptor Expression in Patient Cohorts Tumor versus normal Birc5 gene expression was calculated using 185 cisplatin-resistant patient tumors and 10 healthy tissue samples.[43,44] Leave-one-out cross-validation was applied to each tumor cohort and confirmed by a permutation test. External validation was conducted by applying the gene signature to a publicly available array database of expression profiles of advanced stage suboptimally debulked tumors. Data showing survivin expression in different peritoneal tissues were obtained from GTExPortal and modified to include only the peritoneal tissues of relevance to experiments described herein. Expression values are shown in RPKM (reads per kilobase of transcript per million mapped reads), calculated from a gene model with isoforms collapsed to a single gene. No other normalization steps have been applied. The mRNA expression scores for putative CRAd-Survivin-pk7 viral entry receptors were obtained from The Cancer Genome Atlas serous ovarian cancer project[45,46] and modified to include only the 100 patients of 311 total patients who exhibited amplified surviving expression.

Human Tissue Procurement and Processing

Fresh tumors, non-malignant tissues, and ascites were obtained from patients who gave institutional review board (IRB)-approved informed consent (City of Hope [COH] IRB 15280) before tissue collection at the COH Medical Center. The fresh tumors and non-malignant tissues were either preserved as untreated controls or cut into about 5-mm pieces that were then incubated in 24-well dishes with each well containing 0.5 mL of complete media and either $5 \times 10^8$ VP of free CRAd-Survivin-pk7 or $5 \times 10^5$ NSC.CRAd-Survivin-pk7. After a 6-hour incubation, NSCs had plated and the tissue was floating, so Boyden chamber inserts were used to maintain contact between the NSCs and the tissue to facilitate viral transfer. Tissues were collected on days 1 and 3 when NSC lysis was observed. Tissues were washed, fixed, and processed for immunological staining or qPCR analysis of viral load. The fresh ascites was heat inactivated at 56° C. for 60 minutes to eliminate complement proteins, but leave neutralizing antibodies intact as previously described.[47] It was then frozen until used for western blot analysis and the viral neutralization assay.

Detection of CRAd5 Neutralizing Antibodies in Patient Ascites

Neutralizing antibodies against CRAd-Survivin-pk7 were recognized in ascites samples by western blotting as previously described.[48] In brief, CRAd-Survivin-pk7 was diluted in PBS to concentrations of 125, 250, 500, and 1,000 ng protein/mL, then subjected to SDS-PAGE (10% NuPAGE Bis-Tris Gel; Thermo Fisher). Following electrophoresis, proteins were transferred by semi-dry electroblotting onto a nitrocellulose membrane (Bio-Rad), which was blocked with 5% nonfat dried milk/0.1% Tween in PBS (PBST) for 90 min at room temperature. Ascetic fluid diluted 1:1,000 in PBST was added to the membranes and incubated for 90 min at room temperature. Membranes were washed 3×10 min in PBST. Membranes were then incubated in a 1:10,000 solution of anti-human Ig (H+L), HRP conjugate (Promega) for 90 min at room temperature. After washing, membranes were developed with 3,3',5,5'-tetramethylbenzidine (TMB) stabilized substrate for horseradish peroxidase (Promega) and imaged.

Viral Neutralization Assay

A luminescent assay using the OVCAR8.EGFP.ffluc cell line was used to quantify viral neutralization after a 30-min exposure to heat-inactivated patient ascites fluid. A cell suspension was made of $10^5$ OVCAR8.EGFP.ffluc cells/mL, and 100 mL was added to each well of a 96-well plate. The next day, heat-inactivated ascites was diluted using 5-serial doublings. Serum-negative controls were also included. To each dilution, 5 mL of free CRAd-Survivin-pk7 virus ($2.5\times 10^{10}$ VP/mL) or $5\times 10^6$ NSC.CRAd-Survivin-pk7 cells were incubated for 30 min at 37° C. The ascites was then aliquoted into the 96-well plate containing OVCAR8.EGFP.ffluc tumor cells. After 8 hours, the NSCs had adhered and media were replaced. Plates were incubated for another 4 days to allow oncolysis. On day 5, media were removed and replaced with media containing 100 mg/mL D-luciferin substrate. After 10 min, the resulting luciferase signal was read using a SpectraMax M3 microplate reader (Molecular Devices, CA, USA).

Cell Culture

NSC lines including the human, v-myc immortalized, HB1.F3.CD NSC line were obtained from Seung Kim (University of British Columbia, Canada).[49] These were further modified by Dr. Maciej Lesniak (Northwestern University) to produce CRAd-Survivin-pk7 as previously described.[8] NSC lines were cultured in DMEM (Invitrogen) supplemented with 10% fetal bovine serum (Gemini Bio), 1% L-glutamine (Invitrogen), and 1% penicillin-streptomycin (Invitrogen) and maintained at 37° C. in a humidified incubator (Thermo Electron Corporation) containing 6% $CO_2$. Ovarian cancer cell lines were cultured in RPMI basal media with the same supplements. For all cell lines, when cells reached 80% confluency, they were passaged using a 0.25% trypsin and EDTA solution (Invitrogen); media were changed every 2-3 days. Ovarian cancer cell lines, Firefly luciferase-expressing OVCAR8 (OVCAR8.EGFP.ffluc), SKOV-3 (SKOV-3.ffluc), Kuramochi, OVCAR3, and CAOV3 cell lines, were provided by Dr. Carlotta Glackin. The ID8 murine glioma line was obtained from Dr. Katherine Roby (University of Kansas). A2780 and U87 human glioma cell lines were obtained from American Type Culture Collection. All tumor lines were used to generate tumor-conditioned media by replacing culture media with serum-free media when cells were 80%-100% confluent followed by a 48-h incubation period.

In Vitro Efficacy Co-Culture Assay

Tumor cells were plated at $5\times 10^5$ cells per well in 6-well plates. Select wells also received NSC.CRAd-Survivin-pk7 at a 1:1, 1:10, 1:100, or 1:1,000 ratio. At select time points, wells were washed with PBS and stained with crystal violet or assessed for total DNA content (PicoGreen DNA quantification kit; Invitrogen). Wells were imaged using brightfield microscopy to obtain a visual representation of live cells per well. DNA content was quantified using a SpectraMax M3 microplate reader (Molecular Devices, CA, USA).

In Vitro Synergy Experiment: Chou-Talalay Analysis

OVCAR8.EGFP.ffluc cytotoxicity resulting from NSC.CRAd-Survivin-pk7 cells, cisplatin chemotherapy, or both agents in combination was studied by quantifying ffluc expression remaining in culture after 3 days. Tumor cells were plated at $3\times 10^3$ cells per well in 96-well plates. Select wells also received NSC.CRAd-Survivin-pk7 at either a 1:1, 1:10, or 1:100 ratio. After overnight incubation, cisplatin was added in select wells at the indicated concentration. Serial dilutions of cisplatin were tested starting at a concentration of 1 mM. Cultures were incubated for 3 more days. Upon collection, media were replaced with that containing D-luciferin (200 mg/mL), and after a 10-min incubation, the resulting luminescent signal was quantified using a SpectraMax M3 microplate reader (Molecular Devices, CA, USA). Results are expressed as the percentage of surviving cells determined by comparing the luciferase signal of each sample relative to untreated control samples considered 100% viable. The interactions between the NSC.CRAd-Survivin-pk7 viruses and cisplatin were evaluated by calculating Chou-Talalay combination indices (CI) using CompuSyn software (ComboSyn). Each condition was replicated in quadruplet, and the experiment was conducted twice.

In Vivo Subcutaneous Xenograft Ovarian Cancer Model

Female athymic nude mice 6-8 weeks of age (Charles River) were maintained under specific pathogen-free conditions at the COH Animal Resource Center, and all procedures were reviewed and approved by the COH Animal Care Committee. A subcutaneous flank xenograft model in nude mice was established using an EGFP and firefly luciferase-expressing ovarian cancer cell line, $2\times 10^6$ OVCAR8.EGFP.ffluc. Approximately 2 weeks following tumor injections, when the tumors were on average 0.5 cm in diameter, the mice were divided into the four treatment groups: (1) PBS: 100 mL administered i.p. days 1-5; (2) cisplatin (4 mg/kg): 100 mL administered i.p. days 1 and 3; (3) NSC.CRAd-Survivin-pk7 ($1\times 10^6$): 100 mL administered i.p. days 1-5; and (4) combination: NSC.CRAd-Survivin-pk7 ($1\times 10^6$) administered i.p. days 1-5 and cisplatin (4 mg/kg) administered i.p. days 1 and 3. The mice were treated for three weekly cycles with 1 week off in between each cycle. The animals were observed for daily consumption of food and water, appearance, and body conditions. Tumor burden was evaluated via caliper measurements twice weekly over a 5-week period.

In Vitro Boyden Migration Assay

A classic Boyden chamber assay was used to evaluate cell migration. In a 24-well tissue culture plate, 500 mL of target media (either containing only BSA as a negative control or derived from the culture of ovarian cancer cells) was added to each well. At a density of 1×10⁵ cells/well, unmodified NSCs or NSC.CRAd-Survivin-pk7 in DMEM and 5% w/v BSA were placed in transwell polycarbonate membrane cell culture inserts (Fisher) and incubated at 37° C. for 4 hours. After the incubation period, the transwell inserts were placed in a new 24-well tissue culture plate containing Accutase and incubated 10 min at 37° C. Detached cells were then transferred to a 96-well V-bottom plate, centrifuged at 1,500 rpm for 5 min, and resuspended in 1:1 PBS to Guava ViaCount Reagent (EMD Millipore). NSC migration to tumor-conditioned media was assessed using a Guava EasyCyte flow cytometer (EMD Millipore).

In Vivo NSC-CRAd-Survivin-Pk7 Tropism in Orthotopic Ovarian Cancer Model

Female NOD-SCID mice (Jackson Labs) that were 6-8 weeks old were inoculated with 2 million OVCAR8.eGFP.ffluc cells via i.p. injection. After 3 weeks, mice (n=3) were administered i.p. 2×10⁶ DiI-labeled NSC-CRAd-Survivin-pk7. Two days after NSC injection, tumors were harvested. Three tumors per mouse were digested using proteinase K, DNA was extracted (DNA Extraction from fixed tissues kit, Puragene), quantified using a nano-drop, then amplified by PCR using primers for v-Myc and hexon to test for the presence of NSCs and viral particles respectively. GAPDH was used as a loading control (351 bp). Primer sequences are listed in Table 2. DNA purified from unmodified NSCs and NSC-CRAd-Survivin-pk7 was used as a positive control for PCR amplification of the v-Myc gene (replicon size 170 bp), and hexon (179 bp) respectively. Pure water was used as a negative control. PCR products were analyzed by agarose gel electrophoresis and staining of DNA bands with ethidium bromide. An additional 3 tumors per mouse were frozen in Tissue Tek OCT (Sakura Finetek USA) and sectioned on a Leica CM1510 S cryostat (Leica Biosystems). Sections (10 μm thick) were collected on positively charged slides (Thermo Fisher Scientific), immunostained for hexon (Goat Anti-Adenovirus FITC Conjugated Polyclonal Antibody, AB1056F, Millipore), counterstained with DAPI (1 ug/mL, Sigma), then imaged using the Zeiss Axio Observer Z1 fluorescence microscope (ZEISS Microscopy).

TABLE 2

PCR Primers

| Gene | Forward Primer | Reverse Primer |
|---|---|---|
| v-myc rxn 1 | Mari v-myc F: 5'-CCTTTGTTGATT TCGCCAAT-3' (SEQ ID NO: 1) | v-myc Inter R2: 5'-GCGAGCTTCTCCGA CACCACC-3' (SEQ ID NO: 2) |
| Nested v-myc | GAG 1306F: 5'-TCACAGCCAGAT ATCCAGCAGCTT-3' (SEQ ID NO: 3) | v-myc R1: 5'-AGTTCTCCTCCTCC TCCTCG-3' (SEQ ID NO: 4) |
| Hexon | Hex3F: 5'-TTCCGCTTCACT GGACTCTT-3' (SEQ ID NO: 5) | Hex3R: 5'-TGGACAGCGAGGAG AGAAG-3' (SEQ ID NO: 6) |

TABLE 2-continued

PCR Primers

| Gene | Forward Primer | Reverse Primer |
|---|---|---|
| GAPDH | Fwd: 5'-ATGTTCGTCATG GGTGTGAACCA-3' (SEQ ID NO: 7) | Rev: 5'-TGGCAGGTTTTTCT AGACGGCAG-3' (SEQ ID NO: 8) |

DNA purified from unmodified NSCs and NSC.CRAd-Survivin-pk7 was used as a positive control for PCR amplification of the v-myc gene (replicon size 170 bp) and hexon (179 bp), respectively. Pure water was used as a negative control. PCR products were analyzed by agarose gel electrophoresis and staining of DNA bands with ethidium bromide.

Assessment of In Vivo Efficacy Study in Orthotopic Ovarian Cancer Model

Female NOD-SCID mice (Jackson Labs) that were 6-8 weeks old were inoculated with 2 million OVCAR8.eGFP.ffluc cells via i.p. injection. After 1 week, mice (n=11/group) were divided into four treatment groups: (1) PBS: 100 μL administered i.p. days 1-5; (2) Cisplatin (4 mg/kg): 100 μL administered i.p. days 1,3; (3)NSC-CRAd-Survivin-pk7 (1×10⁶): 100 μL administered i.p. days 1-5; and (4) Combination: NSC-CRAd-Survivin-pk7 (1×10⁶) administered i.p. days 1-5 and cisplatin (4 mg/kg) administered i.p. days 1, 3. Both before and after treatment, tumor burden was evaluated weekly via bioluminescence using the SPECTRAL Ami X imaging system over a 5 week period. Firefly luciferase expressing tumor cells were imaged in mice using a charge-coupled device camera (the SPECTRAL Ami X) coupled to the AmiX Image acquisition and analysis software. Mice received an intraperitoneal injection of D-luciferin substrate suspended in PBS at 4.29 mg/mouse. Images were captured while the mice were anesthetized by isoflurane (1.5 L/oxygen, 4% isoflurane) and kept in an induction chamber. Light emission was measured over an integration time of 30 s at 9 min after injection of luciferin.

Clinical Observations

Treated mice were weighed weekly and scored daily Monday through Friday for general good health, i.e. good/water intake, urine and feces production, no signs of scruffy hair coat, emaciation, or hunched posture; any debilitating terminal criteria secondary to tumor growth, including: seizures, tremors, labored or difficult breathing, weight loss (>20% body wt.), hypo- or hyperthermia, impaired ambulation, obvious illness, or inability to remain upright. Any animal in distress was euthanized consistent with the recommendations of the Panel on Euthanasia of the American Veterinary Medical Association. Analysis of clinical observations was performed on symptoms following the start of treatment on study Day 7 and continued through study Day 60, when all mice were harvested. Least squares analysis was used to compare the maximum score achieved by each mouse between each of the control and treatment groups. Mice were individually weighed on study Days 1, 18, 24, 30, 35, 37, 39, 42, 46, 49, 51, 53, 56, 58, and 60. Mice weights were normalized with respect to their pre-treatment weight then averaged for each timepoint.

Statistical Analysis

Data are presented as mean±SEM unless otherwise stated. Statistical significance for percent change in tumor flux at each time point between two groups was examined using a two-sample t-test with a two-sided alternative (*p<0.05 deemed to be significant). The average max daily clinical observation score and early max score were also tested using a two-sample t-test.

Example 6: Survivin Expression in Ovarian Cancer

Figure 6A:
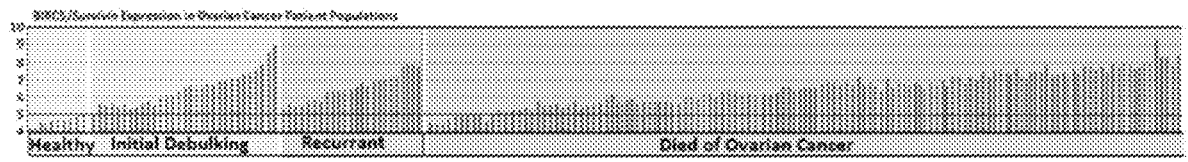
FIGS. 6A-6C illustrate CRAd-Survivin-pk7 NSCs for ovarian cancer. (A) GEO Accession Viewer data showing survivin (BIRC5 gene ID: 202095_s_at) expression in cisplatin-resistant patient tumors (185 samples) and 10 healthy tissues (10 samples). (B) Analysis of GTExPortal data available via Protein Atlas showing survivin expression in various peritoneal tissues. Expression values are shown in RPKM (reads per kilobase of transcript per million mapped reads), calculated from a gene model in which isoforms were collapsed to a single gene. No other normalization steps were applied. Boxplots show median and 25th and 75th percentiles; points are displayed as outliers if they are greater than or less than 1.5 times the interquartile range. (C) Cbioportal Oncoprint compact visualization of mRNA expression scores of three putative CRAd-Survivin-pk7 entry receptors in the 100 patient samples included in The Cancer Genome Atlas serous ovarian cancer project that had survivin amplification (311 patients total). Red indicates amplification; blue indicates deep deletion. BIRC5, survivin; heparin sulfate proteoglycans: GPC1, glypican 1; HSPG2, perlecan; SDC1, Syndecan 1.
Figure 6B:
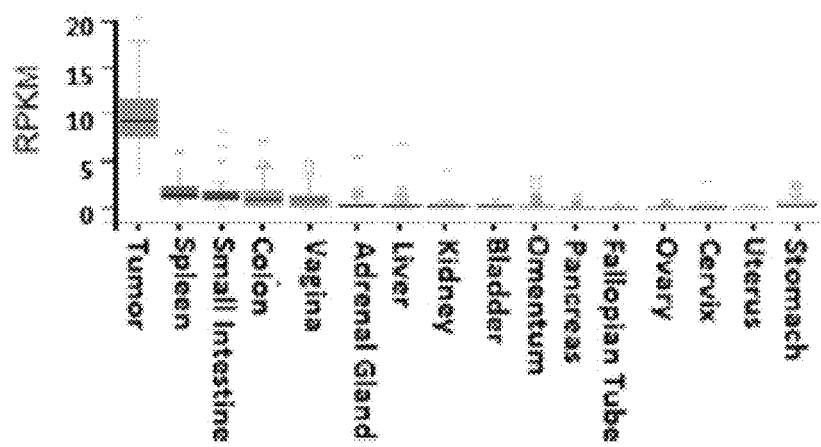
Figure 7:
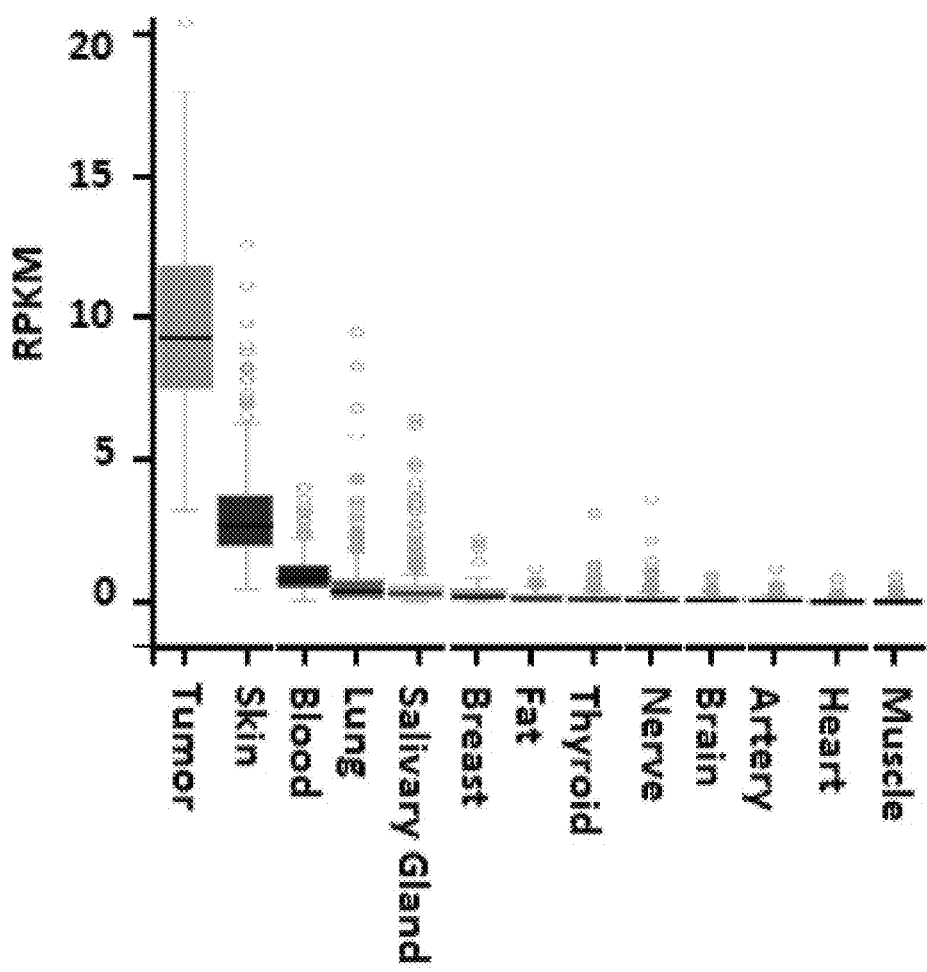
FIG. 7 is an analysis of GTExPortal data showing survivin expression in various organs and tissues from outside the peritoneum. Expression values are shown in RPKM (reads per kilobase of transcript per million mapped reads), calculated from a gene model in which isoforms were collapsed to a single gene. No other normalization steps were applied. Box plots are shown as median and 25th and 75th; points are displayed as outliers if they are greater than or less than 1.5 times the interquartile range.

Before the use of the CRAd-Survivin-pk7 virus, for which replication is under the control of the survivin promoter, the frequency at which survivin expression is upregulated in ovarian cancers was first assessed as compared to normal tissues to ensure that the approach would be of practical utility for ovarian cancer. To do this, survivin gene expression within the publicly available Gene Expression Omnibus Affymetrix human U133A microarray data set (GSE26712) was analyzed. This query dataset includes gene expression data for an extensive set of 185 samples from (90 optimally debulked/95 suboptimally debulked) primary ovarian tumors and 10 samples representing normal ovarian surface epithelium.[8,44] It was found that 93.5% (173/185) of ovarian cancer patients represented in this data set exhibited survivin gene expression levels that exceeded those in normal ovarian surface epithelium (FIG. 6A). Furthermore, because the ultimate intention was to deliver the NSC-CRAd-Survivin-pk7 therapy intraperitoneally (i.p.), it was necessary to ensure that survivin expression is low, and viral replication thereby avoided, in healthy peritoneal organs. To do this, survivin (BIRC5 gencode ID=ENSG00000089685.10) transcription expression levels within the GTExPortal data set were analyzed; which revealed that although survivin is highly expressed in tumors, it is not highly expressed in normal adult organs within the peritoneal cavity (FIG. 6B) or in organs outside the peritoneal cavity (FIG. 7). It is noted, that adult mesenchymal and intestinal progenitor cells express survivin[50,51], and so utilizing the NSCs to distribute this virus solely to tumor locations should minimize any unintended off-target distribution.

Example 7: CRAd-Survivin-Pk7 Transduction in Ovarian Cancer

Figure 6C:
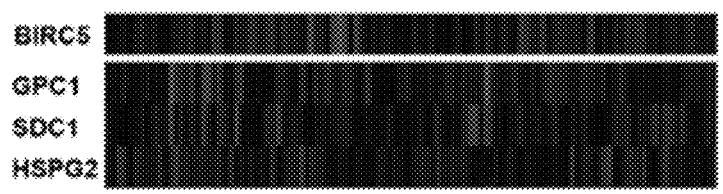

Based on the previous experience in the context of glioma, it was expected that once CRAd-Survivin-pk7-expressing NSCs localize to ovarian tumors, they will produce virus at the tumor site(s) for up to 5 days before achieving release of viral agent[52]. Following this release, efficient infection of surrounding tumor cells will rely on rapid viral uptake by tumor cells expressing cell-surface receptors permissive for adenoviral entry. The poly-lysine modification to the fiber knob protein (pk7) contained within CRAd-Survivin-pk7 permits the virus to bind to and enter tumor cells that express heparin sulfate proteoglycan family members such as perlecan (HSPG2), glypican-1 (GPC1), and syndecan-1 (SDC1).[53,54] To measure expression of these putative adenovirus entry receptors in ovarian cancer patients, Cbioportal Oncoprint analysis of samples from 100 patients with survivin amplification who were included in the Cancer Genome Atlas serous ovarian cancer project was conducted.[45,46] This analysis revealed variability in expression of these surface receptors, but 86% of ovarian cancer patients who overexpressed survivin also expressed at least one of these viral entry receptors (FIG. 6C). This result implies that there is strong potential for enhanced viral infection to occur within patients, given the multiple routes available for viral entry.

Example 8: CRAd-Survivin-Pk7 NSC Characterization

Figure 8A:
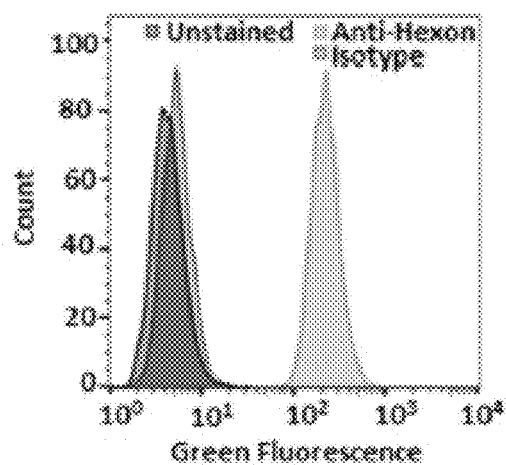
FIGS. 8A-8E show CRAd-Survivin-pk7 NSC characterization. (A) Flow cytometric quantification of hexon-positive NSCs after transduction (MOI=50; 30 VP/infectious unit [IFU]) with CRAd-Survivin-pk7 virus. Anti-hexon samples: 99.76%±0.20% (+); isotype controls: 0.31%±0.06% (+); unstained controls: 0.25%±0.05% (+). (B) Fluorescent image showing infected NSCs stained with fluorescein isothiocyanate (FITC)-conjugated anti-hexon and counterstained with DAPI. Scale bar, 100 µm. (C) PCR quantification used to approximate viral load per NSC (644 VP/NSC). (D) Time-lapse bright-field images showing initial survival but eventual rounding and lysis due to viral burst within NSC.CRAd-Survivin-pk7 cells (lower panels), but not parental NSCs (upper panels). (E) Software-automated quantification of phase-object confluency in each well demonstrating initial seeding and growth of NSC.CRAd-Survivin-pk7 cells peaking at 2 days post-transduction prior to viral burst.
Figure 8B:
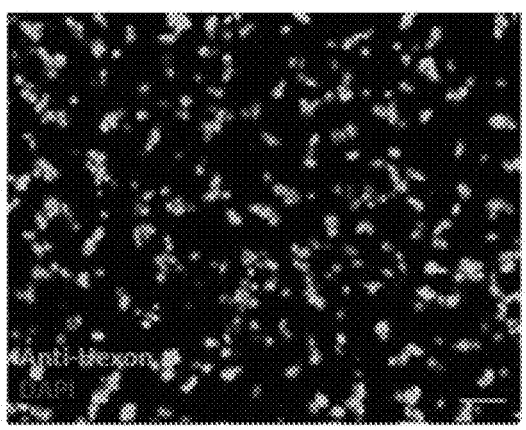
Figure 8C:
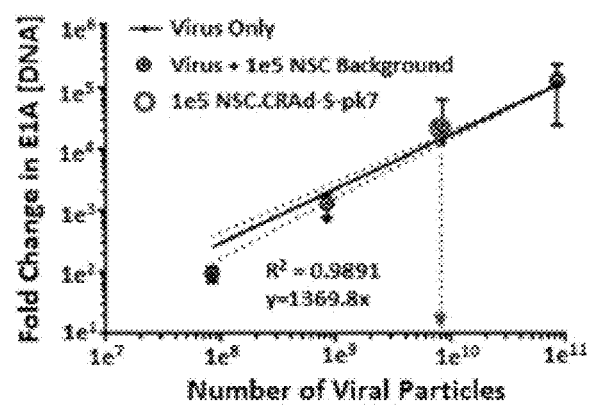
Figure 8D:
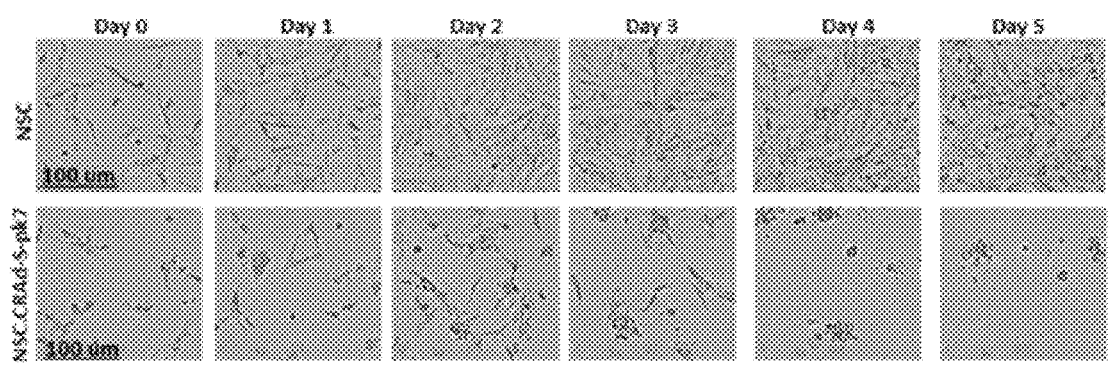
Figure 8E:
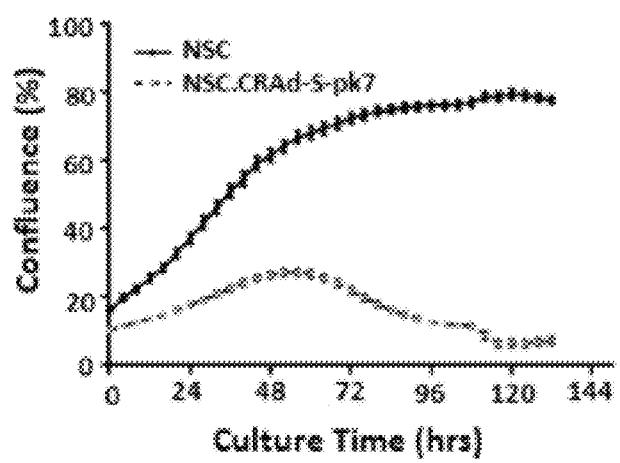

The use of an immortalized cell line as the cell carrier enables the possibility of predictable, reproducible viral loading and release kinetics. Consistent with previous reports,[55] very efficient infection of NSCs by CRAd-Survivin-pk7 was observed with 99.76%±0.20% of NSCs positive for the viral capsid protein, hexon, 1 day after transduction (FIGS. 8A and 8B). qPCR was used to confirm that the viral load per NSC (average=644 viral particle [VP]/cell) was similar to the magnitude we previously reported[55] (FIG. 8C). Primer sequences are listed in Table 2. It was previously described how the intracellular titer peaks 3 days after transduction, at which point the initial viral load amplifies by over a factor of $1 \times 10$.[5,55] As expected, the CRAD-Survivin-pk7-infected NSCs began to undergo virus-induced cell lysis after 2-3 days in culture (FIGS. 8D and 8E).

Example 9: NSC.CRAd-Survivin-Pk7 Tropism to Orthotopic Ovarian Cancer

Figure 9C:
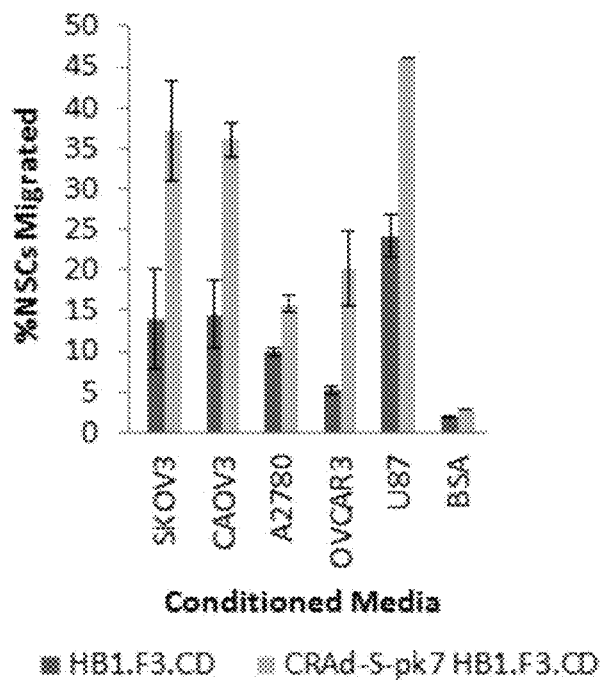
Figure 10A:
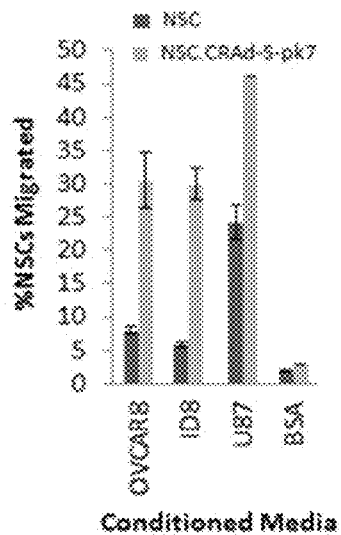
FIGS. 10A-10E show NSC-CRAd-Survivin-pk7 tropism to ovarian cancer. (A) Boyden migration assay comparing tropism of NSC-CRAd-Survivin-pk7 and NSCs with ovarian cancer conditioned media versus U87 (+, "100") and BSA (−) control media. (B and D) Organ plucks 3 weeks after tumor inoculation showing ovarian metastases (large white nodules) occupying omental tissue in both the immunodeficient (B) and immunocompetent (D) mouse models. (C and E) DiI-labeled NSCs (red) loaded with CRAd-Survivin-pk7 (yellow) were injected i.p. into mice with established EGFP ovarian metastases (green). NSC.CRAd-Survivin-pk7 distribution is shown in both (C) xenograft and (E) syngeneic metastatic ovarian cancer models. Scale bars: 50 µm (applies to both image sets).

To confirm that the viral agent did not interfere with the tumor-tropic properties of the NSCs toward ovarian cancer-derived cytokines, an in vitro Boyden chamber migration assay was conducted. The NSC.CRAd-Survivin-pk7 effectively migrated to conditioned media from a range of ovarian cancer cell lines (FIG. 9C) including the OVCAR8 and ID8 cell lines used for the xenograft and syngeneic mouse models (FIG. 10A). In fact, NSC.CRAd-Survivin-pk7 showed greater tropism to tumor-conditioned media than did the untransduced parental HB1.F3.CD NSCs.

Figure 10B:
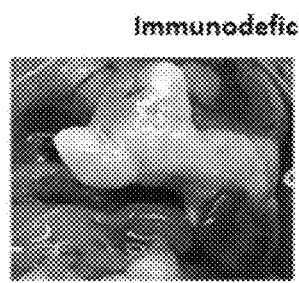
Figure 10C:
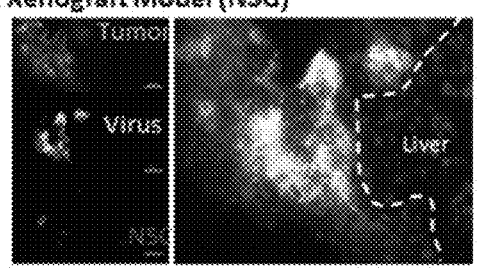
Figure 10D:
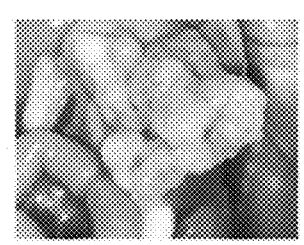
Figure 10E:
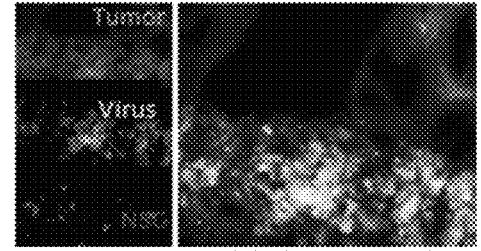
Figure 11A:
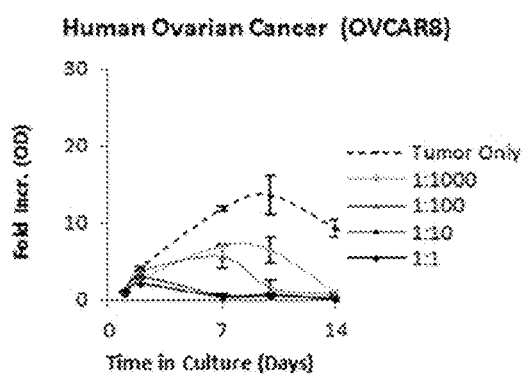
FIGS. 11A-11D show ovarian cancer lysis by CRAd-Survivin-pk7 NSCs. NSC.CRAd-Survivin-pk7 were co-cultured at the indicated seeding ratios with the human OVCAR8 (A and B) or mouse ID8 (C and D) ovarian tumor cell line and cultured for 14 days. (A and C) The fold increase in crystal violet absorption relative to day 1 (average±SD) is shown for both OVCAR8 (A) and ID8 (C) cocultures. (B and D) Representative brightfield images of crystal violet-stained co-cultures are shown for both OVCAR8 (B) and ID8 (D) co-cultures. Scale bar, 50 µm.
Figure 11B:
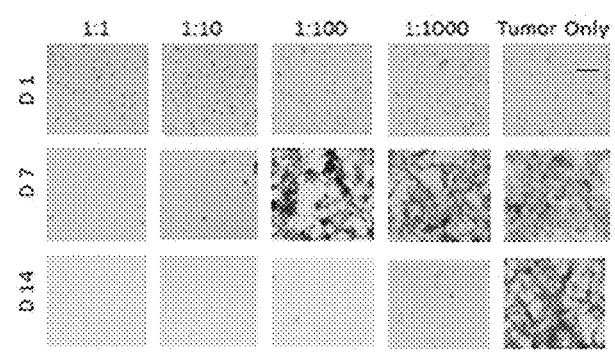
Figure 11C:
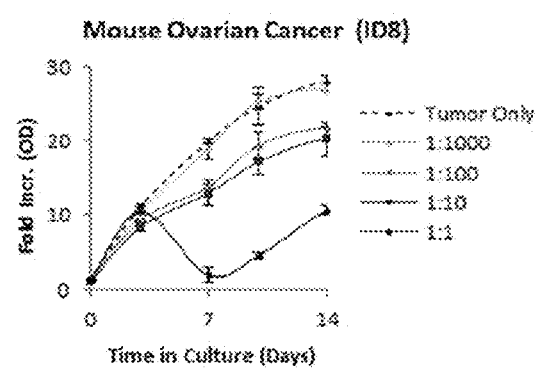
Figure 11D:
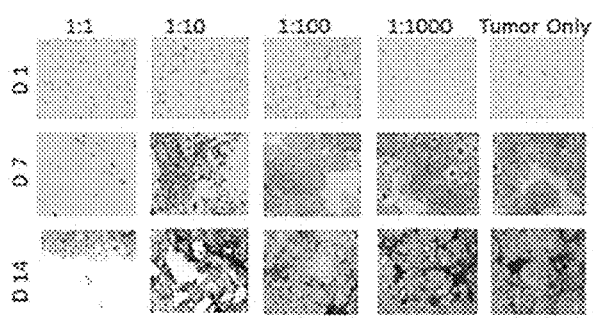

It was previously demonstrated that NSCs home to ovarian tumors after i.p. administration into mice bearing either SKOV3 or OVCAR8 i.p. xenografts.[56] The OVCAR8 cell line was used for the xenograft model given its ability to consistently engraft combined with its moderate genetic similarity to high-grade serous ovarian cancer tumor samples.[57] To confirm that NSC.CRAd-Survivin-pk7 could deliver the oncolytic viral agent to peritoneal metastases, EGFP-expressing OVCAR8 and ID8 disseminated peritoneal tumors were established in NOD scid gamma (NSG) or B6 mice, respectively (FIGS. 10B and 10D). Two weeks later, the mice were administered 1,1'-dioctadecyl-3,3,3',3'-tetramethylindocarbocyanine perchlorate (DiI)-labeled NSC.CRAd-Survivin-pk7s. All peritoneal tissues were harvested 2 days after administration. To visualize NSC-mediated viral secretion, anti-hexon viral staining was performed on sectioned tumors to confirm viral distribution outside of the DiI-labeled NSCs but within the tumor (FIGS. 10C and 10E). Within both xenograft and syngeneic models, the yellow anti-hexon viral stain not only co-localized with the red DiI-labeled NSC.CRAd-Survivin-pk7s, but also spread throughout the EGFP-positive tumor tissue (FIGS. 10C and 10E). This result suggests that at 2 days after administration, some of the virus is being released, whereas some is still contained within the NSCs, consistent with our in vitro viral burst kinetics. Although the yellow anti-hexon viral stain never extended beyond the green EGFP-positive tumor nodules into adjacent normal tissue, it cannot yet be determined whether the combined use of NSC carriers and survivin-driven viral replication effectively avoid off-target tissue distribution given that human adenoviruses do not replicate well within mouse tissue.

Example 10: In Vitro Efficacy of NSC.CRAd-Survivin-pk7

Figure 9A:
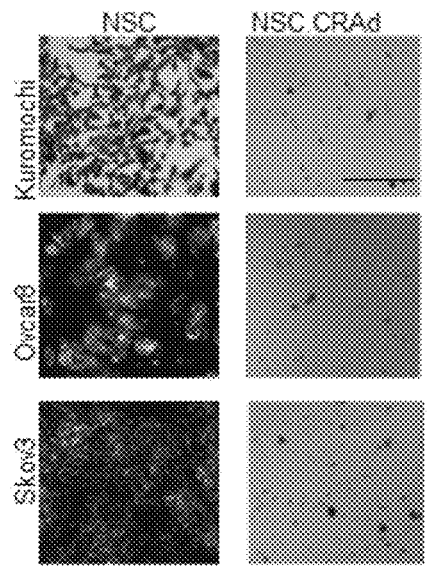
FIGS. 9A-9C show ovarian cancer lysis by CRAd-Survivin-pk7 NSCs. (A-B) CRAd-Survivin-pk7 NSCs co-cultured in a 1:1 seeding ratio with 3 different cisplatin-resistant ovarian tumor cell lines shows elimination of tumor cells within 7 days as indicated by crystal violet stained culture wells (A); and a decrease in total DNA content in culture over 5 days (B). (C) Boyden migration assay comparing tropism of NSC-CRAd-Survivin-pk7 and NSCs to ovarian cancer conditioned media vs. U87 (+, "100") and BSA (−) control media.
Figure 9B:
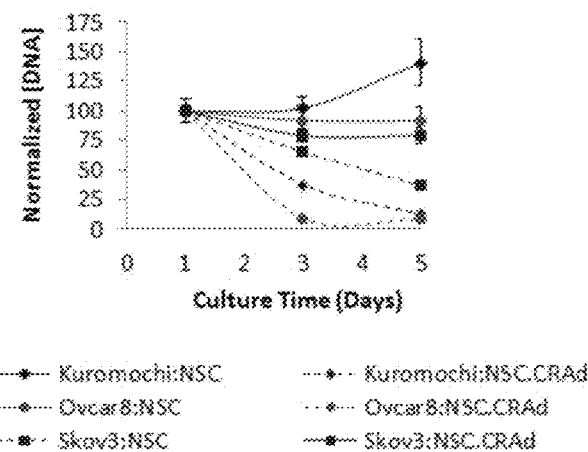

The cytotoxicity of NSC.CRAd-Survivin-pk7 against established ovarian cancer cells was determined. NSC.CRAd-Survivin-pk7 was co-cultured with three different human ovarian cancer cell lines (Skov3, OVCAR8, and Kuromochi using a 1:1 ratio of NSC.CRAd-Survivin-pk7 to ovarian cancer cells) and efficient elimination of tumor cells from all three lines was observed over the course of 5 days (FIG. 9). In contrast, no cell killing was seen in co-cultures of parental NSCs and any of the three ovarian cancer cell lines. This indicates that the CRAd-Survivin-pk7 virus could replicate within NSCs, infect neighboring tumor cells, and continue to amplify throughout the tumor culture.

In preparation for the in vivo studies within both xenograft and syngeneic models, the sensitivity of the human ovarian cancer line (OVCAR8) and a mouse ovarian cancer line (ID8) was further explored (FIG. 11). NSC.CRAd-Survivin-pk7 significantly reduced (>9-fold less than tumor-only control) the number of OVCAR8 cells by day 14 in culture, even when seeded at an initial ratio of 1:1,000 NSC.CRAd-Survivin-pk7:OVCAR8 cells (FIGS. 11A and 11B). These data confirm the potent oncolytic potential of NSC.CRAd-Survivin-pk7 to produce a considerable local bystander effect against the OVCAR8 cancer cell line. The virus was less potent against the faster replicating mouse ID8 line. Nonetheless, NSC.CRAd-Survivin-pk7 significantly reduced (>40% less than tumor-only control) the number of ID8 cells by day 14 in culture, when seeded at an initial ratio of 1:10 NSC.CRAd-Survivin-pk7:ID8 cells (FIGS. 11C and 11D). These data demonstrate that the ID8 line is semi-permissive for CRAd-Survivin-pk7 replication, and thus useful for in vivo experiments within a B6 immunocompetent mouse model. Collectively, the in vitro cytotoxicity results confirm the potential for NSC.CRAd-Survivin-pk7 to kill ovarian cancer cells. However, given that metastatic ovarian cancer spreads throughout the peritoneal cavity, whether NSC.CRAd-Survivin-pk7 would be effective in the peritoneal setting would need to be determined.

Figure 12A:
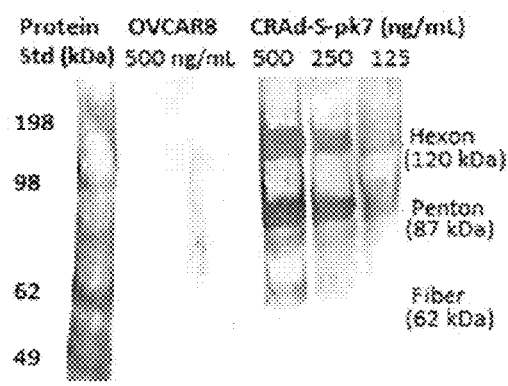
FIGS. 12A-12D show that NSCs enhanced CRAd-Survivin-pk7 efficacy. (A and B) NSC protects CRAd-Survivin-pk7 from adenovirus neutralization. (A) Blot analysis assessing recognition of adenovirus antigens hexon, penton base, and fiber by antibodies present in ascetic fluid. Dilutions of purified CRAd-Survivin-pk7 virus were subjected to SDS-PAGE. Following semi-dry blotting and blocking in non-fat milk, membranes were incubated with ascites pooled from three patients with ovarian cancer. Bound antibodies were visualized using horseradish-peroxidase-conjugated antihuman IgG secondary antibodies. OVCAR8 human ovarian cancer cells served as a negative control. (B) Neutralization of adenovirus infectivity by ascites fluid. Two thousand OVCAR8.EGFP.ffluc cells/96-well plate were co-cultured with either 2,000 NSC.CRAd-Survivin-pk7 (2.5×$10^7$ pfu) for 5 days or free CRAd-Survivin-pk7 (2.5×$10^7$ pfu) for 3 days or NSC-CRAd-Survivin-pk7 in the presence of serial 2-fold dilutions of ascetic fluid obtained from three different ovarian cancer patients. Ascitic fluid was replaced after 24 hours with culture media. Data are presented as average raw luminescent signal ±SD. (C and D) NSC improves CRAd-Survivin-pk7 delivery in vivo. (C) qPCR quantification of increased adenoviral E1A gene copy number in mouse tumors treated with NSC.CRAd-Survivin-pk7 (black bars) in comparison with free virus (gray bars) 1 day after administration. (D) Tumor volume was determined by weighing the omentum (primary site of tumor formation) after three treatment rounds; each point indicates an individual mouse. Data for (C) and (D) represent mean±SEM.

Example 11: NSCs Protect the CRAd-Survivin-Pk7 from Neutralizing Antibodies Present in Patient Ascites Pre-existing anti-Ad5 antibodies (40%-69% of the adult population in the United States is seropositive to Ad5[33]) present in ascites fluid within the peritoneal cavity can rapidly neutralize Ad5-based vectors, and thus can significantly hinder the clinical application of i.p.-administered CRAds for ovarian cancer. Whether CRAd-Survivin-pk7 was recognized by antibodies present in ascetic fluid was determined. To do this, cell-free ascetic fluid obtained from ovarian cancer patients during routine peritoneal drainage was applied to a membrane onto which denatured, electrophoresed CRAd-Survivin-pk7 samples were blotted (FIG. 12A). The ascites fluid positively recognized the viral antigens hexon, penton base, and fiber.

Figure 12B:
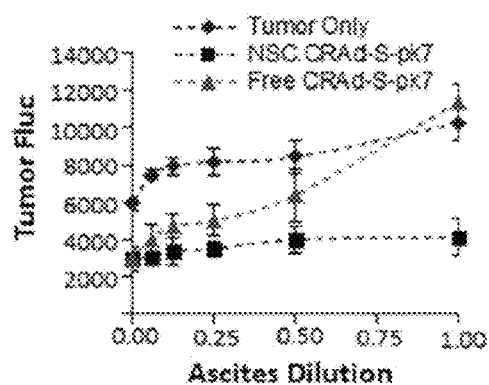

To investigate the possibility that NSCs could protect the CRAd-Survivin-pk7 virus from pre-existing anti-adenovirus antibodies in ascetic fluid, the adenovirus oncolytic potential of free CRAd-Survivin-pk7 and NSC-CRAd-Survivin-pk7 both with and without exposure to human ascites was compared. Free CRAd-Survivin-pk7 had reduced oncolytic ability upon 24-hour exposure to ascites fluid, as evidenced by decreased ability to kill OVCAR8 tumor cells as compared with NSC.CRAd-Survivin-pk7 and the tumor-only negative control (FIG. 12B). In addition, the extent of viral inhibition increased at greater concentrations of the ascites fluid (FIG. 12B). The NSCs seem to shield viruses from neutralizing antibodies within ascites, suggesting their potential to be effective viral carriers for i.p.-administered oncolytic therapies.

Example 12: Treatment with NSC.CRAd-Survivin-pk7 Slows Progression in Orthotopic Tumor Models Next, the orthotopic mouse models were utilized to confirm that NSC-mediated CRAd-Survivin-pk7 delivery improves in vivo efficacy relative to free virus administration. NSG mice (n=7 per group) and B6 mice (n=7 per group) were administered i.p. EGFP-expressing ovarian cancer (OVCAR8 and ID8, respectively). Two weeks after tumor cell inoculation, the mice were treated with either free CRAd-Survivin-pk7 (3 weeks of $5\times10^8$ plaque-forming units [pfu]/day), NSC.CRAd-Survivin-pk7 (3 weeks of $1\times10^6$ cells [$5\times10^8$ pfu]/day), or PBS (control).

Figure 12C:
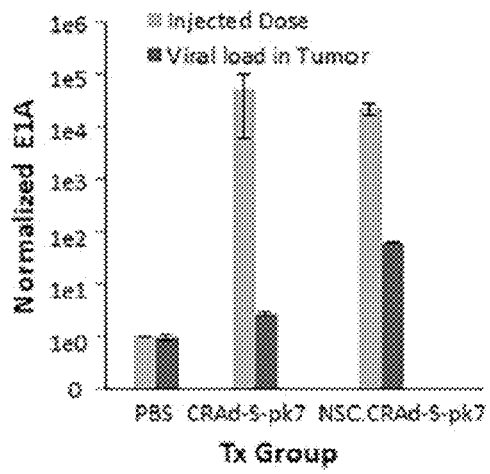
Figure 12D:
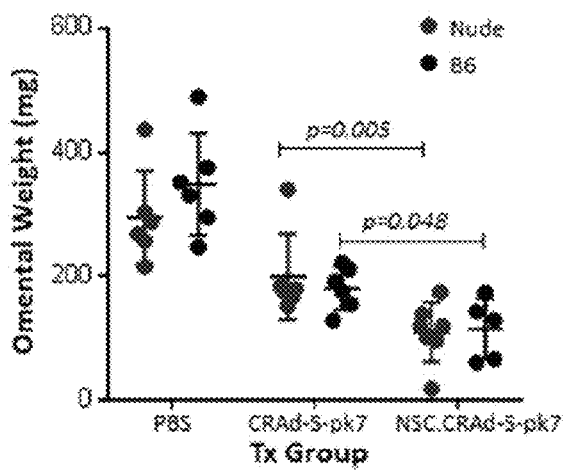

To assess the relative infectivity of CRAd-Survivin-pk7 when delivered either as the free virus or using the NSC carrier, qPCR was used to quantify E1A levels within tumor mets harvested 1 day after the first treatment. Increased adenoviral E1A gene copy number (22.7-fold higher) was found in the tumors of mice treated with NSC.CRAd-Survivin-pk7 instead of free virus (FIG. 12C). To determine whether NSC-mediated improvements in viral load at the tumor would translate to improved treatment efficacy, mice were harvested 1 week after the third treatment round. The omentum, which is the primary site of tumor formation and growth, was collected from all mice and weighed. Free virus administration resulted in a significantly reduced omental tumor burden as compared with mice that received only PBS injections (FIG. 12D). Even more substantial decreases in omental tumor burden were obtained from mice treated with NSC.CRAd-Survivin-pk7 instead of free virus (FIG. 12D). Together these data demonstrate that NSC carriers can improve the delivery and efficacy of CRAd-Survivin-pk7 within the peritoneal setting.

Figure 13A:
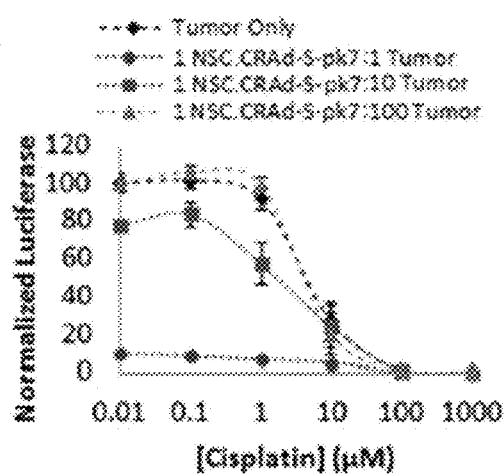
FIGS. 13A-13C show CRAd-Survivin-pk7 NSCs combination with cisplatin (in vitro and flank model). (A) Log-dose versus response plot showing normalized OVCAR8.ffluc viability after co-culture with decreasing ratios of CRAd-Survivin-pk7 NSCs while undergoing continuous cisplatin exposure. (B) Chou-Talalay plot showing log combinatorial index (CI) values: synergism (CI<1), additive effect (CI=1), and antagonism (CI>1). (C) Pilot NSC.CRAd-Survivin-pk7 efficacy study in flank model. Average tumor doubling times (±SD) for OVCAR8 xenograft-bearing mice that received the indicated treatments (n=4 mice/group).
Figure 13B:
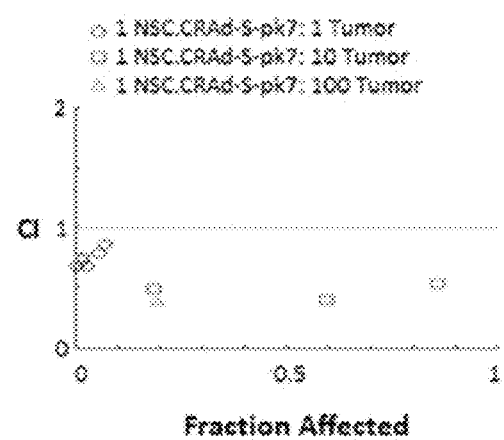

Example 13: Combination Treatment with NSC.CRAd-Survivin-pk7 and Cisplatin In Vitro The most active chemotherapeutic agent used to treat ovarian cancer is cisplatin, but even if patients initially respond, most ultimately die with platinum-resistant disease.[58] Thus, it was important to determine whether NSC.CRAd-Survivin-pk7 can help eliminate ovarian cancer cells that have become resistant to patient-tolerable doses of cisplatin. Co-culture of OVCAR8 tumor cells and NSC.CRAd-Survivin-pk7 with increasing concentrations of cisplatin showed that the virus-loaded NSCs could kill ovarian tumor cells that were otherwise unaffected by low doses of cisplatin (<1 μM) (FIG. 13A). Potential synergistic interactions between NSC.CRAd-Survivin-pk7 and cisplatin were evaluated using the Chou-Talalay methodology, for which a combinatorial index (CI) of <0.9 is considered synergistic, a CI between 0.9 and 1.1 is considered additive, and a CI>1.1 is considered antagonistic.[59] For the combination of cisplatin and NSC.CRAd-Survivin-pk7, all Cis were <1 (FIG. 13B), unless the concentration of cisplatin was extremely high (1,000 μM) or the NSC.CRAd-Survivin-pk7:tumor ratio was very low (1:1,000) (data not shown). These data suggest the two agents may demonstrate synergistic efficacy at patient-tolerable doses.

Example 14: Combination Treatment with NSC.CRAd-Survivin-pk7 and Cisplatin Slows Progression in a Flank Tumor Model To determine whether the in vitro efficacy of NSC.CRAd-Survivin-pk7 in combination with cisplatin also occurred in vivo, a pilot study was performed in which mice bearing subcutaneous flank OVCAR8.EGFP xenografts were treated with either i.p. cisplatin alone (4 mg/kg), intratumoral NSC.CRAd-Survivin-pk7 alone (1×10⁶ cells/5×10⁸ pfu), the combination of intratumoral NSC.CRAd-Survivin-pk7 and i.p. cisplatin (1×10⁶ cells/5×10⁸ pfu, 4 mg/kg), or PBS (control) (n=4 mice per group). Mice began treatments approximately 2 weeks after injection of 5 million OVCAR8.EGFP cells, when the tumors were on average 0.5 cm in diameter (Table 3). The mice were treated for two cycles. Each cycle was 2 weeks long, consisting of 1 week on therapy and 1 week off. Tumor burden was evaluated via caliper measurements twice weekly over a 5-week period.

Two weeks after tumor inoculation, NSC mice were administered either i.p. cisplatin alone (4 mg/kg), NSC.CRAd-Survivin-pk7 alone (2×10⁶ cells/1×10⁹ pfu), or the combination of NSC.CRAd-Survivin-pk7 and cisplatin (2×10⁶ cells/1×10⁹ pfu, 4 mg/kg) (n=2 mice per group). Two days later, mice were euthanized and all peritoneal tissue harvested. To assess NSC.CRAd-Survivin-pk7 and virus biodistribution, three tumors from each mouse were processed for PCR analysis. NSC.CRAd-Survivin-pk7 were able to localize virus to peritoneal tumors in the presence of cisplatin, with hexon DNA detected in all six tumors obtained from mice treated with both agents (three of six were positive for v-myc DNA). Neither hexon nor v-myc DNA

TABLE 3

Flank OVCAR8 Tumor Model Treatment Regimen

| Tx Group | Agent (Dose) | Route | Day 1 | Day 2 | Day 3 | Day 4 | Day 5 |
|---|---|---|---|---|---|---|---|
| 1 | PBS | i.p. | PBS | — | PBS | — | — |
|  |  | i.t. | PBS | PBS | PBS | PBS | PBS |
| 2 | cisplatin (4 mg/kg) | i.p. | cisplatin | — | cisplatin | — | — |
|  |  | i.t. | NSC-CRAd-S-pk7 | NSC-CRAd-S-pk7 | NSC-CRAd-S-pk7 | NSC-CRAd-S-pk7 | NSC-CRAd-S-pk7 |
| 3 | NSC-CRAd-S-pk7 | i.p. | PBS | — | PBS | — | — |
|  | (1e6 NSCs, 5e8 pfu) | i.t. | NSC-CRAd-S-pk7 | NSC-CRAd-S-pk7 | NSC-CRAd-S-pk7 | NSC-CRAd-S-pk7 | NSC-CRAd-S-pk7 |
| 4 | cisplatin (4 mg/kg) + | i.p. | cisplatin | — | cisplatin | — | — |
|  | NSC-CRAd-S-pk7 (1e6 NSCs, 5e8 pfu) | i.t. | NSC-CRAd-S-pk7 | NSC-CRAd-S-pk7 | NSC-CRAd-S-pk7 | NSC-CRAd-S-pk7 | NSC-CRAd-S-pk7 |

Tx, treatment;
i.p., intraperitoneal;
i.t., intratumoral.

Figure 13C:
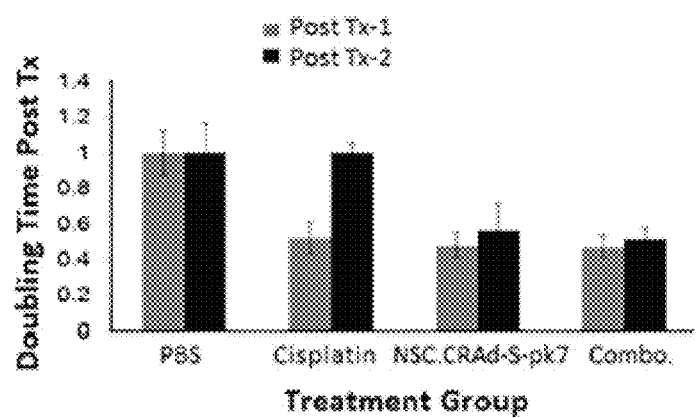
Figure 15A:
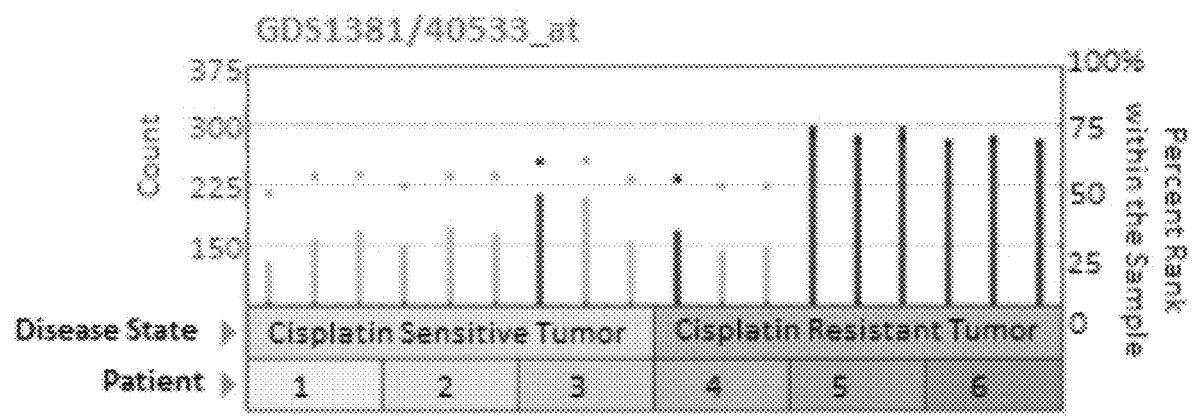
FIGS. 15A-15D show the comparison of survivin expression levels in response to cisplatin treatment. Gene Expression Omnibus Accession Viewer data showing survivin (BIRC5, gene ID: 202095_s_at) expression in: (A) cancer cells prepared from primary cultures of ovarian papillary serous adenocarcinomas in response to cisplatin; (B) A2780 ovarian cancer cells in response to cisplatin; (C) malignant ovarian cancer tumors obtained from 43 patients receiving neo-adjuvant cisplatin therapy or not; and (D) 12 cisplatin-resistant and 16 cisplatin-sensitive high-grade serous epithelial ovarian cancer samples. For all samples, total RNA was analyzed by whole transcriptome profiling using Affymetrix U133 Plus 2.0 arrays.[48]
Figure 15B:
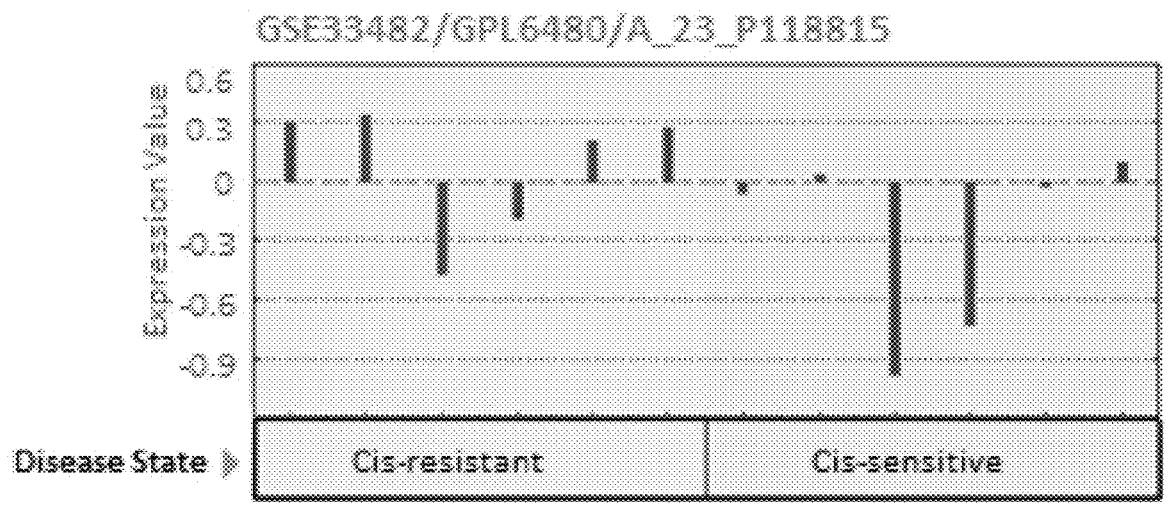
Figure 15C:
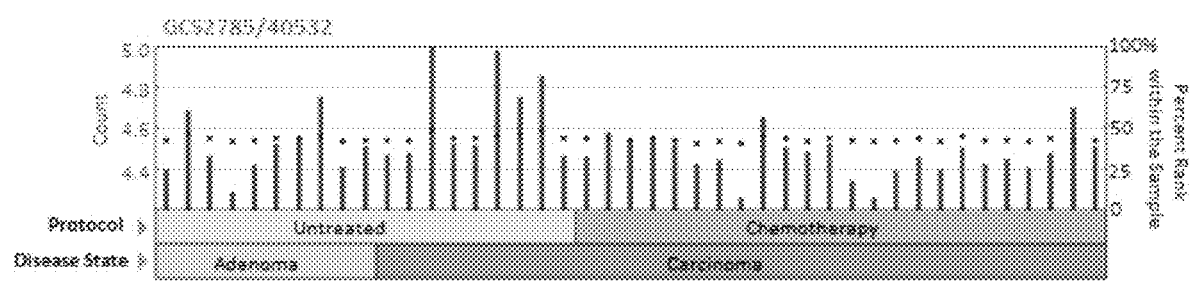
Figure 15D:
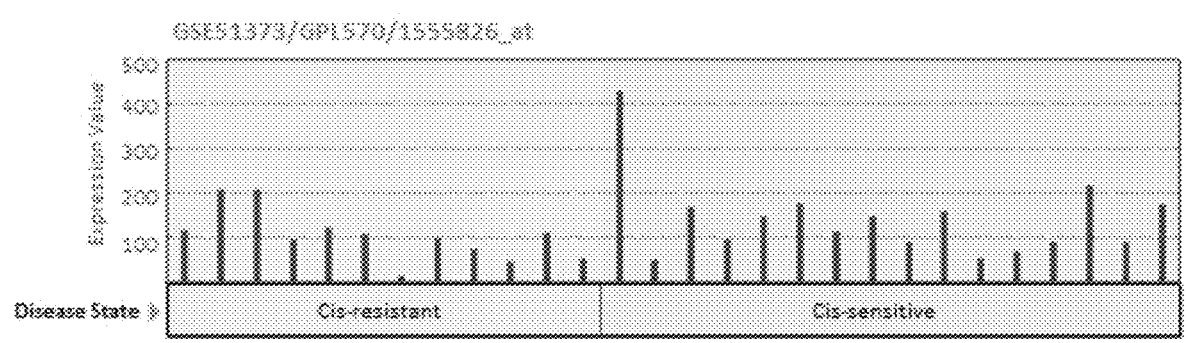

Treatment with NSC.CRAd-Survivin-pk7 slowed tumor progression both as a single agent and in combination with cisplatin as compared with control treatment with PBS (FIG. 13C). As a single agent, NSC.CRAd-Survivin-pk7 delayed the tumor volume doubling time from 7 to 14 days after the first treatment and from 15 to 26 days after the second treatment. When administered in combination with cisplatin, the tumor volume doubling time extended slightly to 15 days after the first treatment and 29 days after the second treatment (FIG. 13C). In contrast, cisplatin alone delayed the tumor volume doubling time from 7 to 13 days after the first treatment, but appeared less effective after the second treatment, yielding a tumor volume doubling time that was not significantly different from that of the saline control (FIG. 13C).

Example 15: Combined Treatment with NSC.CRAd-Survivin-pk7 and Cisplatin Slows Progression in Orthotopic Tumor Models Co-administration of cisplatin did not interfere with NSC.CRAd-Survivin-pk7 tropism within the peritoneal setting.

was detected in tumors obtained from mice treated with either cisplatin alone or PBS (FIG. 14A; three representative tumors are shown per group).

To assess the therapeutic efficacy of NSC.CRAd-Survivin-pk7 as an adjunct to cisplatin therapy, NSG mice (n=11 per group, combined from two independent experiments) were administered 2 million i.p. OVCAR8.EGFP.ffluc. One week after tumor cell injection, the mice were treated with three consecutive treatment cycles (Table 4). After each round of treatment, tumor burden was evaluated via bioluminescence imaging using the SPECTRAL Ami X imaging system (FIG. 14B). In addition, mice were monitored daily using our clinical observation scoring system in which mice are numerically scored from 1 to 7 depending on the number of outward signs of toxicity they display. A higher daily score indicates more treatment-induced toxicity. Any mouse that received the maximum score of +7 or met any terminal criteria was euthanized immediately.

TABLE 4

Orthotopic OVCAR8 Tumor Model Treatment Regimen

| Tx Group | Agent (Dose) | Route | Day 1 | Day 2 | Day 3 | Day 4 | Day 5 |
|---|---|---|---|---|---|---|---|
| 1 | PBS | i.p. | PBS | PBS | PBS | PBS | PBS |
| 2 | cisplatin (4 mg/kg) | i.p. | cisplatin | PBS | cisplatin | PBS | PBS |
| 3 | NSC-CRAd-S-pk7 (1e6 NSCs, 5e8 pfu) | i.p. | NSC-CRAd-S-pk7 | NSC-CRAd-S-pk7 | NSC-CRAd-S-pk7 | NSC-CRAd-S-pk7 | NSC-CRAd-S-pk7 |

TABLE 4-continued

Orthotopic OVCAR8 Tumor Model Treatment Regimen

| Tx Group | Agent (Dose) | Route | Day 1 | Day 2 | Day 3 | Day 4 | Day 5 |
|---|---|---|---|---|---|---|---|
| 4 | cisplatin (4 mg/kg) + NSC-CRAd-S-pk7 (1e6 NSCs, 5e8 pfu) | i.p. i.p. | cisplatin NSC-CRAd-S-pk7 | PBS NSC-CRAd-S-pk7 | cisplatin NSC-CRAd-S-pk7 | PBS NSC-CRAd-S-pk7 | PBS NSC-CRAd-S-pk7 |

Tx, treatment;
i.p., intraperitoneal.

The average percent change in tumor flux was less in all treatment groups as compared with the PBS control group (FIG. 14C). Furthermore, NSC.CRAd-Survivin-pk7 treatment seemed as effective as cisplatin, because no significant differences in tumor flux were seen between the two treatment groups. In contrast with NSC.CRAd-Survivin-pk7, cisplatin treatments were measurably more toxic than saline control treatments, with mice in this group experiencing accelerated weight loss (FIG. 14D) and having both higher average maximum daily scores and earlier time to reach the maximum daily score (FIG. 14E). These outward signs of toxicity were not apparent in the mice treated with NSC-.CRAd-Survivin-pk7. The combination of cisplatin and NSC.CRAd-Survivin-pk7 resulted in lower average tumor flux compared with treating with cisplatin alone, but the results were not statistically significant. However, adding NSC.CRAd-Survivin-pk7 did not significantly worsen the observed toxicity of cisplatin treatments, as measured by daily score (FIG. 14E). This result implies potential for using NSC.CRAd-Survivin-pk7 as an adjuvant treatment when administering cisplatin to achieve increased efficacy with no added toxicity.

Example 16: NSC.CRAd Production and Quality Control

Expansion system is available for GMP scale up. The hollow-fiber bioreactor has about 11,200 fibers/bioreactor and 2.1 m$^2$ culture surface.$^{62}$ The comparisons are shown in Table 5 below. FIG. 16 shows that the clinical-grade NSC.CRAd production and characterization SOPs have been established. The cGMP SOPs have been established for both flask-based production of NSC.CRAds (up to 8 billion cells per clinical lot) and scale-up with Terumo® bioreactor production (up to 23 billion cells per clinical lot). Freeze-thaw and cell-preparation SOPs have been established and are used for all clinical-equivalent research banks used in our lab. This ensures consistency of viral release kinetics for all pre-clinical studies. This controlled approach offers an advantage over viral delivery by autologous MSCs modified ex vivo, for which transduction efficiencies and burst times vary significantly from patient to patient, isolation to isolation.

TABLE 5

| Ideal Cell Carrier | Patient Derived MSCs | HB1.F3.CD21 NSCs |
|---|---|---|
| Homogeneous population | Heterogeneous | ✓ |
| Karyotypic normal | 20% show abnormal karyotypes | ✓ |
| High, reproducible ex vivo loading | Low, unpredictable loading | ✓ |
| Retain tumor-tropism after expansion | Loses tumor-homing after 5-6 passages | ✓ |
| "Off-the shelf" availability | 2 wks to expand | ✓ |

Example 17: NSC.CRAds for Glioma

Figure 17A:
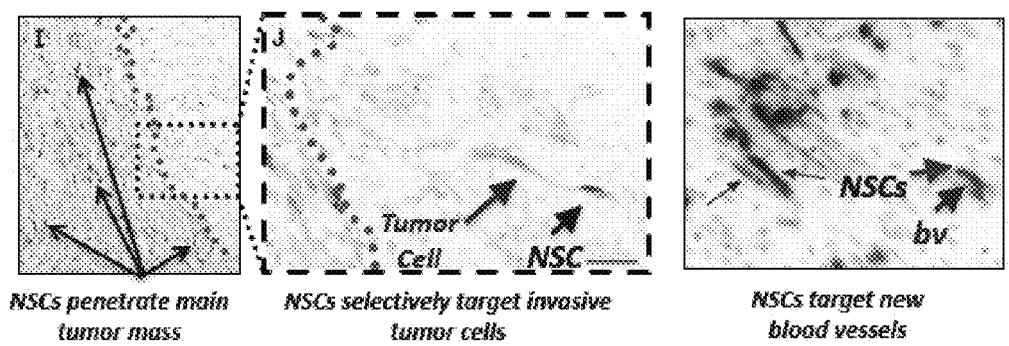
FIG. 17A shows that NSCs exhibited tropism to glioma cells.
Figure 17B:
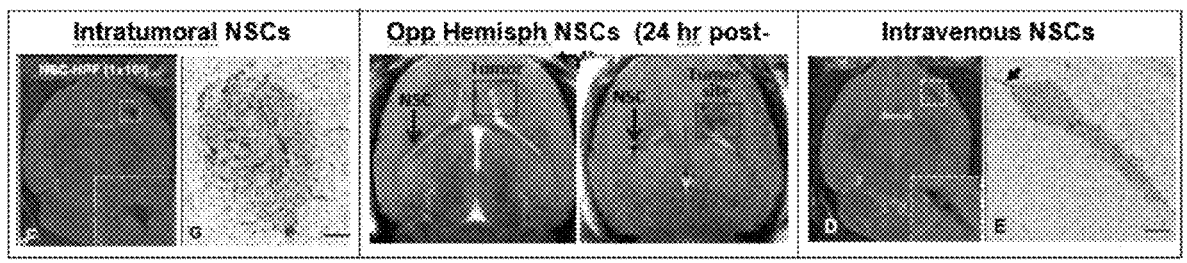
FIG. 17B shows pre-clinical glioma model with iron-labeled NSCs (MRI black; IHC blue).
Figure 18A:
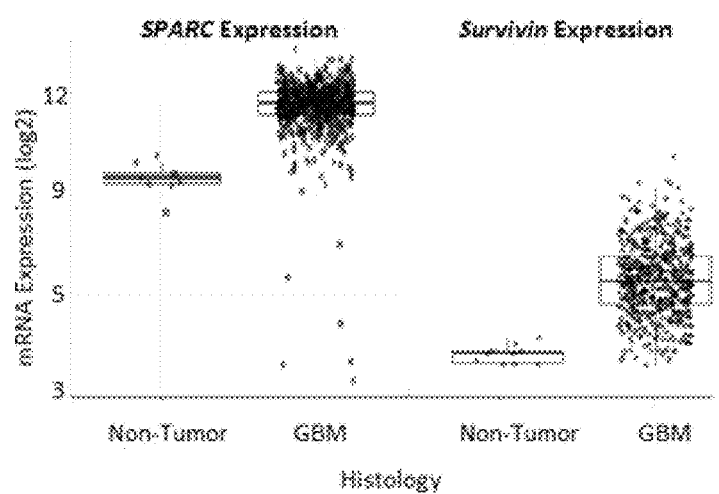
FIGS. 18A-18C illustrate the rationale for CRAd-SPARC and CRAd-survivin in glioma. (A) SPARC and Survivin gene expression in both normal and tumor tissue obtained from GlioVis TCGA_GBM dataset. (B-C) Brightfield images from the Human Protein Atlas of human ovarian tumor tissue stained with either (B) anti-survivin or (C) anti-SPARC antibodies.
Figures 18B, 18C:
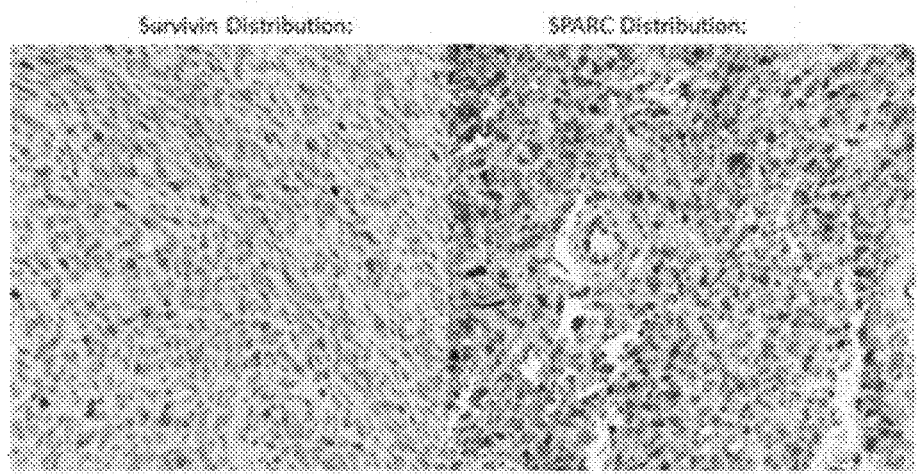
Figure 20A:
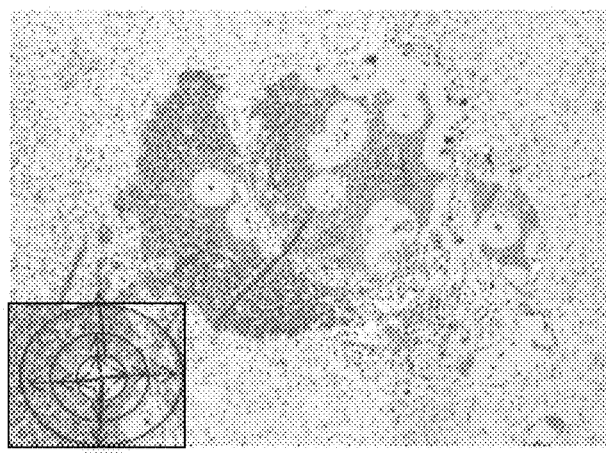
FIG. 20A shows that NSCs carried virus across normal brain tissue to seed oncolytic virus to invasive tumor sites.
Figure 20B:
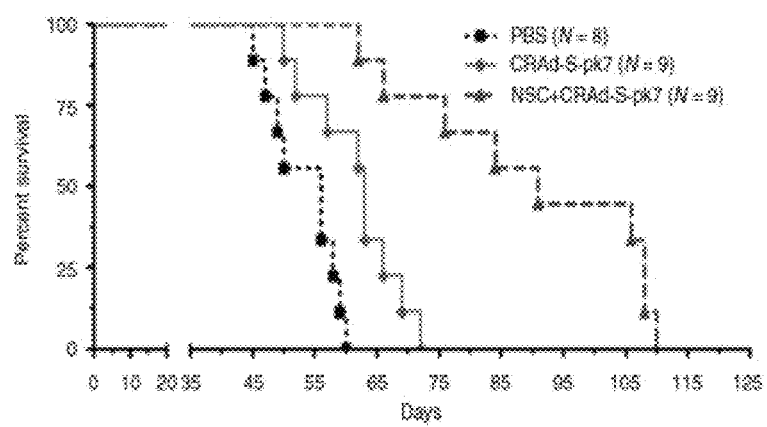
FIG. 20B shows improved therapeutic efficacy in an orthotopic xenograft model of glioma when NSCs were delivering the CRAD-Survivin-pk7 virus relative to free virus administration.
Figure 21A:
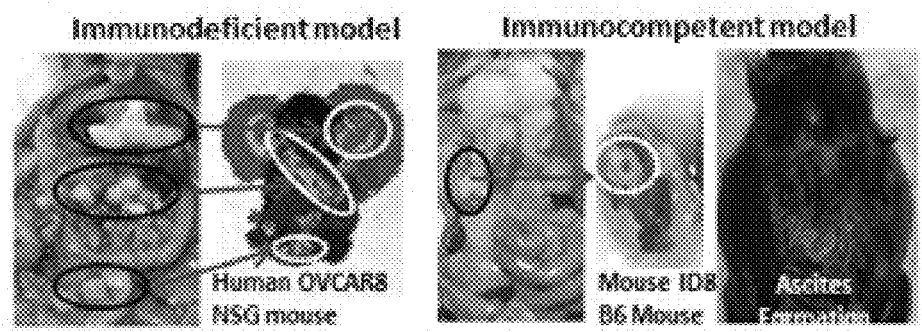
FIGS. 21A-21G show that IP-injected NSC.CRAds demonstrated selective tumor tropism in metastatic ovarian cancer models. (A) Ex vivo photographic and BLI of immunodeficient OVCAR8.ffluc/NSG and immunocompetent ID8.ffluc/C57BL/6 ovarian cancer models. (B-C) Representative fluorescent images of peritoneal tumors harvested 24 hours after IP administration of NSCs (DiI labeled, red). (B) $2 \times 10^6$ parental NSCs demonstrate distribution in OVCAR8.eGFP.ffluc (green), but not in adjacent normal kidney (yellow due to autofluorescence) in NSG mice. (C) $2 \times 10^6$ NSC.CRAds demonstrate distribution in ID8.eGFP.ffluc, but not in intestine (white dotted line) in C57BL/6 mice. Scale bars B=100 μm, C=50 μm. (D-G) NSCs were dual-labeled with DiR and gold nanorods (AuNR) to track their distribution following IP injection in mice with established peritoneal ffluc-labeled ovarian tumors. (D) Live animal images confirm tumor co-localization of dual-labeled NSCs. (E-G) Peritoneal tumors were harvested 1 hour and 24 hours after dual-labeled NSC injections, then digested for inductively coupled plasma mass spectrometry (ICP-MS) quantification of AuNR levels within tumors. This unconventional quantification method was chosen for its sensitivity and confirmed by flow cytometric analysis at the upper end of its dynamic range. (E) AuNR content from all tumors was combined and represented as a percentage of injected dose. (F) Number of NSCs present in individual tumors, calculated by dividing the AuNR content in each tumor by the AuNR content/NSC ratio. (G) AuNR content in IP tumors, presented according to the organs from which they were harvested.
Figure 21B:
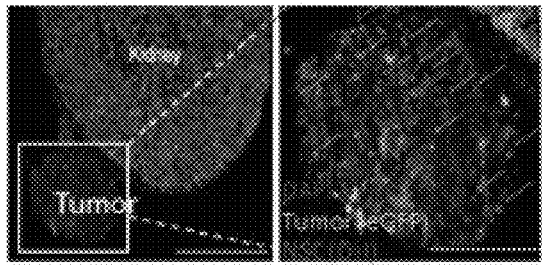
Figure 21C:
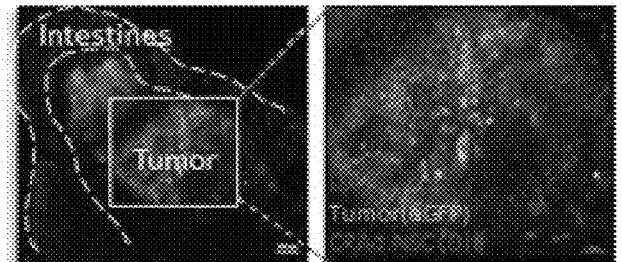
Figure 21D:
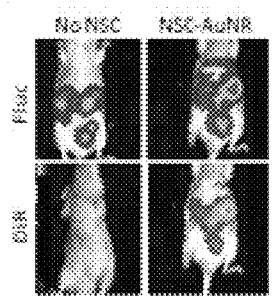
Figure 21E:
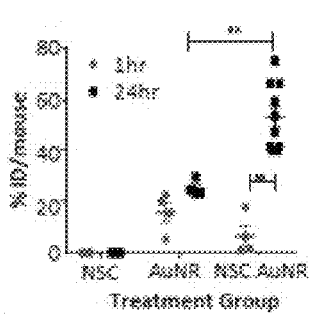
Figure 21F:
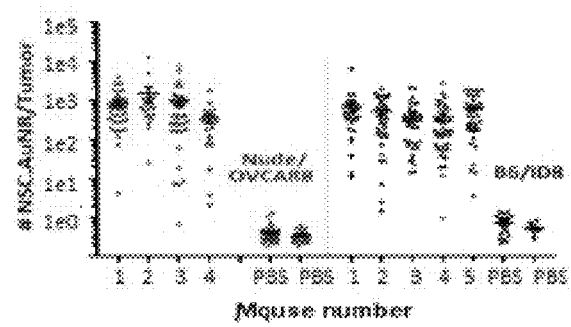
Figure 21G:
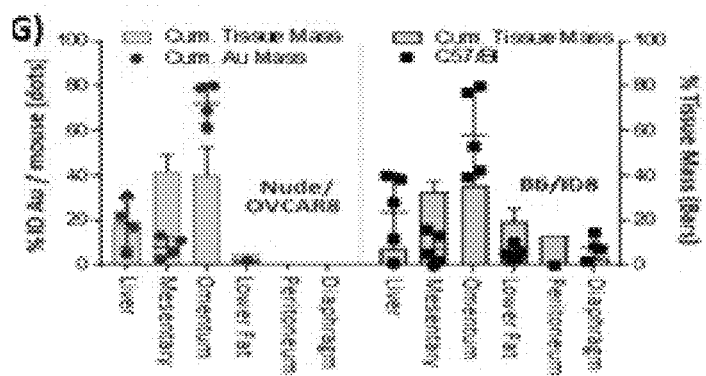

NSC.CRAd-SPARC and NSC.CRAd-Survivin were produced and compared in glioma cell lines. FIG. 17A shows that NSCs exhibited tropism to glioma, and FIG. 17B shows the pre-clinical glioma model. FIG. 18 shows the expression and distribution of SPARC and survivin. FIG. 19 shows the comparison of in vitro efficacy of CRAd-SPARC and CRAd-Survivin. FIG. 20 demonstrates that NSC-facilitated viral delivery in vivo.

Example 18: NSC.CRAds for Ovarian Cancer

Figures 22A, 22B:
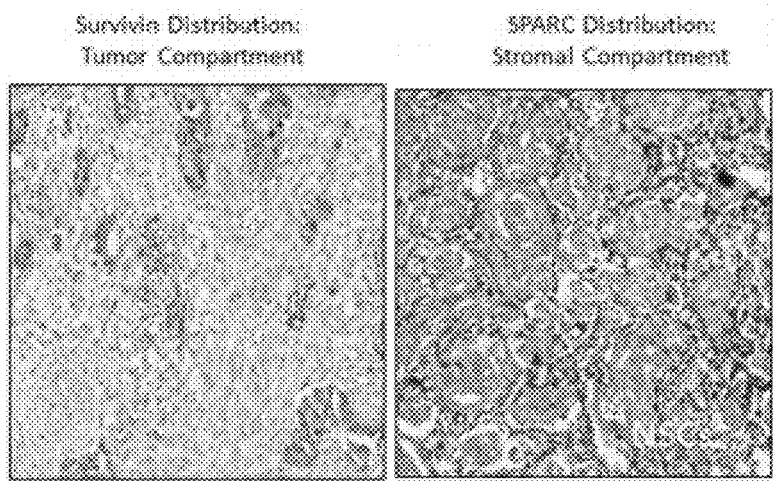
FIGS. 22A-22E show IP NSC.CRAds distribution to peritumoral stroma. (A-B) Brightfield images from the Human Protein Atlas of human ovarian tumor tissue stained with either (A) anti-survivin or (B) anti-SPARC antibodies. (C-D) NSCs (DiI-labeled, red) were injected IP in OVCAR8.eGFP.ffluc (green) tumor-bearing nude mice, harvested 24 hours later, and individual metastatic lesions sectioned all the way through. Every 20th section was stained and imaged. (C) Representative tiled fluorescence microscopy image. (D) 3D reconstruction software was used to compile a z-stack rendering of the NSC distribution throughout the entire metastatic lesion. (E) NSCs labeled with AuNRs (visibly black) were injected IP in OVCAR8-bearing nude mice and harvested 24 h later. Photographs of both omental and mesenteric tumor were taken to demonstrate the presence of black NSCs at the stroma surrounding each metastatic tumor nodule.
Figures 22C, 22D, 22E:
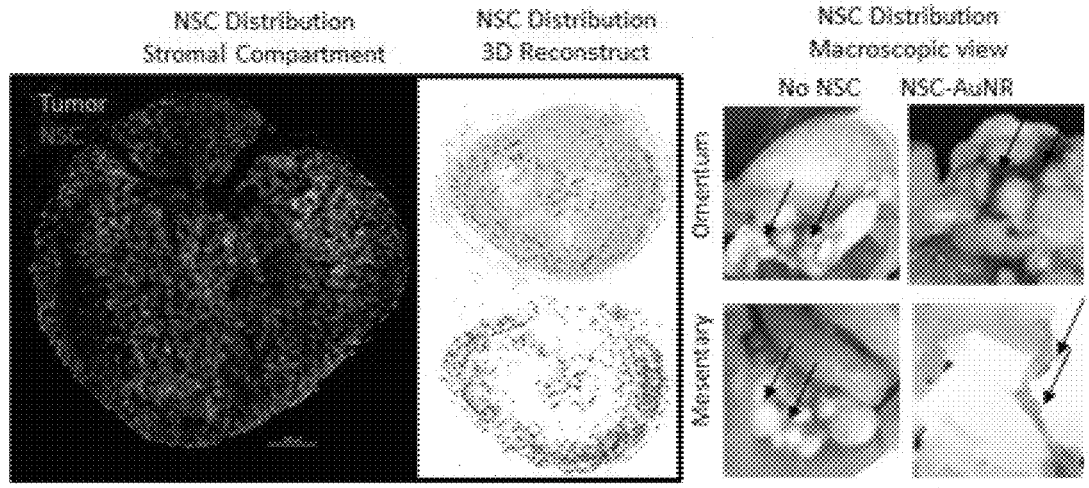

NSC.CRAd-SPARC and NSC.CRAd-Survivin were produced and compared in ovarian cancer models. FIG. 21 shows that NSCs exhibited tropism to ovarian cancer. FIG. 22 shows the expression and distribution of SPARC and survivin. FIG. 23 shows the comparison of in vitro efficacy of CRAd-SPARC and CRAd-Survivin. FIG. 24 demonstrates that NSC-facilitated viral delivery in vivo.

REFERENCES

The references, patents and published patent applications listed below, and all references cited in the specification above are hereby incorporated by reference in their entirety, as if fully set forth herein.

1. Jemal, A., Siegel, R., Ward, E., Hao, Y., Xu, J., Murray, T., & Thun, M. J. (2008). Cancer statistics, 2008. CA Cancer J Clin, 58(2), 71-96.
2. Li, S., Tong, J., Rahman, M. M., Shepherd, T. G., & McFadden, G. (2012). Oncolytic virotherapy for ovarian cancer. Oncolytic Virother, 1, 1-21.
3. Cannistra, S. A. (2004). Cancer of the Ovary. New England Journal of Medicine, 351(24), 2519-29.
4. Kim, J., Hall, R. R., Lesniak, M. S., & Ahmed, A. U. (2015). Stem Cell-Based Cell Carrier for Targeted Oncolytic Virotherapy: Translational Opportunity and Open Questions. Viruses, 7(12), 6200-17.
5. Ding, J. (2014). Oncolytic virus as a cancer stem cell killer: progress and challenges. Stem Cell Investig, 1, 22.
6. Mader, E. K., Maeyama, Y., Lin, Y., Butler, G. W., Russell, H. M., Galanis, E., Russell, S. J., Dietz, A. B., & Peng, K. W. (2009). Mesenchymal stem cell carriers protect oncolytic measles viruses from antibody neutralization in an orthotopic ovarian cancer therapy model. Clin Cancer Res, 15(23), 7246-55.
7. Hartkopf, A. D., Fehm, T., Wallwiener, M., & Lauer, U. (2012). Oncolytic Viruses to Treat Ovarian Cancer Patients—a Review of Results From Clinical Trials. Geburtshilfe Frauenheilkd, 72(2), 132-6.
8. Ahmed, A. U., Thaci, B., Tobias, A. L., Auffinger, B., Zhang, L., Cheng, Y., Kim, C. K., Yunis, C., Han, Y., Alexiades, N. G., Fan, X., Aboody, K. S., & Lesniak, M. S. (2013). A preclinical evaluation of neural stem cell-based cell carrier for targeted antiglioma oncolytic virotherapy. J Natl Cancer Inst, 105(13), 968-77. PMCID: 3699440.
9. Heise, C., Ganly, I., Kim, Y. T., Sampson-Johannes, A., Brown, R., & Kirn, D. (2000). Efficacy of a replication-selective adenovirus against ovarian carcinomatosis is dependent on tumor burden, viral replication and p53 status. Gene Ther, 7(22), 1925-9.
10. Casey, S. C., Tong, L., Li, Y., Do, R., Walz, S., Fitzgerald, K. N., Gouw, A., Baylot, V., Guetegemann, I., Eilers, M., & Felsher, D. W. (2016). MYC regulates the antitumor immune response through CD47 and PD-L1. Science.
11. Duraiswamy, J., Kaluza, K. M., Freeman, G. J., & Coukos, G. (2013). Dual Blockade of PD-1 and CTLA-4 Combined with Tumor Vaccine Effectively Restores T Cell Rejection Function in Tumors. Cancer Res, 73(12), 3591-603.
12. Gaillard, S. L., Secord, A. A., & Monk, B. (2016). The role of immune checkpoint inhibition in the treatment of ovarian cancer. Gynecologic Oncology Research and Practice, 3, 11.
13. Kong, Y.-c. M., & Flynn, J. C. (2014). Opportunistic Autoimmune Disorders Potentiated by Immune-Checkpoint Inhibitors Anti-CTLA-4 and Anti-PD-1. Frontiers in Immunology, 5, 206.
14. Willingham, S. B., Volkmer, J.-P., Gentles, A. J., Sahoo, D., Dalerba, P., Mitra, S. S., Wang, J., Contreras-Trujillo, H., Martin, R., Cohen, J. D., Lovelace, P., Scheeren, F. A., Chao, M. P., Weiskopf, K., Tang, C., Volkmer, A. K., Naik, T. J., Storm, T. A., Mosley, A. R., Edris, B., Schmid, S. M., Sun, C. K., Chua, M.-S., Murillo, O., Rajendran, P., Cha, A. C., Chin, R. K., Kim, D., Adorno, M., Raveh, T., Tseng, D., Jaiswal, S., Enger, P. O., Steinberg, G. K., Li, G., So, S. K., Majeti, R., Harsh, G. R., van de Rijn, M., Teng, N. N. H., Sunwoo, J. B., Alizadeh, A. A., Clarke, M. F., & Weissman, I. L. (2012). The CD47-signal regulatory protein alpha (SIRPα) interaction is a therapeutic target for human solid tumors. Proc Natl Acad Sci USA, 109 (17), 6662-7.
15. Chen, L., & Han, X. (2015). Anti-PD-1/PD-L1 therapy of human cancer: past, present, and future. J Clin Invest, 125(9), 3384-91.
16. Sah, N. K., Khan, Z., Khan, G. J., & Bisen, P. S. (2006). Structural, functional and therapeutic biology of survivin. Cancer Lett, 244(2), 164-71.
17. Liguang, Z., Peishu, L., Hongluan, M., Hong, J., Rong, W., Wachtel, M. S., & Frezza, E. E. (2007). Survivin expression in ovarian cancer. Exp Oncol, 29(2), 121-5.
18. Pesonen, S., Kangasniemi, L., & Hemminki, A. (2011). Oncolytic adenoviruses for the treatment of human cancer: focus on translational and clinical data. Mol Pharm, 8(1), 12-28.
19. Shinoura, N., Yoshida, Y., Tsunoda, R., Ohashi, M., Zhang, W., Asai, A., Kirino, T., & Hamada, H. (1999). Highly augmented cytopathic effect of a fiber-mutant E1B-defective adenovirus for gene therapy of gliomas. Cancer Res, 59(14), 3411-6.
20. Vasey, P. A., Shulman, L. N., Campos, S., Davis, J., Gore, M., Johnston, S., Kim, D. H., O'Neill, V., Siddiqui, N., Seiden, M. V., & Kaye, S. B. (2002). Phase I trial of intraperitoneal injection of the E1B-55-kd-gene-deleted adenovirus ONYX-015 (dl1520) given on days 1 through 5 every 3 weeks in patients with recurrent/refractory epithelial ovarian cancer. J Clin Oncol, 20(6), 1562-9.
21. Douglas, J. T., Kim, M., Sumerel, L. A., Carey, D. E., & Curiel, D. T. (2001). Efficient oncolysis by a replicating adenovirus (ad) in vivo is critically dependent on tumor expression of primary ad receptors. Cancer Res, 61(3), 813-7.
22. Ulasov, I. V., Zhu, Z. B., Tyler, M. A., Han, Y., Rivera, A. A., Khramtsov, A., Curiel, D. T., & Lesniak, M. S. (2007). Survivin-driven and fiber-modified oncolytic adenovirus exhibits potent antitumor activity in established intracranial glioma. Hum Gene Ther, 18(7), 589-602.
23. Mittal, A. K., Chaturvedi, N. K., Rohlfsen, R. A., Gupta, P., Joshi, A. D., Hegde, G. V., Bociek, R. G., & Joshi, S. S. (2013). Role of CTLA4 in the Proliferation and Survival of Chronic Lymphocytic Leukemia. PLoS One, 8(8), e70352.
24. Okazaki, T., & Honjo, T. (2007). PD-1 and PD-1 ligands: from discovery to clinical application. Int Immunol, 19(7), 813-24.
25. Zitvogel, L., & Kroemer, G. (2012). Targeting PD-1/PD-L1 interactions for cancer immunotherapy. Oncoimmunology, 1(8), 1223-5.
26. Ansari, M. J. I., Salama, A. D., Chitnis, T., Smith, R. N., Yagita, H., Akiba, H., Yamazaki, T., Azuma, M., Iwai, H., Khoury, S. J., Auchincloss, H., & Sayegh, M. H. (2003). The Programmed Death-1 (PD-1) Pathway Regulates Autoimmune Diabetes in Nonobese Diabetic (NOD) Mice. J Exp Med, 198(1), 63-9.
27. Joshi, M. N., Whitelaw, B. C., Palomar, M. T., Wu, Y., & Carroll, P. V. (2016). Immune checkpoint inhibitor-related hypophysitis and endocrine dysfunction: clinical review. Clin Endocrinol (Oxf), 85(3), 331-9.
28. Nayerossadat, N., Maedeh, T., & Ali, P. A. (2012). Viral and nonviral delivery systems for gene delivery. Advanced Biomedical Research, 1, 27.
29. Nwanegbo, E., Vardas, E., Gao, W., Whittle, H., Sun, H., Rowe, D., Robbins, P. D., & Gambotto, A. (2004). Prevalence of neutralizing antibodies to adenoviral serotypes 5 and 35 in the adult populations of The Gambia, South Africa, and the United States. Clin Diagn Lab Immunol, 11(2), 351-7.
30. Mader, E. K., Butler, G., Dowdy, S. C., Mariani, A., Knutson, K. L., Federspiel, M. J., Russell, S. J., Galanis, E., Dietz, A. B., & Peng, K. W. (2013). Optimizing patient derived mesenchymal stem cells as virus carriers for a phase I clinical trial in ovarian cancer. J Transl Med, 11, 20.
31. Mickelson, E. M., Longton, G., Anasetti, C., Petersdorf, E., Martin, P., Guthrie, L. A., & Hansen, J. A. (1996). Evaluation of the mixed lymphocyte culture (MLC) assay as a method for selecting unrelated donors for marrow transplantation. Tissue Antigens, 47(1), 27-36.
32. Aboody, K. S., Brown, A., Rainov, N. G., Bower, K. A., Liu, S., Yang, W., Small, J. E., Herrlinger, U., Ourednik, V., Black, P. M., Breakefield, X. O., & Snyder, E. Y. (2000). Neural stem cells display extensive tropism for pathology in adult brain: evidence from intracranial gliomas. Proc Natl Acad Sci USA, 97(23), 12846-51. PMCID: PMC18852.
33. Power, A. T., Wang, J., Falls, T. J., Paterson, J. M., Parato, K. A., Lichty, B. D., Stojdl, D. F., Forsyth, P. A., Atkins, H., & Bell, J. C. (2007). Carrier cell-based delivery of an oncolytic virus circumvents antiviral immunity. Mol Ther, 15(1), 123-30.
34. Zhu, Z. B., Makhija, S. K., Lu, B., Wang, M., Kaliberova, L., Liu, B., Rivera, A. A., Nettelbeck, D. M., Mahasreshti, P. J., Leath, C. A., Barker, S., Yamaoto, M., Li, F., Alvarez, R. D., & Curiel, D. T. (2004). Transcriptional targeting of tumors with a novel tumor-specific survivin promoter. Cancer Gene Ther, 11(4), 256-62.
35. Minev, B., Kohrt, H., Kilinc, M., Chen, N., Feng, A., Pessian, M., Geissinger, U., Haefner, E., Tsoneva, D., Bozhilov, K., Sagiv-Barfi, I., Zhao, X., Rajesekaran, N., Levy, R., & Szalay, A. (2014). Combination immunotherapy with oncolytic vaccinia virus and checkpoint inhibitor following local tumor irradiation. Journal for Immunotherapy of Cancer, 2(Suppl 3), P112-P.
36. Zamarin, D., Holmgaard, R. B., Subudhi, S. K., Park, J. S., Mansour, M., Palese, P., Merghoub, T., Wolchok, J. D., & Allison, J. P. (2014). Localized oncolytic virotherapy overcomes systemic tumor resistance to immune checkpoint blockade immunotherapy. Science translational medicine, 6(226), 226ra32-ra32.
37. Leng, S. X., McElhaney, J. E., Walston, J. D., Xie, D., Fedarko, N. S., & Kuchel, G. A. (2008). ELISA AND MULTIPLEX TECHNOLOGIES FOR CYTOKINE MEASUREMENT IN INFLAMMATION AND AGING RESEARCH. The journals of gerontology Series A, Biological sciences and medical sciences, 63(8), 879-84.
38. He, T.-C., Zhou, S., da Costa, L. T., Yu, J., Kinzler, K. W., & Vogelstein, B. (1998). A simplified system for generating recombinant adenoviruses. Proc Natl Acad Sci USA, 95(5), 2509-14.
39. Mizugaki, H., Yamamoto, N., Murakami, H., Kenmotsu, H., Fujiwara, Y., Ishida, Y., Kawakami, T., & Takahashi, T. (2016). Phase I dose-finding study of monotherapy with atezolizumab, an engineered immunoglobulin monoclonal antibody targeting PD-L1, in Japanese patients with advanced solid tumors. Invest New Drugs, 34(5), 596-603.
40. Kojima, Y., Volkmer, J.-P., McKenna, K., Civelek, M., Lusis, A. J., Miller, C. L., Direnzo, D., Nanda, V., Ye, J., Connolly, A. J., Schadt, E. E., Quertermous, T., Betancur, P., Maegdefessel, L., Matic, L. P., Hedin, U., Weissman, I. L., & Leeper, N. J. (2016). CD47-blocking antibodies restore phagocytosis and prevent atherosclerosis. Nature, 536(7614), 86-90.
41. Hulin-Curtis, S. L., Uusi-Kerttula, H., Jones, R., Hanna, L., Chester, J. D., & Parker, A. L. (2016). Evaluation of CD46 re-targeted adenoviral vectors for clinical ovarian cancer intraperitoneal therapy. Cancer Gene Ther, 23(7), 229-34.
42. Aboody, K. S., Najbauer, J., Metz, M. Z., D'Apuzzo, M., Gutova, M., Annala, A. J., Synold, T. W., Couture, L. A., Blanchard, S., Moats, R. A., Garcia, E., Aramburo, S., Valenzuela, V. V., Frank, R. T., Barish, M. E., Brown, C. E., Kim, S. U., Badie, B., & Portnow, J. (2013). Neural stem cell-mediated enzyme/prodrug therapy for glioma: preclinical studies. Sci Transl Med, 5(184), 184ra59. PMCID: PMC3864887.
43. Bonome, T., Levine, D. A., Shih, J., Randonovich, M., Pise-Masison, C. A., Bogomolniy, F., Ozbun, L., Brady, J., Barrett, J. C., Boyd, J., and Birrer, M. J. (2008). A gene signature predicting for survival in suboptimally debulked patients with ovarian cancer. Cancer Res. 68, 5478-5486.
44. Vathipadiekal, V., Wang, V., Wei, W., Waldron, L., Drapkin, R., Gillette, M., Skates, S., and Birrer, M. (2015). Creation of a human secretome: a novel composite library of human secreted proteins: validation using ovarian cancer gene expression data and a virtual secretome array. Clin. Cancer Res. 21, 4960-4969.
45. Cerami, E., Gao, J., Dogrusoz, U., Gross, B. E., Sumer, S. O., Aksoy, B. A., Jacobsen, A., Byrne, C. J., Heuer, M. L., Larsson, E., et al. (2012). The cBio cancer genomics portal: an open platform for exploring multidimensional cancer genomics data. Cancer Discov. 2, 401-404.
46. Gao, J., Aksoy, B. A., Dogrusoz, U., Dresdner, G., Gross, B., Sumer, S. O., Sun, Y., Jacobsen, A., Sinha, R., Larsson, E., et al. (2013). Integrative analysis of complex cancer genomics and clinical profiles using the cBioPortal. Sci. Signal. 6, p 11.
47. Sprangers, M. C., Lakhai, W., Koudstaal, W., Verhoeven, M., Koel, B. F., Vogels, R., Goudsmit, J., Havenga, M. J., and Kostense, S. (2003). Quantifying adenovirus-neutralizing antibodies by luciferase transgene detection: addressing preexisting immunity to vaccine and gene therapy vectors. J. Clin. Microbiol. 41, 5046-5052.
48. Stallwood, Y., Fisher, K. D., Gallimore, P. H., and Mautner, V. (2000). Neutralisation of adenovirus infectivity by ascitic fluid from ovarian cancer patients. Gene Ther 7, 637-643.
49. Kendall, S. E., Najbauer, J., Johnston, H. F., Metz, M. Z., Li, S., Bowers, M., Garcia, E., Kim, S. U., Barish, M. E., Aboody, K. S., and Glackin, C. A. (2008). Neural stem cell 7 targeting of glioma is dependent on phosphoinositide 3-kinase signaling. Stem Cells 26, 1575-1586.
50. Martini, E., Wittkopf, N., Gunther, C., Leppkes, M., Okada, H., Watson, A. J., Podstawa, E., Backert, I., Amann, K., Neurath, M. F., and Becker, C. (2016). Loss of survivin in intestinal epithelial progenitor cells leads to mitotic catastrophe and breakdown of gut immune homeostasis. Cell Rep. 14, 1062-1073.
51. O'Driscoll, L., Linehan, R., and Clynes, M. (2003). Survivin: role in normal cells and in pathological conditions. Curr. Cancer Drug Targets 3, 131-152.
52. Thaci, B., Ahmed, A. U., Ulasov, I. V., Tobias, A. L., Han, Y., Aboody, K. S., and Lesniak, M. S. (2012). Pharmacokinetic study of neural stem cell-based cell carrier for oncolytic virotherapy: targeted delivery of the therapeutic payload in an orthotopic brain tumor model. Cancer Gene Ther. 19, 431-442.
53. Wickham, T. J., Roelvink, P. W., Brough, D. E., and Kovesdi, I. (1996). Adenovirus targeted to heparan-containing receptors increases its gene delivery efficiency to multiple cell types. Nat. Biotechnol. 14, 1570-1573.
54. Stoff, A., Rivera, A. A., Banerjee, N. S., Mathis, J. M., Espinosa-de-los-Monteros, A., Le, L. P., De la Torre, J. I., Vasconez, L. O., Broker, T. R., Richter, D. F., et al. (2006). Strategies to enhance transductional efficiency of adenoviral-based gene transfer to primary human fibroblasts and keratinocytes as a platform in dermal wounds. Wound Repair Regen 14, 608-617.
55. Ahmed, A. U., Thaci, B., Alexiades, N. G., Han, Y., Qian, S., Liu, F., Balyasnikova, I. V., Ulasov, I. Y., Aboody, K. S., and Lesniak, M. S. (2011). Neural stem cell-based cell carriers enhance therapeutic efficacy of an oncolytic adenovirus in an orthotopic mouse model of human glioblastoma. Mol. Ther 19, 1714-1726.

56. Cao, P., Mooney, R., Tirughana, R., Abidi, W., Aramburo, S., Flores, L., Gilchrist, M., Nwokafor, U., Haber, T., Tiet, P., et al. (2017). Intraperitoneal administration of neural stem cell-nanoparticle conjugates targets chemotherapy to ovarian tumors. Bioconjug. Chem. 28, 1767-1776.

57. Domcke, S., Sinha, R., Levine, D. A., Sander, C., and Schultz, N. (2013). Evaluating cell lines as tumour models by comparison of genomic profiles. Nat. Commun. 4, 2126.

58. Helm, C. W., and States, J. C. (2009). Enhancing the efficacy of cisplatin in ovarian cancer treatment—could arsenic have a role. J. Ovarian Res. 2, 2.

59. Chou, T. C. (2006). Theoretical basis, experimental design, and computerized simulation of synergism and antagonism in drug combination studies. Pharmacol. Rev. 58, 621-681.

60. Mader, E. K., Maeyama, Y., Lin, Y., Butler, G. W., Russell, H. M., Galanis, E., Russell, S. J., Dietz, A. B., and Peng, K. W. (2009). Mesenchymal stem cell carriers protect oncolytic measles viruses from antibody neutralization in an orthotopic ovarian cancer therapy model. Clin. Cancer Res. 15, 7246-7255.

61. Ozols, R. F., and Young, R. C. (1985). High-dose cisplatin therapy in ovarian cancer. Semin. Oncol. 12 (4 Suppl 6), 21-30.

62. Tirughana et al, Mol Ther Methods Clin Dev 2018

The invention claimed is:

1. A method of treating cancer comprising administrating to a subject a therapeutically effective amount of neural stem cells (NSCs) and an oncolytic adenovirus, and administering a therapeutically effective amount of a PD-L1 inhibitor to the subject, before, during, or after administration of the neural stem cells and the oncolytic adenovirus, wherein the ratio of NSCs to the oncolytic adenovirus is about 100:1, about 200:1, about 300:1, about 400:1, about 500:1, about 600:1, about 700:1, about 800:1, about 900:1, about 1000:1, about 1100:1, about 1200:1, about 1300:1, about 1400:1, about 1500:1, about 1600:1, about 1700:1, about 1800:1, about 1900:1, or about 2000:1.

2. The method of claim 1, wherein the neural stem cells and the oncolytic adenovirus are administered simultaneously or sequentially.

3. The method of claim 1, wherein the neural stem cells and the oncolytic adenovirus are administered every day, every other day, every three days, every four days, every five days, every six days, weekly, every 10 days, bi-weekly, or monthly.

4. The method of claim 1, wherein the neural stem cells and the oncolytic adenovirus are administered over the period of about one week, about two weeks, about three weeks, about four weeks, about five weeks, about six weeks, about seven weeks, about eight weeks, about nine weeks, about ten weeks, about twelve weeks, about four months, about five months, about six months, about seven months, about eight months, about nine months, about ten months, about eleven months or about twelve months.

5. The method of claim 1, the neural stem cells and the oncolytic adenovirus are administered by intraperitoneal injection.

6. The method of claim 1, wherein the PD-L1 inhibitor is a PD-L1 antibody or an shRNA against PD-L1 to the subject.

7. The method of claim 1, further comprising administering a therapeutically effective amount of a chemotherapeutical agent for treating the cancer to the subject, before, during, or after administration of the neural stem cells and the oncolytic adenovirus.

8. The method of claim 7, wherein the chemotherapeutic agent is cisplatin, and the cancer is ovarian cancer.

9. The method of claim 1, wherein the oncolytic adenovirus is AR2011.

10. The method of claim 1, wherein the oncolytic adenovirus is CRAd-Survivin-pk7, CRAd-SPARC-pk7, or CRAd-SPARC-pk3/5.

11. The method of claim 1, wherein the cancer is selected from the group consisting of peritoneal cancer, ovarian cancer, bladder cancer, pancreatic cancer, colorectal cancer, gastric cancer, brain cancer, and liver cancer.

12. The method of claim 1, wherein the cancer is a metastatic cancer.

13. A pharmaceutical composition comprising a therapeutically effective amount of neural stem cells (NSCs) and an oncolytic adenovirus, and a therapeutically effective amount of a PD-L1 inhibitor, wherein the ratio of NSCs to the oncolytic adenovirus is about 100:1, about 200:1, about 300:1, about 400:1, about 500:1, about 600:1, about 700:1, about 800:1, about 900:1, about 1000:1, about 1100:1, about 1200:1, about 1300:1, about 1400:1, about 1500:1, about 1600:1, about 1700:1, about 1800:1, about 1900:1, or about 2000:1.

14. The pharmaceutical composition of claim 13, wherein the neural stem cells are transduced with the oncolytic adenovirus.

15. The pharmaceutical composition of claim 13, wherein the PD-L1 inhibitor is a PD-L1 antibody or an shRNA against PD-L1.

16. The method of claim 1, wherein the cancer is ovarian cancer.

* * * * *

UNITED STATES PATENT AND TRADEMARK OFFICE
CERTIFICATE OF CORRECTION

Page 1 of 1

PATENT NO. : 11,413,315 B2
APPLICATION NO. : 16/398108
DATED : August 16, 2022
INVENTOR(S) : Alexandra Jacqueline Annala et al.

It is certified that error appears in the above-identified patent and that said Letters Patent is hereby corrected as shown below:

On the Title Page

In item (72) for Inventors, delete "Jaqueline" and insert --Jacqueline--.

Signed and Sealed this
Tenth Day of January, 2023

Katherine Kelly Vidal
*Director of the United States Patent and Trademark Office*

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Mari v-myc forward primer

<400> SEQUENCE: 1
cctttgttga tttcgccaat                                              20

<210> SEQ ID NO 2
<211> LENGTH: 21
<212> TYPE: DNA
<213> ORGANISM: Artificial Sequence
<220> FEATURE:
<223> OTHER INFORMATION: v-myc Inter R2 reverse primer

<400> SEQUENCE: 2
gcgagcttct ccgacaccac c                                            21

<210> SEQ ID NO 3
<211> LENGTH: 24
<212> TYPE: DNA
<213> ORGANISM: Artificial Sequence
<220> FEATURE:
<223> OTHER INFORMATION: Nested v-mycGAG 1306F forward primer

<400> SEQUENCE: 3
tcacagccag atatccagca gctt                                         24

<210> SEQ ID NO 4
<211> LENGTH: 20
<212> TYPE: DNA
<213> ORGANISM: Artificial Sequence
<220> FEATURE:
<223> OTHER INFORMATION: Nested v-myc R1 reverse primer

<400> SEQUENCE: 4
agttctcctc ctcctcctcg                                              20

<210> SEQ ID NO 5
<211> LENGTH: 20
<212> TYPE: DNA
<213> ORGANISM: Artificial Sequence
<220> FEATURE:
<223> OTHER INFORMATION: Hexon3F forward primer

<400> SEQUENCE: 5
ttccgcttca ctggactctt                                              20
```

```
<210> SEQ ID NO 6
<211> LENGTH: 19
<212> TYPE: DNA
<213> ORGANISM: Artificial Sequence
<220> FEATURE:
<223> OTHER INFORMATION: Hexon3R reverse primer

<400> SEQUENCE: 6
tggacagcga ggagagaag                                                    19

<210> SEQ ID NO 7
<211> LENGTH: 23
<212> TYPE: DNA
<213> ORGANISM: Artificial Sequence
<220> FEATURE:
<223> OTHER INFORMATION: GAPDH forward primer

<400> SEQUENCE: 7
atgttcgtca tgggtgtgaa cca                                               23

<210> SEQ ID NO 8
<211> LENGTH: 23
<212> TYPE: DNA
<213> ORGANISM: Artificial Sequence
<220> FEATURE:
<223> OTHER INFORMATION: GAPDH reverse primer

<400> SEQUENCE: 8
tggcaggttt ttctagacgg cag                                               23
```